United States Patent
Wang

(10) Patent No.: US 11,421,039 B2
(45) Date of Patent: Aug. 23, 2022

(54) SACCHARIDE-BASED BIOMARKERS AND THERAPEUTICS

(71) Applicant: B & H Biotechnologies, LLC, Willowbrook, IL (US)

(72) Inventor: Huiru Wang, Beijing (CN)

(73) Assignee: B & H Biotechnologies, LLC, Willowbrook, IL (US)

( * ) Notice: Subject to any disclaimer, the term of this patent is extended or adjusted under 35 U.S.C. 154(b) by 372 days.

(21) Appl. No.: 16/785,465

(22) Filed: Feb. 7, 2020

(65) Prior Publication Data
US 2020/0239591 A1    Jul. 30, 2020

Related U.S. Application Data

(62) Division of application No. 15/505,064, filed as application No. PCT/CN2015/087717 on Aug. 21, 2015, now Pat. No. 10,597,461.

(30) Foreign Application Priority Data

Aug. 22, 2014    (WO) .................. PCTCN2014085027

(51) Int. Cl.
| | | |
|---|---|---|
| *A61K 39/00* | (2006.01) | |
| *C07K 16/28* | (2006.01) | |
| *A61K 39/395* | (2006.01) | |
| *C07K 16/30* | (2006.01) | |
| *C07K 16/44* | (2006.01) | |
| *G01N 33/574* | (2006.01) | |
| *A61K 45/06* | (2006.01) | |

(52) U.S. Cl.
CPC ........ *C07K 16/30* (2013.01); *A61K 39/39558* (2013.01); *A61K 45/06* (2013.01); *C07K 16/44* (2013.01); *G01N 33/574* (2013.01); *G01N 33/57407* (2013.01); *G01N 33/57411* (2013.01); *G01N 33/57415* (2013.01); *G01N 33/57423* (2013.01); *G01N 33/57438* (2013.01); *G01N 33/57449* (2013.01); *G01N 33/57488* (2013.01); *G01N 33/57492* (2013.01); *A61K 2039/505* (2013.01); *C07K 2317/21* (2013.01); *C07K 2317/24* (2013.01); *C07K 2317/31* (2013.01); *C07K 2317/33* (2013.01); *C07K 2317/34* (2013.01); *C07K 2317/56* (2013.01); *C07K 2317/76* (2013.01); *C12N 2720/12311* (2013.01); *G01N 2400/02* (2013.01); *G01N 2400/40* (2013.01); *G01N 2800/06* (2013.01)

(58) Field of Classification Search
None
See application file for complete search history.

(56) References Cited

U.S. PATENT DOCUMENTS

| | | |
|---|---|---|
| 4,816,567 A | 3/1989 | Cabilly et al. |
| 8,957,188 B2 | 2/2015 | Gildersleeve et al. |
| 10,597,461 B2 | 3/2020 | Wang |
| 2006/0292643 A1 | 12/2006 | Goletz et al. |
| 2009/0324617 A1 | 12/2009 | Satomaa et al. |
| 2010/0254898 A1 | 10/2010 | Gildersleeve et al. |
| 2010/0254971 A1 | 10/2010 | Dotan et al. |
| 2012/0040375 A1 | 2/2012 | Nishimura et al. |
| 2013/0045543 A1 | 2/2013 | Nishimura et al. |
| 2019/0038669 A1 | 2/2019 | Wang |

FOREIGN PATENT DOCUMENTS

| | | |
|---|---|---|
| CN | 102178686 A | 9/2011 |
| CN | 102372773 A | 3/2012 |
| CN | 104198707 A | 12/2014 |
| CN | 104267185 A | 1/2015 |
| CN | 105177031 A | 12/2015 |
| CN | 105246912 A | 1/2016 |
| EP | 0390115 A1 | 10/1990 |
| EP | 0407586 A1 | 1/1991 |
| EP | 0404097 B1 | 9/1996 |
| WO | 1993/11161 A1 | 6/1993 |
| WO | 2008/055242 A2 | 5/2008 |

(Continued)

OTHER PUBLICATIONS

Almagro et al., "Humanization of Antibodies", Frontiers in Bio-Science, vol. 13, 2008, pp. 1619-1633.
Barczak et al., "Universal Real-time PCR-based Assay for Lentiviral Titration", Molecular Biotechnology, vol. 57, 2015, pp. 195-200.
Barthelemy et al., "Comprehensive Analysis of the Factors Contributing to the Stability and Solubility of Autonomous Human VH Domains", The Journal of Biological Chemistry, vol. 283, No. 6, Feb. 8, 2008, pp. 3639-3654.

(Continued)

*Primary Examiner* — Christine J Saoud
(74) *Attorney, Agent, or Firm* — Morrison & Foerster LLP

(57) ABSTRACT

The invention provides antibodies that specifically bind to an epitope containing N-acetylglucosamine or N-acetyl-galactosamine expressed by a cancer cell or an inflammatory cell. Also provided are compositions including these antibodies, as well as polynucleotides, vectors, host cells, and methods useful for production thereof. Further provided are methods and kits for treating or preventing cancer in an individual by administering to the individual an antibody that specifically binds to an epitope containing N-acetylglucosamine or N-acetyl-galactosamine, optionally in combination with another anti-cancer agent. Still further provided are methods and kits for treating or preventing gastrointestinal disease in an individual by administering to the individual an antibody that specifically binds to an epitope containing N-acetylglucosamine or N-acetyl-galactosamine. Yet further provided are methods and kits for detecting the presence of cancer cells in an individual including an antibody that specifically binds to an epitope containing N-acetylglucosamine and/or N-acetyl-galactosamine.

10 Claims, 16 Drawing Sheets

Specification includes a Sequence Listing.

(56) References Cited

FOREIGN PATENT DOCUMENTS

| WO | 2011/012309 A1 | 2/2011 |
|---|---|---|
| WO | 2011/054359 A2 | 5/2011 |
| WO | 2014/159244 A2 | 10/2014 |
| WO | 2016/026456 A1 | 2/2016 |

OTHER PUBLICATIONS

Beiboer et al., "Guided Selection of a Pan Carcinoma Specific Antibody Reveals Similar Binding Characteristics yet Structural Divergence Between the Original Murine Antibody and Its Human Equivalent", Journal of Molecular Biology, vol. 296, Issue 3, 25 Fe, 2000, pp. 833-849.

Berglund et al., "The Epitope Space of the Human Proteome", Protein Science, vol. 17, 2008, pp. 606-613.

Boerner et al., "Production of Antigen-specific Human Monoclonal Antibodies from in Vitro-primed Human Splenocytes.", The Journal of Immunology, vol. 147, No. 1, Jul. 1, 1991, pp. 86-95.

Brooks et al., "Expression of Alpha-Galnac Glycoproteins by Breast Cancers", British Journal of Cancer, vol. 71, 1995, pp. 1033-1038.

Choi et al., "Predicting Antibody Complementarity Determining Region Structures Without Classification", Molecular BioSystems, vol. 7, 2011, pp. 3327-3334.

Chothia et al., "Canonical Structures for the Hypervariable Regions of Immunoglobulins", Journal of Molecular Biology, vol. 196, Aug. 20, 1987, pp. 901-917.

Clackson et al., "Making Antibody Fragments Using Phage Display Libraries", Nature, vol. 352, Aug. 15, 1991, pp. 624-628.

Comer et al., "Characterization of a Mouse Monoclonal Antibody Specific for O-linked N-acetylglucosamine", Analytical Biochemistry, vol. 293, 2001, pp. 169-177.

Corada et al., "Monoclonal Antibodies Directed to Different Regions of Vascular Endothelial Cadherin Extracellular Domain Affect Adhesion and Clustering of the Protein and Modulate Endothelial Permeability", Blood, vol. 97, No. 6, Mar. 15, 2001, pp. 1679-1684.

Dai et al., "Chimeric Antigen Receptors Modified T-cells for Cancer Therapy", Journal of the National Cancer Institute, vol. 108, No. 7, 2016, pp. 1-14.

Danielczyk et al., "Pankomab: A Potent New Generation Anti-Tumour Muc1 Antibody", Cancer Immunol Immunother, vol. 55, 2006, pp. 1337-1347.

De Genst et al., "Antibody Repertoire Development in Camelids", Developmental & Comparative Immunology, vol. 30, 2006, pp. 187-198.

Extended European Search Report (includes Supplementary European Search Report and Search Opinion) received for European Patent Application No. 15833676.8, dated Dec. 22, 2017, 10 pages.

Fan et al., "A New Tumor Marker: Mu-Glcnac", Labeled Immunoassays and Clinical Medicine, vol. 21, 2014, pp. 514-515.

Gerngross, Tillman U., "Advances in the Production of Human Therapeutic Proteins in Yeasts and Filamentous Fungi", Nature Biotechnology, vol. 22, No. 11, Nov. 2004, pp. 1409-1414.

Graham et al., "Characteristics of a Human Cell Line Transformed by DNA from Human Adenovirus Type 5", Journal of General Virology, vol. 36, 1977, pp. 59-72.

Griffiths et al., "Human Anti-Self Antibodies with High Specificity from Phage Display Libraries", The EMBO Journal vol. 12, No. 2, 1993, pp. 725-734.

Holliger et al., ""diabodies": Small Bivalent and Bispecific Antibody Fragments", Proceedings of the National Academy of Sciences, vol. 90, Jul. 1993, pp. 6444-6448.

International Search Report and Written Opinion received for PCT Patent Application No. PCT/CN2014/085027, dated May 28, 2015, 13 pages.

International Search Report and Written Opinion received for PCT Patent Application No. PCT/CN2015/087717 dated Nov. 17, 2015, 13 pages.

International Search Report and Written Opinion received for PCT Patent Application No. PCT/CN2016/074146, dated Sep. 28, 2016, 12 pages.

International Search Report and Written Opinion received for PCT Patent Application No. PCT/CN2017/073890, dated May 9, 2017, 12 pages.

Ito et al., "Monoclonal IGM in Two Patients with Motor Neuron Disease Bind to the Carbohydrate Antigens Gal(β1-3)galnac and Gal(β1-3)glcnac", Journal of Neuroimmunology, vol. 19, 1988, pp. 245-253.

Jakobovits et al., "Analysis of Homozygous Mutant Chimeric Mice: Deletion of the Immunoglobulin Heavy-chain Joining Region Blocks B-cell Development and Antibody Production", Proceedings of the National Academy of Sciences, vol. 90, Mar. 1993, pp. 2551-2555.

Jansson et al., "The Human Repertoire of Antibody Specificities Against Thomsen-Friedenreich and Tn-carcinoma-associated Antigens as Defined by Human Monoclonal Antibodies", Cancer Immunology Immunotherapy, vol. 34:, 1992, pp. 294-298.

Jones et al., "Replacing the Complementarity-determining Regions in a Human Antibody with Those from a Mouse", Nature, vol. 321, May 29, 1986, pp. 522-525.

Kipriyanov et al., "Generation and Production of Engineered Antibodies", Molecular Biotechnology, vol. 26, 2004, pp. 39-60.

Klimka et al., "Human Anti-cd30 Recombinant Antibodies by Guided Phage Antibody Selection Using Cell Panning", British Journal of Cancer, 83, No. 2, 2000, pp. 252-260.

Kohler et al., "Continuous Cultures of Fused Cells Secreting Antibody of Predefined Specificity", Nature, vol. 256, Aug. 7, 1975, pp. 495-497.

Kulkarni-Kale et al., "Cep: A Conformational Epitope Prediction Server", Nucleic Acids Research, vol. 33, 2005, pp. W168-W171.

Lonberg et al., "Antigen-specific Human Antibodies from Mice Comprising Four Distinct Genetic Modifications", Nature, vol. 368, Apr. 28, 1994, pp. 856-859.

Maher et al., "Human T-lymphocyte Cytotoxicity and Proliferation Directed by a Single Chimeric Tcr? /cd28 Receptor", Nature Biotechnology, vol. 20, Jan. 2002, pp. 70-75.

Moremen et al., "Vertebrate Protein Glycosylation: Diversity, Synthesis and Function", Nature Reviews Molecular Cell Biology, vol. 13, No. 7, 2012, pp. 448-462.

Morrison et al., "Chimeric Human Antibody Molecules: Mouse Antigen-binding Domains with Human Constant Region Domains", Proc. Nat'l Acad. Sci, vol. 81, Nov. 1984, pp. 6851-6855.

Non-Final Office Action received for U.S. Appl. No. 15/505,064, dated May 13, 2019, 29 pages.

Padlan, Eduardo A., "X-ray Crystallography of Antibodies", Advances in Protein Chemistry, vol. 49, 1996, pp. 57-133.

Plückthun, A., "Antibodies from *Escherichia coli*", Chapter 11, The Pharmacology of Monoclonal Antibodies, 1994, pp. 269-315.

Presta, Leonard G., "Antibody Engineering", Current Opinion in Structural Biology, vol. 2, 1992, pp. 593-596.

Restriction Requirement received for U.S. Appl. No. 15/505,064, dated Dec. 13, 2018, 10 pages.

Richmond et al., "Mouse Xenograft Models Vs Gem Models for Human Cancer Therapeutics", Disease Models & Mechanisms, vol. 1, 2008, pp. 78-82.

Riechmann et al., "Reshaping Human Antibodies for Therapy", Nature, vol. 332, Mar. 24, 1988, pp. 323-327.

Ryuko et al., "Characterization of a New Muc1 Monoclonal Antibody (vu-2-g7) Directed to the Glycosylated PDTR Sequence of Muc1", Tumor Biology, vol. 21, Aug. 2000, pp. 197-210.

Savoldo et al., "Cd28 Costimulation Improves Expansion and Persistence of Chimeric Antigen Receptor-modified T Cells in Lymphoma Patients", The Journal of Clinical Investigation, vol. 121, No. 5, May 2011, pp. 1822-1826.

Seow et al., "Novel Anti-Glycan Antibodies Related to Infl Ammatory Bowel Disease Diagnosis and Phenotype", The American Journal of Gastroenterology, vol. 104, Jun. 2009, pp. 1426-1434.

Smorodin et al., "The Characterization of Igg Antibodies to Galnac Beta-terminated Glycans of Gastric Cancer Survivors", Experimental Oncology, vol. 36, No. 1, Mar. 2014, pp. 38-43.

Tsubokawa et al., "A Monoclonal Antibody, Pgm34, Against 6-sulfated Blood-group H Type 2 Antigen, on the Carbohydrate Moiety of Mucin", FEBS Journal, vol. 274, 2007, pp. 1833-1848.

(56) References Cited

OTHER PUBLICATIONS

Urlaub et al., "Isolation of Chinese Hamster Cell Mutants Deficient in Dihydrofolate Reductase Activity", Proc. Natl. Acad. Sci., vol. 77, No. 7, Jul. 1980, pp. 4216-4220.
Ward et al., "Binding Activities of a Repertoire of Single Immunoglobulin Variable Domains Secreted from *Escherichia coli*", Nature, vol. 341, Oct. 12, 1989, pp. 544-546.
Zhang et al., "Protein O-Glcnacylation and Cancer", Tumor, vol. 33, No. 11, 2013, pp. 1027-1032.

| The results of human tumor-antigen-binding test with monoclonal antibodies | | | | | | | | | | | |
|---|---|---|---|---|---|---|---|---|---|---|---|
| Ab Name | PBS | NAG | GalNAc | SMMC-7721 | NCI-H446 | SPC-A1 | MCF-7 | SW11/b | ECAP-1090 | LCS-Ag1 | LCS-Ag2 |
| 1B3E12 | - | 4+ | 4+ | - | - | + | - | - | - | - | - |
| 3C4F12 | - | 4+ | 4+ | 3+ | 2+ | 3+ | ± | 4+ | 4+ | 4+ | 2+ |
| 7E6A10 | - | 4+ | 4+ | - | - | + | - | - | - | 2+ | - |
| 1C5C9 | - | 4+ | 4+ | + | 2+ | 2+ | - | 3+ | 2+ | ND | ND |
| 2F7H4 | - | 4+ | 3+ | 3+ | 4+ | 4+ | 4+ | 3+ | 3+ | ND | ND |
| 7C10H11 | - | 4+ | 2+ | + | + | 2+ | ± | 4+ | + | ND | ND |
| 8D9B12 | - | 2+ | 2+ | - | + | - | + | - | - | ND | ND |
| 4C8C12 | - | 4+ | 3+ | - | - | - | - | - | - | - | - |
| 7E6C12 | - | 4+ | 3+ | - | - | - | - | - | - | - | - |
| 7G1E12 | - | 4+ | 2+ | - | - | - | - | - | - | ND | ND |
| 4E1G10 | - | - | - | - | - | - | - | - | - | ND | ND |
| 4H6H7 | - | - | - | - | - | - | - | - | - | ND | ND |
| NAG: N-Acetyl-Glucosamine; GalNAc: N-Acetyl-Galactosamine; SMMC-7721: hepatocarcinoma; | | | | | | | | | | | |
| NCI-H446: small cell lung cancer; SPC-A1: lung adenocarcinoma; MCF-7: breast adenocarcinoma | | | | | | | | | | | |
| SW11/b: colon carcinoma; ECAP-1090: esophagus adenocarcinoma | | | | | | | | | | | |
| LCS-Ag: Lung Cancer Self Antigen from patient with lung cancer; ND: not done | | | | | | | | | | | |

FIG. 3

| The inhibitory rate (%) of MAb-2F7H4 on human tumor cells | | | | | |
|---|---|---|---|---|---|
| MAb (ug/ml) | U251 | SMMC-7721 | NCI-H446 | SK-MES-1 | SPC-A1 |
| 25 | 35 | 18 | 0 | 5 | 34 |
| 12.5 | 35 | 11 | 0 | 3 | 48 |
| 6.25 | 55 | 22 | 0 | 11 | 45 |
| 3.125 | 66 | 30 | 16 | 16 | 52 |
| 1.563 | 66 | 34 | 11 | 37 | 54 |
| 0.8 | 60 | 38 | 11 | 23 | 52 |
| 0.4 | 62 | 30 | 0 | 17 | 51 |
| 0.2 | 64 | 39 | 0 | 26 | 53 |
| 0.1 | 61 | 37 | 6 | 9 | 46 |
| 0.05 | 50 | 29 | 3 | 8 | 37 |
| 0.025 | 42 | 23 | 0 | 0 | 29 |
| 0.0125 | 43 | 17 | 12 | 0 | 23 |
| 0.006 | 37 | 29 | 11 | 0 | 17 |
| 0.003 | 20 | 4 | 0 | 0 | 29 |
| U251: glioma; SMMC: hepatocarcinoma; NCI-H446: small cell lung cancer | | | | | |
| SK-MES-1: lung squamous cell carcinoma; SPC-A1: lung adenocarcinoma | | | | | |
| Method: 96-well plate, MTT assay | | | | | |

FIG. 4

| The inhibitory rate (%) of MAb-1C5C9 on human tumor cells | | | | | |
|---|---|---|---|---|---|
| MAb (ug/ml) | U251 | SMMC-7721 | NCI-H446 | SK-MES-1 | SPC-A1 |
| 25 | 18 | 53 | 0 | 52 | 38 |
| 12.5 | 27 | 42 | 6 | 67 | 37 |
| 6.25 | 50 | 51 | 17 | 61 | 35 |
| 3.125 | 34 | 36 | 28 | 76 | 27 |
| 1.563 | 30 | 55 | 28 | 76 | 23 |
| 0.8 | 36 | 78 | 23 | 77 | 22 |
| 0.4 | 41 | 73 | 19 | 78 | 48 |
| 0.2 | 50 | 72 | 0 | 68 | 53 |
| 0.1 | 61 | 37 | 4 | 49 | 56 |
| 0.05 | 50 | 29 | 6 | 38 | 37 |
| 0.025 | 52 | 23 | 0 | 21 | 29 |
| 0.0125 | 43 | 17 | 0 | 17 | 23 |
| 0.006 | 37 | 29 | 0 | 12 | 17 |
| 0.003 | 30 | 4 | 0 | 18 | 29 |
| U251: glioma; SMMC: hepatocarcinoma; NCI-H446: small cell lung cancer | | | | | |
| SK-MES-1: lung squamous cell carcinoma; SPC-A1: lung adenocarcinoma | | | | | |
| Method: 96-well plate, MTT assay | | | | | |

FIG. 5

| The inhibitory rate (%) of MAb-3C4F12 on human tumor cells | | | | | |
|---|---|---|---|---|---|
| MAb (ug/ml) | U251 | SMMC-7721 | NCI-H446 | SK-MES-1 | SPC-A1 |
| 25.0 | 32 | 24 | 0 | 20 | 25 |
| 12.5 | 23 | 34 | 42 | 10 | 36 |
| 6.25 | 16 | 9 | 39 | 80 | 18 |
| 3.125 | 22 | 22 | 50 | 94 | 18 |
| 1.563 | 8 | 20 | 52 | 50 | 18 |
| 0.80 | 20 | 23 | 39 | 27 | 17 |
| 0.40 | 14 | 23 | 34 | 23 | 17 |
| 0.20 | 17 | 13 | 0 | 0 | 8 |
| U251: glioma; SMMC: hepatocarcinoma; NCI-H446: small cell lung cancer | | | | | |
| SK-MES-1: lung squamous cell carcinoma; SPC-A1: lung adenocarcinoma | | | | | |
| Method: 96-well plate, MTT assay | | | | | |

FIG. 6

| The Results (%) of ELISA assay with serum samples and MAb-1C5C9 | | | | | | | | |
|---|---|---|---|---|---|---|---|---|
| Sera of | N = | - / ± | + | 2+ | 3+ | 4+ | Total + | Total ≥ 2+ |
| Healthy | 38 | 89.5 | 7.89 | 2.63 | 0.00 | 0.00 | 10.5 | 2.63 |
| Lung Cancer | 34 | 2.94 | 23.5 | 47.1 | 17.6 | 8.82 | 97.1 | 70.6 |
| Breast Cancer | 29 | 6.89 | 17.2 | 41.4 | 24.1 | 10.3 | 93.1 | 79.3 |
| Thyroid Cancer | 14 | 7.14 | 42.9 | 42.9 | 7.14 | 0.00 | 92.8 | 50.0 |
| Colon cancer | 16 | 6.25 | 31.2 | 43.7 | 18.8 | 0.00 | 93.7 | 66.7 |
| Method: 96-well ELISA plate, duplicate; MAb concentration: 2ug/ml. | | | | | | | | |

The Results of flow cytometry assay with monoclonal antibody-2F7H4 and PBMCs from cancer patients and healthy individuals

| Grade | | -/± (%) | + (%) | 2+ (%) | 3+ (%) | 4+ (%) | Total + | Total ≥ 2+ |
|---|---|---|---|---|---|---|---|---|
| PBMC of | N = | 1.3% - 2.2% | 2.3% - 4.9% | 5.0% - 7.4% | 7.5% - 9.9% | ≥ 10.0% | % | % |
| Healthy individuals | 10 | 100 | 0.00 | 0.00 | 0.00 | 0.00 | 0.00 | 0.00 |
| Lung cancer | 21 | 38.1 | 47.6 | 9.52 | 0.00 | 4.76 | 61.9 | 14.3 |
| Liver cancer | 19 | 47.4 | 42.1 | 10.5 | 0.00 | 0.00 | 52.6 | 10.5 |
| Breast cancer | 7 | 14.3 | 85.7 | 0.00 | 0.00 | 0.00 | 85.7 | 0.00 |
| Colon/colorectal cancer | 6 | 0.00 | 83.3 | 16.7 | 0.00 | 0.00 | 100 | 16.7 |
| Esophagus cancer | 5 | 40.0 | 60.0 | 0.00 | 0.00 | 0.00 | 60.0 | 0.00 |
| Stomach cancer | 4 | 25.0 | 25.0 | 0.00 | 0.00 | 50.0 | 75.0 | 50.0 |
| Endometrial cancer | 4 | 25.0 | 50.0 | 25.0 | 0.00 | 0.00 | 75.0 | 25.0 |
| Cervical cancer | 3 | 33.3 | 33.3 | 33.3 | 0.00 | 0.00 | 66.7 | 33.3 |
| Thyroid cancer | 3 | 33.3 | 66.7 | 0.00 | 0.00 | 0.00 | 66.7 | 0.00 |
| Brain cancer | 3 | 33.3 | 66.7 | 0.00 | 0.00 | 0.00 | 66.7 | 0.00 |
| Lymphoma | 3 | 33.3 | 66.7 | 0.00 | 0.00 | 0.00 | 66.7 | 0.00 |
| Bone cancer | 2 | 2 (ND) | 0.00 | 0.00 | 0.00 | 0.00 | ND | ND |
| Ovary cancer | 1 | 0.00 | 1 (ND) | 0.00 | 0.00 | 0.00 | ND | ND |
| Skin cancer | 1 | 1 (ND) | 0.00 | 0.00 | 0.00 | 0.00 | ND | ND |
| Kidney cancer | 1 | 1 (ND) | 0.00 | 0.00 | 0.00 | 0.00 | ND | ND |
| Prostate cancer | 1 | 1 (ND) | 0.00 | 0.00 | 0.00 | 0.00 | ND | ND |

PBMC: peripheral blood mononuclear cell; ND: not analyzed

FIG. 11

The Results of flow cytometry assay with monoclonal antibody-1C5C9 and PBMCs from cancer patients and healthy individuals

| Grade | | -/± (%) | + (%) | 2+ (%) | 3+ (%) | 4+ (%) | Total + | Total ≥ 2+ |
|---|---|---|---|---|---|---|---|---|
| PBMC of | N = | 2.4% - 3.3% | 3.4% - 6.4% | 6.5% - 8.4% | 8.5% - 10.9% | ≥ 11.0% | % | % |
| Healthy individuals | 10 | 100 | 0.00 | 0.00 | 0.00 | 0.00 | 0.00 | 0.00 |
| Lung cancer | 15 | 66.7 | 6.67 | 13.3 | 0.00 | 13.3 | 33.3 | 13.3 |
| Breast Cancer | 13 | 46.2 | 17.8 | 7.69 | 0.00 | 7.69 | 53.8 | 15.4 |
| Liver cancer | 11 | 36.4 | 45.5 | 18.1 | 0.00 | 0.00 | 63.6 | 18.1 |
| Thyroid cancer | 10 | 70.0 | 0.00 | 20.0 | 10.0 | 0.00 | 30.0 | 30.0 |
| Ovary cancer | 7 | 85.7 | 0.00 | 0.00 | 0.00 | 14.3 | 14.3 | 14.3 |
| Esophagus cancer | 4 | 75.0 | 0.00 | 0.00 | 0.00 | 25.0 | 25.0 | 25.0 |
| Colon/colorectal cancer | 3 | 0.00 | 33.3 | 0.00 | 0.00 | 66.7 | 100 | 66.7 |
| Cervical cancer | 3 | 66.7 | 33.3 | 0.00 | 0.00 | 0.00 | 33.3 | 0.00 |
| Pancreas cancer | 3 | 66.7 | 0.00 | 0.00 | 33.3 | 0.00 | 33.3 | 33.3 |
| Bone cancer | 2 | 1 (ND) | 1 (ND) | 0.00 | 0.00 | 0.00 | ND | ND |
| Stomach cancer | 1 | 0.00 | 1 (ND) | 0.00 | 0.00 | 0.00 | ND | ND |
| Endometrial cancer | 1 | 0.00 | 0.00 | 1 (ND) | 0.00 | 0.00 | ND | ND |
| Brain cancer | 1 | 0.00 | 1 (ND) | 0.00 | 0.00 | 0.00 | ND | ND |
| Lymphoma | 1 | 0.00 | 1 (ND) | 0.00 | 0.00 | 0.00 | ND | ND |
| Skin cancer | 1 | 0.00 | 1 (ND) | 0.00 | 0.00 | 0.00 | ND | ND |
| Kidney cancer | 1 | 0.00 | 1 (ND) | 0.00 | 0.00 | 0.00 | ND | ND |
| Prostate cancer | 1 | 1 (ND) | 0.00 | 0.00 | 0.00 | 0.00 | ND | ND |

PBMC: peripheral blood mononuclear cell; ND: not analyzed

FIG. 12

| The Results of flow cytometry assay with monoclonal antibody-1B3E12 and PBMCs from cancer patients and healthy individuals | | | | | | | | |
|---|---|---|---|---|---|---|---|---|
| Grade | | -/± (%) | + (%) | 2+ (%) | 3+ (%) | 4+ (%) | Total + | Total ≥ 2+ |
| PBMC of | N = | 2.3% - 3.2% | 3.3% - 6.4% | 6.5 - 8.4% | 8.5 - 10.9% | ≥ 11.0% | % | % |
| Healthy individuals | 10 | 100 | 0.00 | 0.00 | 0.00 | 0.00 | 0.00 | 0.00 |
| Breast cancer | 12 | 50.0 | 33.3 | 16.7 | 0.00 | 0.00 | 50.0 | 16.7 |
| Liver cancer | 10 | 70.0 | 10.0 | 0.00 | 0.00 | 20.0 | 30.0 | 20.0 |
| Ovary cancer | 7 | 71.4 | 14.3 | 0.00 | 0.00 | 14.3 | 28.6 | 14.3 |
| Colon/colorectal cancer | 3 | 33.3 | 0.00 | 33.3 | 0.00 | 33.3 | 66.7 | 33.3 |
| Pancreas cancer | 3 | 66.7 | 0.00 | 33.3 | 0.00 | 0.00 | 33.3 | 33.3 |
| Esophagus cancer | 2 | 1 (ND) | 0.00 | 0.00 | 0.00 | 1 (ND) | ND | ND |
| Lung cancer | 2 | 0.00 | 1 (ND) | 0.00 | 1 (ND) | 0.00 | ND | ND |
| Bone cancer | 2 | 1 (ND) | 1 (ND) | 0.00 | 0.00 | 0.00 | ND | ND |
| Endometrial cancer | 1 | 0.00 | 1 (ND) | 0.00 | 0.00 | 0.00 | ND | ND |
| Brain cancer | 1 | 1 (ND) | 0.00 | 0.00 | 0.00 | 0.00 | ND | ND |
| Lymphoma | 1 | 0.00 | 0.00 | 1 (ND) | 0.00 | 0.00 | ND | ND |
| Skin cancer | 1 | 0.00 | 1 (ND) | 0.00 | 0.00 | 0.00 | ND | ND |
| Kidney cancer | 1 | 1 (ND) | 0.00 | 0.00 | 0.00 | 0.00 | ND | ND |
| Prostate cancer | 1 | 1 (ND) | 0.00 | 0.00 | 0.00 | 0.00 | ND | ND |
| PBMC: peripheral blood mononuclear cell; ND: not analyzed | | | | | | | | |

FIG. 13

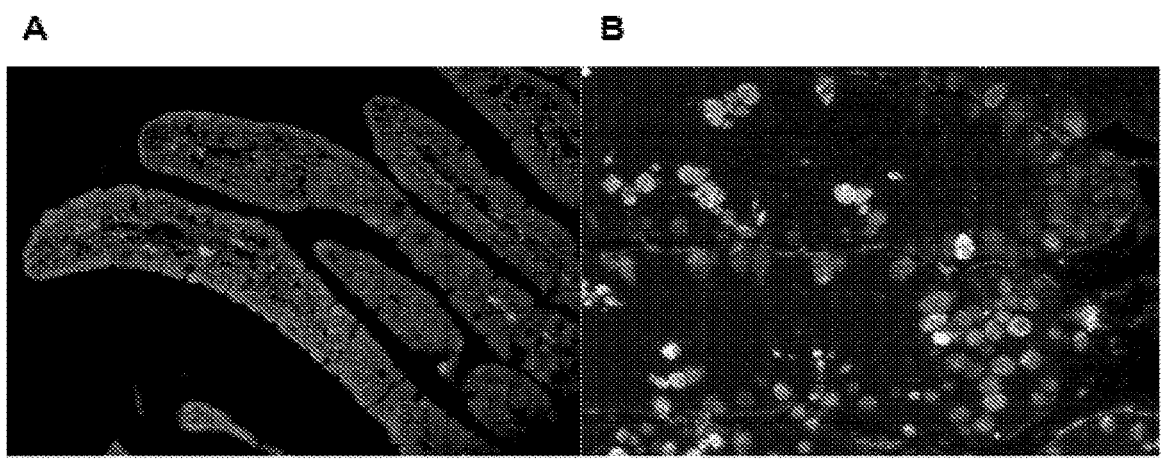

FIG. 14

SEQUENCE LISTING

<160> NUMBER OF SEQ ID NOS: 37

<210> SEQ ID NO 1
<211> LENGTH: 117
<212> TYPE: PRT
<213> ORGANISM: Artificial Sequence
<220> FEATURE:
<223> OTHER INFORMATION: Synthetic Construct

<400> SEQUENCE: 1

Glu Val Lys Leu Gln Gln Ser Gly Gly Gly Leu Val Gln Pro Gly Gly
1               5                   10                  15

Ser Leu Arg Leu Ser Cys Ala Thr Ser Gly Phe Thr Phe Ser Asp Phe
            20                  25                  30

Tyr Met Glu Trp Val Arg Gln Pro Pro Gly Lys Arg Leu Glu Trp Ile

```
            35                  40                  45
Ala Ala Ser Arg Asn Lys Ala Asn Asp Tyr Thr Thr Glu Tyr Ser Ala
    50                  55                  60

Ser Val Lys Gly Arg Phe Ile Val Ser Arg Asp Thr Ser Gln Ser Ile
65                  70                  75                  80

Leu Tyr Leu Gln Met Asn Ala Leu Arg Ala Glu Asp Thr Ala Ile Tyr
                85                  90                  95

Tyr Cys Ala Arg Asp Ala Trp Phe Ala Tyr Trp Gly Gln Gly Thr Ile
            100                 105                 110

Val Thr Val Ser Ser
        115

<210> SEQ ID NO 2
<211> LENGTH: 113
<212> TYPE: PRT
<213> ORGANISM: Artificial Sequence
<220> FEATURE:
<223> OTHER INFORMATION: Synthetic Construct

<400> SEQUENCE: 2

Asp Ile Val Ile Thr Gln Thr Pro Ser Ser Leu Ala Val Ser Val Gly
1               5                   10                  15

Glu Lys Val Thr Met Ser Cys Lys Ser Ser Gln Ser Leu Leu Tyr Ser
                20                  25                  30

Ser Asn Gln Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Arg Thr Phe Gly Gly Gly Thr Lys Phe Glu Ile
            100                 105                 110

Lys

<210> SEQ ID NO 3
<211> LENGTH: 122
<212> TYPE: PRT
<213> ORGANISM: Artificial Sequence
<220> FEATURE:
<223> OTHER INFORMATION: Synthetic Construct

<400> SEQUENCE: 3

Glu Val Gln Leu Glu Glu Ser Gly Pro Glu Leu Val Lys Pro Gly Ala
1               5                   10                  15

Ser Val Lys Ile Ser Cys Lys Ala Ser Gly Tyr Thr Phe Pro Asp Tyr
                20                  25                  30

Asn Ile His Trp Val Lys Gln Ser His Gly Lys Ser Leu Glu Trp Ile
            35                  40                  45

Gly Cys Ile Tyr Pro Tyr Asn Gly Asn Thr Ala Tyr Asn Gln Lys Phe
    50                  55                  60

Lys Thr Lys Ala Thr Leu Thr Val Asp Thr Ser Ser Ser Thr Ala Tyr
65                  70                  75                  80

Met Asp Leu Arg Ser Leu Thr Ser Glu Asp Ser Ala Val Tyr Tyr Cys
                85                  90                  95

Ala Arg Ser Asp Leu Tyr Tyr Phe Gly Ser Arg Gly Phe Val Tyr Trp
```

```
                      100                 105                 110
Gly Gln Gly Thr Thr Val Thr Val Ser Ser
            115                 120

<210> SEQ ID NO 4
<211> LENGTH: 107
<212> TYPE: PRT
<213> ORGANISM: Artificial Sequence
<220> FEATURE:
<223> OTHER INFORMATION: Synthetic Construct

<400> SEQUENCE: 4

Asp Ile Val Leu Thr Gln Ser Pro Ser Ser Leu Ser Ala Ser Leu Gly
1               5                   10                  15

Asp Arg Val Thr Ile Ser Cys Arg Ala Ser Gln Asp Ile Ser Thr Tyr
            20                  25                  30

Leu Asn Trp Tyr Gln Gln Lys Pro Asp Gly Thr Val Lys Leu Leu Val
        35                  40                  45

Tyr Phe Thr Ser Arg Leu His Ser Gly Val Pro Ser Arg Phe Ser Gly
    50                  55                  60

Thr Gly Ser Gly Thr Asp Phe Ser Leu Thr Ile Asn Asn Leu Asp Gln
65                  70                  75                  80

Glu Asp Ile Ala Thr Tyr Phe Cys Gln Gln Gly Asn Thr Leu Pro Trp
                85                  90                  95

Thr Phe Gly Gly Gly Thr Lys Leu Glu Ile Lys
            100                 105

<210> SEQ ID NO 5
<211> LENGTH: 121
<212> TYPE: PRT
<213> ORGANISM: Artificial Sequence
<220> FEATURE:
<223> OTHER INFORMATION: Synthetic Construct

<400> SEQUENCE: 5

Glu Val Gln Leu Glu Glu Ser Gly Gly Gly Leu Val Lys Pro Gly Gly
1               5                   10                  15

Ser Leu Lys Leu Ser Cys Ala Ala Ser Gly Phe Ala Phe Ser Ser Tyr
            20                  25                  30

Asp Met Ser Trp Val Arg Gln Thr Pro Glu Lys Arg Leu Glu Trp Val
        35                  40                  45

Ala Tyr Ile Ser Ser Gly Gly Gly Ser Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg Arg Tyr Tyr Tyr Gly Ser Ser Trp Ala Met Asp Tyr Trp Gly
            100                 105                 110

Gln Gly Thr Met Val Thr Val Ser Ser
            115                 120

<210> SEQ ID NO 6
<211> LENGTH: 107
<212> TYPE: PRT
<213> ORGANISM: Artificial Sequence
<220> FEATURE:
<223> OTHER INFORMATION: Synthetic Construct

<400> SEQUENCE: 6
```

-continued

```
Asp Ile Val Met Thr Gln Ser Thr Lys Phe Leu Leu Val Ser Ala Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Gln Ser Pro Lys Leu Leu Ile
        35                  40                  45

Tyr Tyr Ala Ser Asn Arg Tyr Thr Gly Val Pro Asp Arg Phe Thr Gly
50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ser Pro Tyr
                85                  90                  95

Thr Phe Gly Gly Gly Thr Lys Leu Glu Ile Lys
            100                 105
```

<210> SEQ ID NO 7
<211> LENGTH: 9
<212> TYPE: PRT
<213> ORGANISM: Artificial Sequence
<220> FEATURE:
<223> OTHER INFORMATION: Synthetic Construct

<400> SEQUENCE: 7

```
Tyr Thr Phe Pro Asp Tyr Asn Ile His
1               5
```

<210> SEQ ID NO 8
<211> LENGTH: 10
<212> TYPE: PRT
<213> ORGANISM: Artificial Sequence
<220> FEATURE:
<223> OTHER INFORMATION: Synthetic Construct

<400> SEQUENCE: 8

```
Cys Ile Tyr Pro Tyr Asn Gly Asn Thr Ala
1               5                   10
```

<210> SEQ ID NO 9
<211> LENGTH: 12
<212> TYPE: PRT
<213> ORGANISM: Artificial Sequence
<220> FEATURE:
<223> OTHER INFORMATION: Synthetic Construct

<400> SEQUENCE: 9

```
Ser Asp Leu Tyr Tyr Phe Gly Ser Arg Gly Phe Asp
1               5                   10
```

<210> SEQ ID NO 10
<211> LENGTH: 11
<212> TYPE: PRT
<213> ORGANISM: Artificial Sequence
<220> FEATURE:
<223> OTHER INFORMATION: Synthetic Construct

<400> SEQUENCE: 10

```
Gln Ala Ser Gln Asp Ile Ser Thr Tyr Leu Asn
1               5                   10
```

<210> SEQ ID NO 11
<211> LENGTH: 11
<212> TYPE: PRT
<213> ORGANISM: Artificial Sequence -continued

```
<220> FEATURE:
<223> OTHER INFORMATION: Synthetic Construct

<400> SEQUENCE: 11

Arg Ala Ser Gln Asp Ile Ser Thr Tyr Leu Asn
1               5                   10

<210> SEQ ID NO 12
<211> LENGTH: 7
<212> TYPE: PRT
<213> ORGANISM: Artificial Sequence
<220> FEATURE:
<223> OTHER INFORMATION: Synthetic Construct

<400> SEQUENCE: 12

Phe Thr Ser Asn Leu Glu Thr
1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic Construct

<400> SEQUENCE: 13

Phe Thr Ser Ser Leu Gln Ser
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic Construct

<400> SEQUENCE: 14

Phe Thr Ser Arg Leu His Ser
1               5

<210> SEQ ID NO 15
<211> LENGTH: 8
<212> TYPE: PRT
<213> ORGANISM: Artificial Sequence
<220> FEATURE:
<223> OTHER INFORMATION: Synthetic Construct

<400> SEQUENCE: 15

Gln Gln Gly Asn Thr Leu Pro Trp
1               5

<210> SEQ ID NO 16
<211> LENGTH: 123
<212> TYPE: PRT
<213> ORGANISM: Artificial Sequence
<220> FEATURE:
<223> OTHER INFORMATION: Synthetic Construct

<400> SEQUENCE: 16

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Pro Asp Tyr
                20                  25                  30

Asn Ile His Trp Val Arg Gln Ala Pro Gly Gln Gly Leu Glu Trp Met
            35                  40                  45
```

```
Gly Cys Ile Tyr Pro Tyr Asn Gly Asn Thr Ala Tyr Ala Gln Lys Phe
     50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Ser Asp Leu Tyr Tyr Phe Gly Ser Arg Gly Phe Asp Tyr Trp
             100                 105                 110

Gly Gln Gly Thr Leu Val Thr Val Ser Ser Ala
            115                 120

<210> SEQ ID NO 17
<211> LENGTH: 452
<212> TYPE: PRT
<213> ORGANISM: Artificial Sequence
<220> FEATURE:
<223> OTHER INFORMATION: Synthetic Construct

<400> SEQUENCE: 17

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Pro Asp Tyr
                 20                  25                  30

Asn Ile His Trp Val Arg Gln Ala Pro Gly Gln Gly Leu Glu Trp Met
             35                  40                  45

Gly Cys Ile Tyr Pro Tyr Asn Gly Asn Thr Ala Tyr Ala Gln Lys Phe
     50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Ser Asp Leu Tyr Tyr Phe Gly Ser Arg Gly Phe Asp Tyr Trp
             100                 105                 110

Gly Gln Gly Thr Leu Val Thr Val Ser Ser Ala Ser Thr Lys Gly Pro
            115                 120                 125

Ser Val Phe Pro Leu Ala Pro Ser Ser Lys Ser Thr Ser Gly Gly Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285
```

```
Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 18
<211> LENGTH: 105
<212> TYPE: PRT
<213> ORGANISM: Artificial Sequence
<220> FEATURE:
<223> OTHER INFORMATION: Synthetic Construct

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Thr Tyr
            20                  25                  30

Leu Asn Trp Tyr Gln Gln Lys Pro Gly Lys Ala Pro Lys Leu Leu Ile
        35                  40                  45

Tyr Phe Thr Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Gln Gln Gly Asn Thr Leu Pro Trp
                85                  90                  95

Thr Phe Gly Gly Gly Thr Lys Leu Glu
            100                 105

<210> SEQ ID NO 19
<211> LENGTH: 212
<212> TYPE: PRT
<213> ORGANISM: Artificial Sequence
<220> FEATURE:
<223> OTHER INFORMATION: Synthetic Construct

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Thr Tyr
            20                  25                  30
```

```
Leu Asn Trp Tyr Gln Gln Lys Pro Gly Lys Ala Pro Lys Leu Leu Ile
        35                  40                  45

Tyr Phe Thr Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Gln Gln Gly Asn Thr Leu Pro Trp
                85                  90                  95

Thr Phe Gly Gly Gly Thr Lys Leu Glu Arg Thr Val Ala Ala Pro Ser
            100                 105                 110

Val Phe Ile Phe Pro Pro Ser Asp Glu Gln Leu Lys Ser Gly Thr Ala
        115                 120                 125

Ser Val Val Cys Leu Leu Asn Asn Phe Tyr Pro Arg Glu Ala Lys Val
    130                 135                 140

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
                165                 170                 175

Leu Thr Leu Ser Lys Ala Asp Tyr Glu Lys His Lys Val Tyr Ala Cys
            180                 185                 190

Glu Val Thr His Gln Gly Leu Ser Ser Pro Val Thr Lys Ser Phe Asn
        195                 200                 205

Arg Gly Glu Cys
    210

<210> SEQ ID NO 20
<211> LENGTH: 105
<212> TYPE: PRT
<213> ORGANISM: Artificial Sequence
<220> FEATURE:
<223> OTHER INFORMATION: Synthetic Construct

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Thr Tyr
            20                  25                  30

Leu Asn Trp Tyr Gln Gln Lys Pro Gly Lys Ala Pro Lys Leu Leu Ile
        35                  40                  45

Tyr Phe Thr Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Gln Gln Gly Asn Thr Leu Pro Trp
                85                  90                  95

Thr Phe Gly Gly Gly Thr Lys Leu Glu
            100                 105

<210> SEQ ID NO 21
<211> LENGTH: 212
<212> TYPE: PRT
<213> ORGANISM: Artificial Sequence
<220> FEATURE:
<223> OTHER INFORMATION: Synthetic Construct

<400> SEQUENCE: 21

Asp Ile Gln Met Thr Gln Ser Pro Ser Ser Leu Ser Ala Ser Val Gly
```

-continued

```
              1               5                  10                 15
            Asp Arg Val Thr Ile Thr Cys Arg Ala Ser Gln Asp Ile Ser Thr Tyr
                            20                  25                 30

Leu Asn Trp Tyr Gln Gln Lys Pro Gly Lys Ala Pro Lys Leu Leu Ile
                        35                  40                 45

Tyr Phe Thr Ser Ser Leu Gln Ser Gly Val Pro Ser Arg Phe Ser Gly
                    50                  55                  60

Ser Gly Ser Gly Thr Asp Phe Thr Leu Thr Ile Ser Ser Leu Gln Pro
            65                  70                  75                  80

Glu Asp Ile Ala Thr Tyr Tyr Cys Gln Gln Gly Asn Thr Leu Pro Trp
                            85                  90                  95

Thr Phe Gly Gly Gly Thr Lys Leu Glu Arg Thr Val Ala Ala Pro Ser
                            100                 105                110

Val Phe Ile Phe Pro Pro Ser Asp Glu Gln Leu Lys Ser Gly Thr Ala
                        115                 120                125

Ser Val Val Cys Leu Leu Asn Asn Phe Tyr Pro Arg Glu Ala Lys Val
                    130                 135                 140

Gln Trp Lys Val Asp Asn Ala Leu Gln Ser Gly Asn Ser Gln Glu Ser
            145                 150                 155                 160

Val Thr Glu Gln Asp Ser Lys Asp Ser Thr Tyr Ser Leu Ser Ser Thr
                            165                 170                 175

Leu Thr Leu Ser Lys Ala Asp Tyr Glu Lys His Lys Val Tyr Ala Cys
                        180                 185                 190

Glu Val Thr His Gln Gly Leu Ser Ser Pro Val Thr Lys Ser Phe Asn
                    195                 200                 205

Arg Gly Glu Cys
            210

<210> SEQ ID NO 22
            <211> LENGTH: 105
            <212> TYPE: PRT
            <213> ORGANISM: Artificial Sequence
            <220> FEATURE:
            <223> OTHER INFORMATION: Synthetic Construct

<400> SEQUENCE: 22

Asp Ile Gln Met Thr Gln Ser Pro Ser Ser Leu Ser Ala Ser Val Gly
            1               5                  10                 15

Asp Arg Val Thr Ile Thr Cys Arg Ala Ser Gln Asp Ile Ser Thr Tyr
                            20                  25                 30

Leu Asn Trp Tyr Gln Gln Lys Pro Gly Lys Ala Pro Lys Leu Leu Ile
                        35                  40                 45

Tyr Phe Thr Ser Arg Leu His Ser Gly Val Pro Ser Arg Phe Ser Gly
                    50                  55                  60

Ser Gly Ser Gly Thr Asp Phe Thr Leu Thr Ile Ser Ser Leu Gln Pro
            65                  70                  75                  80

Glu Asp Ile Ala Thr Tyr Tyr Cys Gln Gln Gly Asn Thr Leu Pro Trp
                            85                  90                  95

Thr Phe Gly Gly Gly Thr Lys Leu Glu
                            100                 105

<210> SEQ ID NO 23
            <211> LENGTH: 212
            <212> TYPE: PRT
            <213> ORGANISM: Artificial Sequence
            <220> FEATURE:
            <223> OTHER INFORMATION: Synthetic Construct
```

<400> SEQUENCE: 23

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Thr Tyr
            20                  25                  30

Leu Asn Trp Tyr Gln Gln Lys Pro Gly Lys Ala Pro Lys Leu Leu Ile
        35                  40                  45

Tyr Phe Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Gln Gln Gly Asn Thr Leu Pro Trp
                85                  90                  95

Thr Phe Gly Gly Gly Thr Lys Leu Glu Arg Thr Val Ala Ala Pro Ser
            100                 105                 110

Val Phe Ile Phe Pro Pro Ser Asp Glu Gln Leu Lys Ser Gly Thr Ala
        115                 120                 125

Ser Val Val Cys Leu Leu Asn Asn Phe Tyr Pro Arg Glu Ala Lys Val
130                 135                 140

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
                165                 170                 175

Leu Thr Leu Ser Lys Ala Asp Tyr Glu Lys His Lys Val Tyr Ala Cys
            180                 185                 190

Glu Val Thr His Gln Gly Leu Ser Ser Pro Val Thr Lys Ser Phe Asn
        195                 200                 205

Arg Gly Glu Cys
    210

<210> SEQ ID NO 24
<211> LENGTH: 9
<212> TYPE: PRT
<213> ORGANISM: Artificial Sequence
<220> FEATURE:
<223> OTHER INFORMATION: Synthetic Construct

<400> SEQUENCE: 24

Phe Thr Phe Ser Asp Phe Tyr Met Glu
1               5

<210> SEQ ID NO 25
<211> LENGTH: 19
<212> TYPE: PRT
<213> ORGANISM: Artificial Sequence
<220> FEATURE:
<223> OTHER INFORMATION: Synthetic Construct

<400> SEQUENCE: 25

Ala Ser Arg Asn Lys Ala Asn Asp Tyr Thr Thr Glu Tyr Ser Ala Ser
1               5                   10                  15

Val Lys Gly

<210> SEQ ID NO 26
<211> LENGTH: 5
<212> TYPE: PRT
<213> ORGANISM: Artificial Sequence
<220> FEATURE:

<223> OTHER INFORMATION: Synthetic Construct

<400> SEQUENCE: 26

Asp Ala Trp Phe Ala
1               5

<210> SEQ ID NO 27
<211> LENGTH: 17
<212> TYPE: PRT
<213> ORGANISM: Artificial Sequence
<220> FEATURE:
<223> OTHER INFORMATION: Synthetic Construct

<400> SEQUENCE: 27

Lys Ser Ser Gln Ser Leu Leu Tyr Ser Ser Asn Gln Lys Asn Tyr Leu
1               5                   10                  15
Ala

<210> SEQ ID NO 28
<211> LENGTH: 7
<212> TYPE: PRT
<213> ORGANISM: Artificial Sequence
<220> FEATURE:
<223> OTHER INFORMATION: Synthetic Construct

<400> SEQUENCE: 28

Trp Ala Ser Thr Arg Glu Ser
1               5

<210> SEQ ID NO 29
<211> LENGTH: 8
<212> TYPE: PRT
<213> ORGANISM: Artificial Sequence
<220> FEATURE:
<223> OTHER INFORMATION: Synthetic Construct

<400> SEQUENCE: 29

Gln Gln Tyr Tyr Ser Tyr Pro Arg
1               5

<210> SEQ ID NO 30
<211> LENGTH: 17
<212> TYPE: PRT
<213> ORGANISM: Artificial Sequence
<220> FEATURE:
<223> OTHER INFORMATION: Synthetic Construct

<400> SEQUENCE: 30

Cys Ile Tyr Pro Tyr Asn Gly Asn Thr Ala Tyr Asn Gln Lys Phe Lys
1               5                   10                  15
Thr

<210> SEQ ID NO 31
<211> LENGTH: 12
<212> TYPE: PRT
<213> ORGANISM: Artificial Sequence
<220> FEATURE:
<223> OTHER INFORMATION: Synthetic Construct

<400> SEQUENCE: 31

Ser Asp Leu Tyr Tyr Phe Gly Ser Arg Gly Phe Val
1               5                   10

<210> SEQ ID NO 32
<211> LENGTH: 9

```
<212> TYPE: PRT
<213> ORGANISM: Artificial Sequence
<220> FEATURE:
<223> OTHER INFORMATION: Synthetic Construct

<400> SEQUENCE: 32

Phe Ala Phe Ser Ser Tyr Asp Met Ser
1               5

<210> SEQ ID NO 33
<211> LENGTH: 17
<212> TYPE: PRT
<213> ORGANISM: Artificial Sequence
<220> FEATURE:
<223> OTHER INFORMATION: Synthetic Construct

<400> SEQUENCE: 33

Tyr Ile Ser Ser Gly Gly Gly Ser Thr Tyr Tyr Pro Asp Thr Val Lys
1               5                   10                  15
Gly

<210> SEQ ID NO 34
<211> LENGTH: 11
<212> TYPE: PRT
<213> ORGANISM: Artificial Sequence
<220> FEATURE:
<223> OTHER INFORMATION: Synthetic Construct

<400> SEQUENCE: 34

Arg Tyr Tyr Tyr Gly Ser Ser Trp Ala Met Asp
1               5                   10

<210> SEQ ID NO 35
<211> LENGTH: 11
<212> TYPE: PRT
<213> ORGANISM: Artificial Sequence
<220> FEATURE:
<223> OTHER INFORMATION: Synthetic Construct

<400> SEQUENCE: 35

Lys Ala Ser Gln Ser Val Ser Asn Asp Val Ala
1               5                   10

<210> SEQ ID NO 36
<211> LENGTH: 7
<212> TYPE: PRT
<213> ORGANISM: Artificial Sequence
<220> FEATURE:
<223> OTHER INFORMATION: Synthetic Construct

<400> SEQUENCE: 36

Tyr Ala Ser Asn Arg Tyr Thr
1               5

<210> SEQ ID NO 37
<211> LENGTH: 8
<212> TYPE: PRT
<213> ORGANISM: Artificial Sequence
<220> FEATURE:
<223> OTHER INFORMATION: Synthetic Construct

<400> SEQUENCE: 37

Gln Gln Asp Tyr Ser Ser Pro Tyr
1               5
```

SACCHARIDE-BASED BIOMARKERS AND THERAPEUTICS

CROSS-REFERENCE TO RELATED APPLICATIONS

This application is a Divisional of U.S. patent application Ser. No. 15/505,064, filed Feb. 17, 2017, issued as U.S. Pat. No. 10,597,461 on Mar. 24, 2020, which is a National Phase application under 35 U.S.C. § 371 of International Application No. PCT/CN2015/087717, filed Aug. 21, 2015, which claims the priority benefit of International Patent Application Serial No. PCT/CN2014/085027, filed Aug. 22, 2014, the contents of which are hereby incorporated by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 735182000210SEQLIST.txt, date recorded: Feb. 7, 2020, size: 29 KB).

FIELD

This invention relates to antibodies that specifically bind N-acetylglucosamine or N-acetyl-galactosamine expressed by a cancer cell or an inflammatory cell, as well as compositions, polynucleotides, vectors, host cells, methods of production, methods of use, and kits related thereto.

BACKGROUND

Cancer is one of the most challenging disorders to treat in modern medicine for several reasons. Since cancer arises from the abnormal behavior of one's own cells, distinguishing cancer cells from normal cells within a patient is a difficult problem. Often the body's own immune system has difficulty identifying and eliminating cancerous cells. In addition, "cancer" refers to a constellation of individual disorders, i.e. types and subtypes of cancer. Many different cell types can become cancerous through many different mechanisms, resulting in a tremendous phenotypic variety in the types of cancer cells that may arise. This diversity is highly problematic for cancer treatment because different types of cancer cells may have different identifying properties for diagnosis, or they may possess different therapeutic weaknesses or resistant properties. This problem makes it difficult to come up with ways to diagnose, treat, and/or prevent multiple types of cancer through a single therapeutic strategy or agent. Even though oncology has advanced tremendously in the last decade, there is still a need to identify new biomarkers specific to cancer cells, particularly biomarkers that characterize multiple types of cancer but not normal tissues.

Cell surface molecules are highly important for cancer cells. These molecules are critically involved in cell-cell interactions, which are important for many cancer cell behaviors, including cell invasion, metastasis, evasion of the immune system, and responses to therapeutic agents. Cancer cells are known to express many cell surface proteins differently from normal cells. However, many cell surface proteins are modified by the addition of saccharides N-acetylglucosamine or N-acetyl-galactosamine), a process termed protein glycosylation. How specific cell surface proteins are modified by the addition of saccharides, which saccharides may be found on which cell surface proteins, and how patterns of glycosylation change during different types or phases of carcinogenesis are all problems that are just beginning to be explored (for a review, see Moremen, K. W., et al. (2012) *Nat. Rev. Mol. Cell Biol.* 13(7): 448-62). This diversity in glycosylation increases the complexity of cancer cell recognition by surface biomarkers. Therefore, there remains a need for new biomarkers and therapeutic agents useful in the diagnosis, treatment, and prevention of cancer, particularly for biomarkers and agents that target cancer-specific patterns of glycosylation.

All references cited herein, including patent applications, patent publications, and UniProtKB/Swiss-Prot Accession numbers are herein incorporated by reference in their entirety, as if each individual reference were specifically and individually indicated to be incorporated by reference

BRIEF SUMMARY

To meet the demand for new biomarkers and therapeutic agents useful in the diagnosis, treatment, and prevention of multiple types of cancer, disclosed herein are monoclonal antibodies that specifically bind N-acetylglucosamine or N-acetyl-galactosamine expressed by a cancer cell or an inflammatory cell, as well as compositions, polynucleotides, vectors, host cells, methods of production, and kits related thereto. Further disclosed are methods of treating or preventing cancer in an individual by administering antibodies that specifically bind N-acetylglucosamine or N-acetyl-galactosamine expressed on a cell surface of a cancer cell, and methods of diagnosing cancer using antibodies that specifically bind N-acetylglucosamine or N-acetyl-galactosamine. These compositions and methods are based in part on the surprising discovery that human cancer cells representing many different types of cancer express higher levels of N-acetylglucosamine and/or N-acetyl-galactosamine than normal human tissues. Moreover, the present disclosure demonstrates the surprising result that antibodies that specifically bind N-acetylglucosamine and/or N-acetyl-galactosamine expressed on a cell surface of a cancer cell are highly potent and effective in reducing the growth rate of several diverse types of cancer cells, both in vitro and in vivo. Additionally, the present application describes the unexpected finding that antibodies that specifically bind N-acetylglucosamine or N-acetyl-galactosamine may be used as an effective preventative and treatment for gastrointestinal diseases, such as viral infection, inflammatory bowel disease, and hemorrhoids.

In one aspect, provided herein are antibodies that specifically bind to an epitope comprising N-acetylglucosamine and/or N-acetyl-galactosamine, where the epitope is expressed by a cancer cell or inflammatory cell. Also provided are compositions comprising these antibodies, as well as polynucleotides, vectors, host cells, and methods useful in the production thereof. Further provided are methods and kits useful for treating or preventing cancer in an individual by administering to the individual an antibody that specifically binds to an epitope comprising N-acetylglucosamine or N-acetyl-galactosamine, optionally in combination with another anti-cancer agent. Further provided are methods and kits useful for treating or preventing gastrointestinal disease in an individual by administering to the individual an antibody that specifically binds to an epitope comprising N-acetylglucosamine or N-acetyl-galactosamine. Yet further provided are methods and kits useful for detecting the presence of cancer cells in an individual by obtaining a biological sample from an individual, contacting the biological sample with an antibody that specifically binds to an epitope comprising N-acetylglucosamine and/or N-acetyl-galactosamine, and detecting the amount of antibody binding to the biological sample, where antibody binding indicates the presence of cancer cells in the individual.

In certain aspects, the present disclosure provides an isolated monoclonal antibody, which antibody specifically binds to an epitope comprising N-acetylglucosamine or N-acetyl-galactosamine, wherein the epitope is expressed by a cancer cell or an inflammatory cell. In certain embodiments, the antibody specifically binds to an epitope comprising N-acetylglucosamine and an epitope comprising N-acetyl-galactosamine. In certain embodiments that may be combined with any of the preceding embodiments, the antibody, is an antibody fragment. In certain embodiments, the antibody is a Fab fragment, scFv, minibody, diabody scFv multimer, or bispecific antibody fragment. In certain embodiments, the antibody is a humanized antibody. In certain embodiments, the antibody is a human antibody. In certain embodiments, the antibody is a chimeric antibody. In certain embodiments that may be combined with any of the preceding embodiments, the epitope is expressed on a cell surface the cancer cell. In certain embodiments that may be combined with any of the preceding embodiments, the epitope is expressed in the cancer cell. In certain embodiments that may be combined with any of the preceding embodiments, the cancer cell is selected from a glioma cell, a hepatocarcinoma cell, a lung cancer cell, a breast cancer cell, an ovarian carcinoma cell, and a cervical adenocarcinoma cell. In certain embodiments, the lung cancer cell is a small cell lung cancer cell, a lung squamous cell carcinoma cell, or a lung adenocarcinoma cell. In certain embodiments, the binding of the antibody to the epitope inhibits growth of the cancer cell. In certain embodiments, the inflammatory cell is an intestinal inflammatory cell of colitis, inflammatory bowel disease, or gastroenteritis, and the epitope is expressed on a cell surface of the inflammatory cell. In certain embodiments, the antibody comprises a heavy chain variable region comprising three HVRs from the amino acid sequence of SEQ ID NO:1, and a light chain variable region comprising three HVRs from the amino acid sequence of SEQ ID NO:2. In certain embodiments the antibody comprises a heavy chain variable region comprising an HVR-H1 sequence of SEQ ID NO: 24, an HVR-H2 sequence of SEQ ID NO: 25, and an HVR-H3 sequence of SEQ ID NO: 26; and a light chain variable region comprising an HVR-L1 sequence of SEQ ID NO: 27, an HVR-L2 sequence of SEQ ID NO: 28, and an HVR-L3 sequence of SEQ ID NO: 29. In certain embodiments, the antibody comprises a heavy chain variable region comprising the amino acid sequence of SEQ ID NO:1, and/or a light chain variable region comprising the amino acid sequence of SEQ ID NO:2. In certain embodiments, the antibody comprises a heavy chain variable region comprising three HVRs from the amino acid sequence of SEQ ID NO:3, and a light chain variable region comprising three HVRs from the amino acid sequence of SEQ NO:4. In certain embodiments the antibody comprises a heavy chain variable region comprising an HVR-H1 sequence of SEQ ID NO: 7, an HVR-H2 sequence of SEQ ID NO: 30, and an HVR-H3 sequence of SEQ ID NO: 31; and a light chain variable region comprising an HVR-L1 sequence of SEQ ID NO: 11, an HVR-L2 sequence of SEQ ID NO: 14, and an HVR-L3 sequence of SEQ ID NO: 15. In certain embodiments the antibody comprises a heavy chain variable region comprising the amino acid sequence of SEQ NO:3, and/or a light chain variable region comprising the amino acid sequence of SEQ ID NO: 4. In certain embodiments, the antibody comprises a heavy chain variable region comprising three HVRs from the amino acid sequence of SEQ ID NO:5, and a light chain variable region comprising three HVRs from the amino acid sequence of SEQ ID NO:6. In certain embodiments, the antibody comprises a heavy chain variable region comprising an HVR-H1 sequence of SEQ ID NO: 32, an sequence of SEQ ID NO: 33, and an HVR-H3 sequence of SEQ ID NO: 34; and a light chain variable region comprising an HVR-L1 sequence of SEQ ID NO: 35, an HVR-L2 sequence of SEQ ID NO: 36, and an HVR-L3 sequence of SEQ ID NO: 37. In certain embodiments, the antibody comprises a heavy chain variable region comprising, the amino acid sequence of SEQ ID NO:5, and/or a light chain variable region comprising the amino acid sequence of SEQ ID NO:6. In certain embodiments, the antibody comprises a heavy chain variable region comprising an HVR-H1 sequence of SEQ ID NO: 7, an HVR-H2 sequence of SEQ ID NO: 8, and an HVR-H3 sequence of SEQ ID NO: 9; and a light chain variable region comprising an HVR-L1 sequence of SEQ ID NO: 10, an HVR-L2 sequence of SEQ ID NO: 12, and an HVR-L3 sequence of SEQ ID NO: 15. In certain embodiments, the antibody comprises a heavy chain variable region comprising the amino acid sequence of SEQ ID NO: 16, and/or a light chain variable region comprising the amino acid sequence of SEQ ID NO: 18. In certain embodiments, the antibody comprises a heavy chain variable region comprising an HVR-H1 sequence of SEQ ID NO: 7, an HVR-H2 sequence of SEQ ID NO: 8, and an HVR-H3 sequence of SEQ ID NO: 9; and a light chain variable region comprising an HVR-L1 sequence of SEQ ID NO: 11, an HVR-L2 sequence of SEQ ID NO: 13, and an HVR-L3 sequence of SEQ ID NO: 15. In certain embodiments, the antibody comprises a heavy chain variable region comprising the amino acid sequence of SEQ ID NO: 16, and/or a light chain variable region comprising the amino acid sequence of SEQ ID NO: 20. In certain embodiments, the antibody comprises a heavy chain variable region comprising an HVR-H1 sequence of SEQ ID NO: 7, an HVR-H2 sequence of SEQ ID NO: 8, and an HVR-H3 sequence of SEQ ID NO: 9; and a light chain variable region comprising an HVR-L1 sequence of SEQ ID NO: 11, an HVR-L2 sequence of SEQ ID NO: 14, and an HVR-L3 sequence of SEQ ID NO: 15. In certain embodiments, the antibody comprises a heavy chain variable region comprising the amino acid sequence of SEQ ID NO: 16, and/or a light chain variable region comprising the amino acid sequence of SEQ ID NO: 22.

In other aspects, the present disclosure provides a composition comprising an antibody that specifically binds to an epitope comprising N-acetylglucosamine or N-acetyl-galactosamine and a pharmaceutically acceptable carrier. In other aspects, the present disclosure provides a composition comprising an antibody according to any of the above embodiments and a pharmaceutically acceptable carrier. In further aspects, the present disclosure provides an isolated polynucleotide comprising a nucleic acid sequence encoding an antibody that specifically binds to an epitope comprising N-acetylglucosamine or N-acetyl-galactosamine. In further aspects, the present disclosure provides an isolated polynucleotide comprising a nucleic acid sequence encoding an antibody according to any of the above embodiments. In still further aspects, the present disclosure provides a vector comprising a nucleic acid sequence encoding an antibody that specifically binds to an epitope comprising N-acetylglucosamine or N-acetyl-galactosamine. In still further aspects, the present disclosure provides a vector comprising a nucleic acid sequence encoding an antibody according to any of the above embodiments. In yet still further aspects, the present disclosure provides an isolated host cell comprising a vector comprising a nucleic acid sequence encoding an antibody that specifically binds to an epitope comprising N-acetylglucosamine or N-acetyl-galactosamine. In yet still further aspects, the present disclosure provides an isolated host cell comprising a vector comprising a nucleic acid sequence encoding an antibody according to any of the above embodiments. In yet still further aspects, the present disclosure provides methods of producing an antibody, comprising culturing a host cell comprising a vector comprising a nucleic acid sequence encoding an antibody that specifically binds to an epitope comprising N-acetylglucosamine or N-acetyl-galactosamine, which host cell produces the antibody encoded by the nucleic acid, and recovering the antibody from the cell culture. In yet still further aspects, the present disclosure provides methods of producing an antibody, comprising culturing a host cell comprising a vector comprising a nucleic acid sequence encoding an antibody according to any of the above embodiments, which host cell produces the antibody encoded by the nucleic acid, and recovering the antibody from the cell culture. In yet still further aspects, the present disclosure provides an antibody produced by culturing a host cell comprising a vector comprising a nucleic acid sequence encoding an antibody that specifically binds to an epitope comprising N-acetylglucosamine or N-acetyl-galactosamine, which host cell produces the antibody encoded by the nucleic acid, and recovering the antibody from the cell culture. In yet still further aspects, the present disclosure provides an antibody produced by culturing a host cell comprising a vector comprising a nucleic acid sequence encoding an antibody according to any of the above embodiments, which host cell produces the antibody encoded by the nucleic acid, and recovering the antibody from the cell culture.

In other aspects, the present disclosure provides a method for treating, or preventing, cancer in an individual, comprising administering to the individual an effective amount of a composition comprising an antibody that specifically binds to an epitope comprising N-acetylglucosamine or N-acetyl-galactosamine. In other aspects, the present disclosure provides a method for treating or preventing cancer in an individual, comprising administering to the individual an effective amount of a composition comprising an antibody according to any of the above embodiments. In certain embodiments, the cancer is selected from brain cancer, liver cancer, lung cancer, breast cancer, ovarian cancer, and cervical cancer. In certain embodiments, the individual is a human. In certain embodiments, the individual is a non-human animal.

In other aspects, the present disclosure provides a method for treating or preventing cancer in an individual, comprising administering to the individual an amount of an antibody that specifically binds to an epitope comprising N-acetyl-glucosamine or N-acetyl-galactosamine, and an amount of another anti-cancer agent, where the antibody and the anti-cancer agent in conjunction provide effective treatment or prevention of cancer in the individual. In other aspects, the present disclosure provides a method for treating or preventing cancer in an individual, comprising administering to the individual an amount of an antibody according to any of the above embodiments, and an amount of another anti-cancer agent, where the antibody and the anti-cancer agent in conjunction provide effective treatment or prevention of cancer in the individual. In certain embodiments, the cancer treated is selected from brain cancer, liver cancer, lung cancer, breast cancer, ovarian cancer, cervical cancer, colon cancer, stomach or gastric cancer, esophageal cancer, and fibrosarcoma. In certain embodiments, the individual is a human. In certain embodiments, the individual is a non-human animal. In certain embodiments that may be combined with any of the preceding embodiments, the anti-cancer agent is a chemotherapeutic agent.

In other aspects, the present disclosure provides a method for detecting cancer cells in an individual, comprising contacting a biological sample from the individual with an antibody that specifically binds to an epitope comprising N-acetylglucosamine or N-acetyl-galactosamine and detecting binding of the antibody to the biological sample, where binding of the antibody to the sample may indicate the presence of cancer cells in the individual. In other aspects the present disclosure provides a method for detecting cancer cells in an individual, comprising contacting a biological sample from the individual with an antibody according to any of the above embodiments and detecting binding of the antibody to the biological sample, where binding of the antibody to the sample may indicate the presence of cancer cells in the individual. In certain embodiments, the method further comprises comparing the amount of antibody binding detected with an amount of antibody binding to a control sample. In certain embodiments that may be combined with any of the preceding embodiments, the binding of the antibody to the biological sample is detected by an assay selected from an ELISA assay, a flow cytometry assay, an immunohistochemistry assay, an immunofluorescence assay, a circulating tumor cells assay, and an immune-colloidal gold assay. In certain embodiments that may be combined with any of the preceding embodiments, the biological sample is selected from blood, serum, urine, feces, milk, semen, saliva, chest fluid, abdominal fluid, cerebrospinal fluid, sputum, and any other body fluid or secretion. In certain embodiments, the individual is a human. In certain embodiments, the individual is a non-human animal. In certain embodiments, the antibody comprises a heavy chain variable region comprising, the amino acid sequence of SEQ ID NO:1, and/or a light chain variable region comprising the amino acid sequence of SEQ ID NO:2. In certain embodiments, the antibody comprises a heavy chain variable region comprising an HVR-H1 sequence of SEQ ID NO: 24, an HVR-H2 sequence of SEQ ID NO: 25, and an HVR-H3 sequence of SEQ ID NO: 26; and a light chain variable region comprising HVR-L1 sequence of SEQ ID NO: 27, an HVR-L2 sequence of SEQ ID NO: 28, and an HVR-L3 sequence of SEQ ID NO: 29. In certain embodiments, the antibody comprises a heavy chain variable region comprising the amino acid sequence of SEQ ID NO:3, and/or a light chain variable region comprising the amino acid sequence of SEQ ID NO:4. In certain embodiments, the antibody comprises a heavy chain variable region comprising an HVR-H1 sequence of SEQ ID NO: 7, an sequence SEQ ID NO: 30, and an HVR-H3 sequence of SEQ ID NO: 31; and a light chain variable region comprising an HVR-L1 sequence of SEQ ID NO: 11, an HVR-L2 sequence of SEQ ID NO: 14, and an HVR-L3 sequence of SEQ ID NO: 15. In certain embodiments, the antibody comprises a heavy chain variable region comprising an HVR-H1 sequence of SEQ ID NO: 7, an HVR-H2 sequence of SEQ ID NO: 8, and an HVR-H3 sequence of SEQ ID NO: 9: and a light chain variable region comprising an HVR-L1 sequence of SEQ ID NO: 10, an HVR-L2 sequence of SEQ ID NO: 12, and an HVR-L3 sequence of SEQ ID NO: 15. In certain embodiments, the antibody comprises a heavy chain variable region comprising the amino acid sequence of SEQ ID NO: 16, and/or a light chain variable region comprising the amino acid sequence of SEQ ID NO: 18. In certain embodiments, the antibody comprises a heavy chain variable region comprising an HVR-H1 sequence of SEQ ID NO: 7, an HVR-H2 sequence of SEQ ID NO: 8, and an HVR-H3 sequence of SEQ ID NO: 9; and a light chain variable region comprising an HVR-L1 sequence of SEQ ID NO: 11, an HVR-L2 sequence of SEQ ID NO: 13, and an HVR-L3 sequence of SEQ ID NO: 15. In certain embodiments, the antibody comprises a heavy chain variable region comprising the amino acid sequence of SEQ ID NO: 16, and/or a light chain variable region comprising the amino acid sequence of SEQ ID NO: 20. In certain embodiments, the antibody comprises a heavy chain variable region comprising an HVR-H1 sequence of SEQ ID NO: 7, an HVR-H2 sequence of SEQ ID NO: 8, and an HVR-H3 sequence of SEQ ID NO: 9; and a light chain variable region comprising an HVR-L1 sequence of SEQ ID NO: 11, an HVR-L2 sequence of SEQ ID NO: 14, and an HVR-L3 sequence of SEQ ID NO: 15. In certain embodiments, the antibody comprises a heavy chain variable region comprising the amino acid sequence of SEQ ID NO: 16, and/or a light chain variable region comprising the amino acid sequence of SEQ ID NO: 22. In certain embodiments that may be combined with any of the preceding embodiments, the cancer cells are selected from lung cancer cells, liver cancer cells, breast cancer cells, colon or colorectal cancer cells, esophageal cancer cells, stomach cancer cells, endometrial cancer cells, cervical cancer cells, thyroid cancer cells, brain cancer cells, and lymphoma cells.

In other aspects, the present disclosure provides a method for treating or preventing gastrointestinal disease in an individual comprising administering to the individual an effective amount of an antibody that specifically binds to an epitope comprising N-acetylglucosamine or N-acetyl-galactosamine. In other aspects, the present disclosure provides a method for treating or preventing gastrointestinal disease in an individual comprising administering to the individual an effective amount of an antibody according to any of the above embodiments. In certain embodiments, the individual has inflammatory bowel disease. In certain embodiments, the individual has Crohn's disease. In certain embodiments, the individual has ulcerative colitis. In certain embodiments, the individual has acute infectious gastroenteritis. In certain embodiments, the individual has a hemorrhoid. In certain embodiments, the individual has a gastrointestinal disease caused by a viral infection. In certain embodiments, the viral infection is a rotaviral infection or a porcine epidemic diarrhea viral infection. In certain embodiments, the individual is a human. In certain embodiments, the individual is a non-human animal. In certain embodiments that may be combined with any of the preceding embodiments, the antibody is administered intravenously, intramuscularly, subcutaneously, topically, orally, transdermally, intraperitoneally, intraorbitally, by implantation, by inhalation, intrathecally, intraventricularly, or intranasally.

In other aspects, the present disclosure provides a kit comprising a pharmaceutical composition comprising an antibody that specifically binds to an epitope comprising N-acetylglucosamine or N-acetyl-galactosamine. In other aspects, the present disclosure provides a kit comprising a pharmaceutical composition comprising an antibody according to any of the above embodiments. In certain aspects, the kit further comprises instructions for administering an effective amount of the pharmaceutical composition to an individual for treating or preventing cancer. In certain aspects, the kit further comprises instructions for administering an effective amount of the pharmaceutical composition to an individual for treating or preventing, gastrointestinal disease. In certain aspects, the kit further comprises instructions for detecting the presence of cancer cells in an individual. In certain aspects, the kit further comprises instructions for determining a level of N-acetylglucosamine or N-acetyl-galactosamine in a biological sample from an individual with cancer.

In other aspects, the present disclosure provides a kit comprising a composition comprising N-acetylglucosamine or N-acetyl-galactosamine and instructions or other reagents for using the composition for detecting the presence of an auto-antibody in an individual with cancer or inflammation.

In other aspects, the present disclosure provides a kit comprising a plant lectin, wherein the plant lectin specifically binds to N-acetylglucosamine or N-acetyl-galactosamine, and instructions or other reagents for using the composition for determining a level of N-acetylglucosamine or N-acetyl-galactosamine in a biological sample from an individual with cancer. In some embodiments, the plant lectin is wheat germ agglutinin (WGA) or soybean agglutinin (SBA).

It is to be understood that one, some, or all of the properties of the various embodiments described herein may be combined to form other embodiments of the present invention. These and other aspects of the invention become apparent to one of skill in the art. These and other embodiments of the invention are further described by the detailed description that follows.

BRIEF DESCRIPTION OF THE DRAWINGS

FIG. 3 shows the results of ELISA assays used to screen monoclonal antibodies for binding to N-acetylglucosamine, N-acetyl-galactosamine, and lysates from various cancer cell lines as indicated.

FIG. 4 shows that treatment with monoclonal antibody 2F7H4 inhibits the growth rate of various human cancer cell lines, using an MTT assay for cell growth. Dose of antibody and cell line used for each assay are as labeled. Values refer to the percentage of growth inhibition observed with antibody treatment.

FIG. 5 shows that treatment with monoclonal antibody 1C5C9 inhibits the growth rate of various human cancer cell lines, using an MTT assay for cell growth. Dose of antibody and cell line used for each assay are as labeled. Values refer to the percentage of growth inhibition observed with antibody treatment.

FIG. 6 shows that treatment with monoclonal antibody 3C4F12 inhibits the growth rate of various human cancer cell lines, using an MTT assay for cell growth. Dose of antibody and cell line used for each assay are as labeled. Values refer to the percentage of growth inhibition observed with antibody treatment.

FIG. 11 demonstrates a flow cytometry-based assay for the detection of circulating cancer cells in blood samples from patients with various types of cancer using monoclonal antibody 2F7H4.

FIG. 12 demonstrates a flow cytometry-based assay for the detection of circulating cancer cells in blood samples from patients with various types of cancer using monoclonal antibody 1C5C9.

FIG. 13 demonstrates a flow cytometry-based assay for the detection of circulating cancer cells in blood samples from patients with various types of cancer using monoclonal antibody 1B3E12.

FIG. 14 shows immunofluorescence staining using monoclonal antibody 1C5C9 to stain tissue sections of intestines from mice with inflammation induced by rotavirus infection (B), compared to intestines from healthy mice (A).

DETAILED DESCRIPTION

Figure 1:
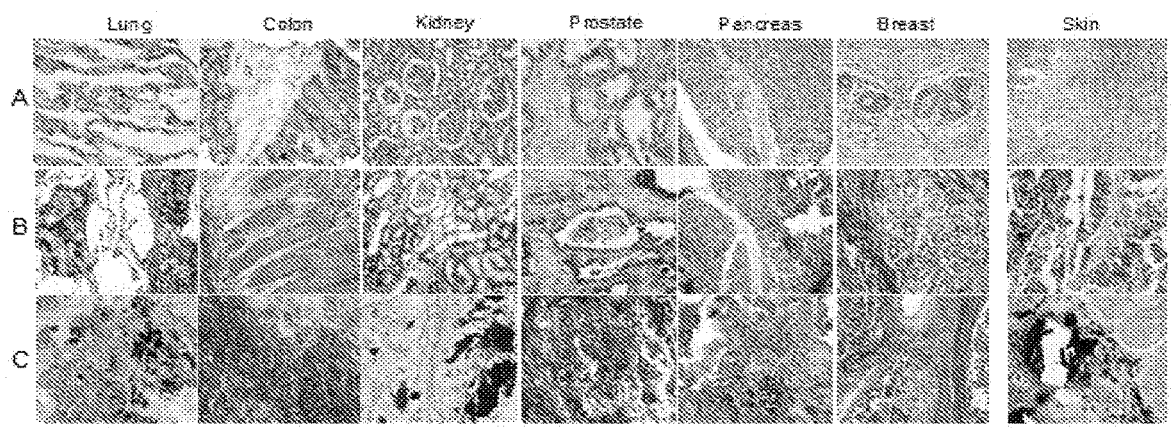
FIG. 1 shows immunohistochemical staining of healthy human tissues (A), human cancer adjacent tissues (B) and human cancer tissues (C) using wheat germ agglutinin, which specifically recognizes N-Acetyl-Glucosamine. The tissue used for each set of samples is as labeled. Human skin malignant melanoma was a positive control for cancerous tissue ("Skin-B"). The tissue panel was recommended by the US FDA.

The inventor of application demonstrated that N-acetylglucosamine and N-acetyl galactosamine are preferentially expressed in many human cancers and cancer cell lines but show little or no expression in most normal human tissues. Further, the inventor generated monoclonal antibodies that recognize N-acetylglucosamine and/or N-acetyl-galactosamine. The results described herein demonstrate that these antibodies are able to bind and inhibit the growth of various human cancer cells. The results described herein also demonstrate that these antibodies may be used to prevent or treat various gastrointestinal diseases. Moreover, the results described herein further show that these antibodies may be used for detection of the saccharide-related biomarkers that are differentially expressed in various cancers and released to blood and other body fluid or secretions.

I. General Techniques

The technique described or referenced herein a well understood and employed using conventional methodology those skilled in the art, such as, for example, the widely, utilized methodologies described in Sambrook et al., *Molecular Cloning: A Laboratory Manual* 3d edition (2001) Cold Spring Harbor Laboratory Press, Cold Spring Harbor, N.Y.; *Current Protocols in Molecular Biology* (F. M. Ausubel, et al. eds., (2003)); Harlow and Lane, eds. (1988) *Antibodies, A Laboratory Manual, and Animal Cell Culture* (R. I. Freshney ed. (1987)). *Methods in Molecular Biology*, Humana Press; *Monoclonal Antibodies: A Practical Approach* (P. Shepherd and C. Dean, eds., Oxford University Press, 2000), and *Cancer: Principles and Practice of Oncology* (V. T. DeVita et al. eds., J. B. Lippincott Company, 1993).

II. Definitions

Before describing the invention in detail, it is to be understood that this invention is not limited to particular compositions or biological systems, which can of course, vary. It is also to be understood that the terminology used herein is for the purpose of describing particular embodiments only, and is not intended to be limiting.

As used in this specification and the appended claims, the singular forms "a", "an" and "the" include plural referents unless the content clearly dictates otherwise. Thus, for example, reference to "a molecule" optionally includes a combination of two or more such molecules, and the like.

The term "about" as used herein refers to the usual error range for the respective value readily known to the skilled person in this technical field. Reference to "about" a value or parameter herein includes (and describes) embodiments that are directed to that value or parameter per se.

It is understood that aspects and embodiments of the invention described herein include "comprising," "consisting," and "consisting essentially of" aspects and embodiments.

The term "inflammation" refers to the complex biological response of body tissues to harmful stimuli, such as pathogens, damaged cells, or irritants. The classical signs of acute inflammation include without limitation pain, heat, redness, swelling, and loss of function. Inflammation is a generic response, and therefore it is considered a mechanism of innate immunity. Inflammation can be classified as acute or chronic. Acute inflammation refers to the initial response of the body to harmful stimuli and is achieved by the increased movement of plasma and leukocytes (specially granulocytes) from the blood into the injured tissues. A series of biochemical events propagates and matures the inflammatory response, involving the local vascular system, the immune system, and various cells within the injured tissue. Prolonged inflammation, known as chronic inflammation, leads to a progressive shift in the type of cells present at the site of inflammation and is characterized by simultaneous destruction and healing of the tissue from the inflammatory process.

The term "inflammatory cells" refers to leukocytes neutrophils, macrophages, monocytes, eosinophils, and basophils) that normally reside in the blood and move into the inflamed tissue via extravasation to aid in inflammation. Some act as phagocytes, ingesting bacteria, viruses, and cellular debris. Others release enzymatic granules that damage pathogenic invaders. Leukocytes also release inflammatory mediators that: develop and maintain the inflammatory response. In general, acute inflammation is mediated by granulocytes, whereas chronic inflammation is mediated by mononuclear cells such as monocytes and lymphocytes.

The term "inflammatory bowel disease (IBD)" refers to the pathological state characterized by chronic inflammation of all or part of digestive tract. IBD primarily includes ulcerative colitis and Crohn's disease. Both usually involve severe diarrhea, pain, fatigue, and weight loss. Ulcerative colitis is a form of IBD that causes long-lasting inflammation and sores (ulcers) in large intestine (colon) and rectum. Crohn's disease is a form of IBD that causes inflammation of the digestive tract. In Crohn's disease, inflammation often spreads deep into affected tissues. The inflammation can involve different areas of the digestive tract such as the large intestine, small intestine or both. Collagenous colitis and lymphocytic colitis also are considered inflammatory bowel diseases but are usually regarded separately from classic inflammatory bowel disease.

The terms "cancer" and "cancer cells" refer to or describe the physiological condition in animals that is typically characterized by unregulated cell growth. Examples of cancers include, but, are not limited to, lung cancer including small cell lung cancer, adenocarcinoma of the lung and squamous carcinoma of the lung, hepatocellular cancer, brain cancer including malignant oligodendroglioma, glioblastoma of glioma, gastrointestinal cancer including but not limited to esophageal cancer, gastric cancer, intestinal cancer, colon cancer and colorectal cancer, kidney clear cell carcinoma, skin basal cell carcinoma, skin squamous cell carcinoma, throat carcinoma, Hodgkin's lymphoma, thyroid medullary carcinoma, pancreatic cancer, cervical cancer, ovarian cancer, bladder cancer, cancer of the urinary tract, breast cancer, endometrial or uterine carcinoma, salivary gland carcinoma, prostate cancer, melanoma, multiple myeloma and B-cell lymphoma, leukemias, and associated metastases. In some embodiments, the type of cancer is selected from: brain cancer, liver cancer, lung cancer, breast cancer, ovarian cancer, and cervical cancer. In some embodiments, the cancer cell is selected from: a glioma cell, a hepatocarinoma cell, a lung cancer cell, a breast cancer cell, an ovarian carcinoma cell, and a cervical adenocarcinoma cell.

The term "immunoglobulin" (Ig) is used interchangeably with "antibody" herein. The term "antibody" herein is used in the broadest sense and specifically covers monoclonal antibodies, polyclonal antibodies multispecific, antibodies (e.g., bispecific antibodies) formed from at least two intact antibodies and antibody fragments (e.g., a Fab fragment, scFv, minibody, diabody, scFv multimer, or bispecific antibody fragment) so long as they exhibit the desired biological activity.

As used herein, the term "specifically binds to" or is "specific for" refers to measurable and reproducible interactions such as binding between a target and an antibody, that is determinative of the presence of the target in the presence of a heterogeneous population of molecules including biological molecules. For example, an antibody that specifically binds to a target (which can be an epitope) is an antibody that binds this target with greater affinity, avidity, more readily and/or with greater duration than it binds to other targets. In certain embodiments, an antibody that specifically binds to a target has a dissociation constant (Kd) of ≤1 µM, ≤100 nM, ≤10 nM, ≤1 nM, or ≤0.1 nM. In another embodiment, specific binding can include, but does not require exclusive binding.

The "variable region" or "variable domain" or an antibody refers to the amino-terminal domains of the heavy or light chain of the antibody. The variable domains of the heavy chain and light chain may be referred to as "$V_H$" and "$V_L$" respectively. These domains are generally the most variable parts of the antibody (relative to other antibodies of the same class) and contain the antigen binding sites.

The term "variable" refers to the fact that certain segments of the variable domains differ extensively in sequence among antibodies. The V domain mediates antigen binding and defines the specificity of a particular antibody for its particular antigen. However, the variability is not evenly distributed across the entire span of the variable domains. Instead, it is concentrated in three segments called "hypervariable regions (HVRs)" both in the light-chain and the heavy chain variable domains (for a total of 6 HVRs per antibody or antigen-binding fragment thereof). As used herein, a "hypervariable region (HVR)" contains highly variable sequence that confers specific antigen-binding to an antibody. The more highly conserved portions of variable domains are called the framework regions (FR). The HVRs in each chain are held together in close proximity by the FR regions and, with the HVRs from the other chain, contribute to the formation of the antigen binding site of antibodies (see Kabat et al., *Sequences of Immunological Interest*, Fifth Edition, National institute of Health, Bethesda, Md. (1991)). The constant domains are not involved directly in the binding of antibody to an antigen, but exhibit various effector functions, such as participation of the antibody in antibody-dependent-cellular toxicity.

A number of HVR delineations are in use and are encompassed herein. The Kabat Complementarily Determining Regions (CDRs) are based on sequence variability and are the most commonly used (Kabat et al., *Sequences of Proteins of immunological Interest*, 5th Ed. Public Health Service, National institutes of Health, Bethesda, Md. (1991)). Chothia refers instead to the location of the structural loops (Chothia and Lesk *J. Mol. Biol.* 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. The residues from each of these HVRs are rioted below.

| Loop | Kabat | AbM | Chothia | Contact |
|------|-------|-----|---------|---------|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B (Kabat Numbering) |
| H1 | H31-H35 | H26-H35 | H26-H32 | H30-H35 (Chothia Numbering) |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2) and 89-97 or 89-96 (L3) in the VL and 26-35 (H1), 50-65 or 49-65 (H2) and 93-102, 94-102, or 95-102 (H3) in the VH. The variable domain residues are numbered according to Kabat et al., supra, for each of these definitions.

The term "monoclonal antibody" as used herein refers to an antibody obtained from a population of substantially homogeneous antibodies, i.e., the individual antibodies comprising the population are identical except for possible naturally occurring mutations and/or post-translation modifications (e.g., isomerizations, amidations) that may be present in minor amounts. Monoclonal antibodies are highly specific, being directed against a single antigenic site. In contrast to polyclonal antibody preparations which typically include different antibodies directed against different determinants (epitopes), each monoclonal antibody is directed against a single determinant on the antigen.

The modifier "monoclonal" indicates the character of the antibody as being obtained from a substantially homogeneous population of antibodies, and is not to be construed as requiring: production of the antibody by any particular method. For example, the monoclonal antibodies to be used in accordance with the present invention may be made by a variety of techniques, including, for example the hybridoma method (e.g., Kohler and Milstein., *Nature*, 256:495-97 (1975), recombinant DNA methods (see, e.g., U.S. Pat. No. 4,816,567); phage-display technologies (see, e.g., Clarkson et al., *Nature*, 352:624-628 (1991)); and technologies for producing human or human-like antibodies in animals that have parts or all of the human immunoglobulin loci or genes encoding human immunoglobulin sequences (see, e.g., Jakobovits et al., *Proc. Nat'l Acad. Sci. USA*, 90:2551 (1993); Lonberg et al., *Nature* 3681856-859 (1994)).

An "antibody fragment" comprises a portion of an intact antibody, preferably the antigen binding and/or the variable region of the intact antibody. Examples of antibody fragments include Fab, Fab', F(ab')$_2$ and Fv fragments; minibodies; diabodies; scFvs; scFv multimers; linear antibodies; single-chain antibody molecules; and bispecific or multispecific antibodies formed from antibody fragments.

"Single-chain Fv" also abbreviated as "sFv" or "scFv" are antibody fragments that comprise the VH and VL antibody domains connected into a single polypeptide chain. Preferably, the scFv polypeptide further comprises a polypeptide linker between the $V_H$ and $V_L$ domains which enables the scFv to form the desired structure for antigen binding. For a review of the scFv, see Pluckthun in *The Pharmacology of Monoclonal Antibodies*, vol. 113, Rosenburg and Moore eds., Springer-Verlag, New York, pp. 269-315 (1994).

The term "diabodies" refers to small antibody fragments prepared by constructing scFv fragments (see preceding paragraph) with short linkers (about 5-10) residues) between the $V_H$ and $V_L$ domains such that inter-chain but not intra-chain pairing of the V domains is achieved, thereby resulting in a bivalent fragment, i.e., a fragment having two antigen-binding sites. Diabodies are described in greater detail in, for example, EP 404,097; WO 93/11161; Hollinger et al., *Proc. Nat'l Acad. Sci. USA*, 90:6444-48 (1993).

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is(are) identical with or homologous to corresponding sequences in antibodies derived from another species or belonging to another antibody class or subclass, as well as fragments of such antibodies, so long as they exhibit the desired biological activity U.S. Pat. No. 4,816,567; Morrison et al., *Proc. Nat'l Acad. Sci. USA*, 81:6851-55 (1984)).

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from an HVR of the recipient are replaced by residues from an HVR of a non-human species (donor antibody) such as mouse, rat, rabbit or non-human primate having the desired specificity, affinity, and/or capacity. For further details, see, e.g., Jones et al., *Nature* 321:522-525 (1986).

A "human antibody" is one that possesses an amino-acid sequence corresponding to that of art antibody produced by a human and/or has been made using any of the techniques for making human antibodies as disclosed herein. Human antibodies can be produced using various techniques known in the art, such as the methods described in Cole et al., *Monoclonal Antibodies and Cancer Therapy*, Alan R. Liss, p. 77 (1985); Boerner et al., *J. Immunol.* 147(1):86-95 (1991).

An "isolated" antibody is one that has been identified, separated and/or recovered from a component of its production environment (e.g., naturally or recombinantly). Preferably, the isolated polypeptide is free of contaminant components that would typically interfere with uses for the antibody, e.g., enzymes, hormones, and other proteinaceous or non-proteinaceous solutes.

As used herein, the term "treatment" refers to clinical intervention designed to alter the natural course of the individual or cell being treated during the course of clinical pathology. Desirable effects of treatment include decreasing the rate of disease progression, ameliorating or palliating the disease state, and remission or improved prognosis. An individual is successfully "treated", for example, if one or more symptoms associated with cancer are mitigated or eliminated.

As used herein, the term "prevention" includes providing, prophylaxis with respect to occurrence or recurrence of a disease in an individual. An individual may be predisposed to, susceptible to a type of cancer, or at risk of developing a type of cancer, but has not yet been diagnosed with the disease.

An "effective amount" refers to at least an amount effective, at dosages and for periods of time necessary, to achieve the desired therapeutic or prophylactic result. An effective amount can be provided in one or more administrations.

A "therapeutically effective amount" is at least the minimum concentration required to effect a measurable improvement of a particular disorder (e.g., cancer). A therapeutically effective amount herein may vary according to factors such as the disease state, age, sex, and weight of the patient, and the ability of the monoclonal antibody to elicit a desired response in the individual. A therapeutically effective amount is also one in which any toxic or detrimental effects of the monoclonal antibody are outweighed by the therapeutically beneficial effects. A "prophylactically effective amount" refers to an amount effective, at the dosages and for periods of time necessary, to achieve the desired prophylactic result. Typically but not necessarily, since a prophylactic dose is used in subjects prior to or at an earlier stage of disease, a prophylactically effective amount may be less than a therapeutically effective amount.

As used herein, administration "in conjunction" with another compound or composition includes simultaneous administration and/or administration at different times. Administration in conjunction also encompasses administration as a co-formulation or administration as separate compositions, including at different dosing frequencies or intervals, and using the same route of administration or different routes of administration.

An "individual" for purposes of treatment or prevention refers to any animal classified as a mammal, including humans, domestic and farm animals, and zoo, sport, or pet animals, such as dogs, horses, rabbits, cattle, pigs, hamsters, gerbils, mice, ferrets, rats, cats, and the like. In some embodiments the individual is human. In some embodiments, the individual is a non-human animal.

"Carriers" as used herein include pharmaceutically acceptable carriers, excipients, or stabilizers that are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; low molecular weight (less than about 10 residues) polypeptide; proteins, such as serum albumin, gelatin, or immunoglobulins; amino acids such as glycine, glutamine, asparagine, arginine or lysine, carbohydrates including glucose, mannose, or dextrins; and/or nonionic surfactants such as TWEEN™, polyethylene glycol (PEG), and PLURONICS™.

"Pharmaceutically acceptable" buffers and salts include those derived from both acid and base addition salts of the above indicated acids and bases. Specific buffers and/or salts include histidine, succinate and acetate.

"Polynucleotide," or "nucleic actor," as used interchangeably herein, refer to polymers of nucleotides of any length, and include DNA and RNA. The nucleotides can be deoxyribonucleotides, ribonucleotides, modified nucleotides or bases and/or their analogs, or any substrate that can be incorporated into a polymer by DNA or RNA polymerase or by a synthetic reaction.

An "isolated" polynucleotide encoding the antibodies herein is a nucleic acid molecule that: is identified and separated from at least one contaminant nucleic acid molecule with which it is ordinarily associated in the environment in which it was produced. The isolated nucleic acid molecules encoding the polypeptides and antibodies herein are in a form other than in the form or setting in which it is found in nature. Preferably, the isolated nucleic acid is free of association with all components associated with the production environment.

The term "vector," as used herein, is intended to refer to a nucleic acid molecule capable of transporting another nucleic acid to which it has been linked. Types of vectors include plasmids (i.e., circular double stranded DNA into which additional DNA segments may be ligated) and viral vectors. Certain vectors are capable of autonomous replication in a host cell into which they are introduced (e.g., bacterial vectors having a bacterial origin of replication and episomal mammalian vectors). Other vectors can be integrated into the genome of a host cell and replicated along with the host genome. Moreover, certain vectors are capable of directing the expression of genes to which they are operatively linked. Such vectors are referred to herein as "recombinant expression vectors," or simply, "expression vectors." In the present specification, "plasmid" and "vector" may be used interchangeably as the plasmid is the most commonly used form of vector.

III. Saccharides

Certain aspects of the present disclosure are related to epitopes containing saccharides. As used herein, a "saccharide" may refer to a monosaccharide, an oligosaccharide or a polysaccharide. Monosaccharides include but not limited to fructose, glucose, mannose, fucose, xylose, galactose, lactose, N-acetylglucosamine acid N-acetyl-galactosamine, N-acetylglucosamine and sialic acids. An oligosaccharide is a saccharide polymer containing multiple sugar monomers linked by glycosidic linkages of component sugars.

Glycoproteins or proteosaccharides refer to proteins linked with saccharides and may typically contain, for example, O- or N-glycosidic linkages of monosaccharides to compatible amino acid side chains in proteins or to lipid moieties. As used herein, the terms "glycan" and "glycosyl moiety" may be used interchangeably to refer to a saccharide alone or a sugar as the saccharide component of a glycoprotein. Two types of glycosylation are known in the art. N-linked glycosylation to the amide nitrogen of asparagine side chains and O-linked glycosylation to the hydroxy oxygen of serine and threonine side chains, Other saccharides include but not limited to O-GlcNAc, GAG Chain, glycosaminosaccharides, and glycosphinglipid. O- and N-linked saccharides are very common in eukaryotes but may also be found, although less commonly, in prokaryotes.

Certain aspects of the present disclosure relate to N-acetylglucosamine and N-acetyl-galactosamine. N-acetylglucosamine may refer to any amino sugar compound that includes an N-linked glucosamine moiety. As used herein, N-acetylglucosamine may refer to the monosaccharide on its own, or the monosaccharide as a component of a larger polysaccharide. As used herein, N-acetylglucosamine may refer to a saccharide entity on its own, or the saccharide as the glycan component of a glycoprotein or protein glycosylated with one or more N-acetylglucosamine-based components (e.g., mono- or poly-saccharides that contain N-acetylglucosamine).

N-acetyl-galactosamine may refer to any compound that includes glucosamine N-linked to an acetic acid moiety. N-acetyl-galactosamine may refer to any amino sugar compound that includes an N-linked galactosamine moiety. As used herein, N-acetyl-galactosamine may refer to the monosaccharide on its own, or the monosaccharide as a component of a larger polysaccharide. As used herein, N-acetyl-galactosamine may refer to a saccharide entity on its own, or the saccharide as the glycan component of a glycoprotein or protein glycosylated with one or more N-acetyl-galactosamine moieties (e.g., mono- or poly-saccharides that contain N-acetyl-galactosamine).

While many proteins are known to be glycosylated glycoproteins are often found on the exterior surface of cells (i.e., extracellular) or secreted. Because of this, glycoproteins are highly accessible to external agents (e.g., exogenous compounds administered to a patient). For example, components that specifically recognize certain glycoproteins (e.g., antibodies or lectins are able to bind, in an intact organism, to cells that express these glycoproteins on their cell surface. Components that specifically recognize certain glycoproteins are also able to bind secreted saccharides or glycoproteins, for example those that may be found freely in certain tissue samples (including, without limitation, in blood or serum).

Lectins are known in the art as sugar-binding proteins which are able to recognize cognate sugar moieties with high specificity. These highly specific binding interactions may be exploited, for example, for the detection of specific saccharides in tissues (e.g., for the detection of cell surface proteins modified by glycosylation with specific sugar moieties). Lectins may include, for example, animal lectins, plant lectins, and pathogen lectins. In mammals, lectins are known to play important roles in the immune system by, e.g., recognizing carbohydrates that are found exclusively on pathogens, or that are inaccessible on host cells.

Certain aspects of the present disclosure use plant lectins to detect the presence or expression of specific sugar moieties. For example, plant lectins may include but not limited to lectins specific to fructose, mannose glucose, fucose, galactose, N-acetyl-galactosamine and N-acetyl-glucosamine.

IV. Antibodies

Epitope Binding

Certain aspects of the present disclosure relate to antibodies that specifically bind to an epitope containing N-acetylglucosamine or N-acetyl-galactosamine. As described above, such antibodies will display measurable and reproducible interactions such as binding to an epitope containing N-acetylglucosamine or N-acetyl-galactosamine. For example, an antibody that specifically binds to an epitope is an antibody that binds this epitope with greater affinity, avidity, more readily, and/or with greater duration than it binds to other targets. Examples of epitopes containing N-acetylglucosamine or N-acetyl-galactosamine include glycoproteins containing N-acetylglucosamine or N-acetyl-galactosamine glycans, for example and without limitation cell surface glycoproteins bearing an N-acetylglucosamine or N-acetyl-galactosamine moiety expressed on the surface of a cancer cell.

Specific binding can include, but does not require exclusive binding. While antibodies that specifically bind to an epitope containing N-acetylglucosamine or N-acetyl-galactosamine, they may also be found to bind to other epitopes not containing these moieties, e.g., with a lesser binding affinity than epitopes containing N-acetylglucosamine or N-acetyl-galactosamine.

In some embodiments, antibodies specifically bind to epitopes containing N-acetylglucosamine and N-acetylglucosamine. For example, an antibody may be capable of specific binding to an epitope containing N-acetylglucosamine and to an epitope containing N-acetyl-galactosamine In some embodiments, an antibody may be capable of specific binding to an epitope containing both N-acetylglucosamine and N-acetyl-galactosamine.

In some embodiments, the binding of the antibody to the epitope containing N-acetylglucosamine and/or N-acetylgalactosamine expressed on the cell surface of the cancer cell inhibits growth of the cancer cell. As used herein, inhibiting the growth of a cell may refer to inhibition its rate of proliferation. Without wishing to be bound to theory, through binding to the cell surface, antibodies may inhibit the growth of cells by a variety of mechanisms. For example, antibody binding to the cell surface may be toxic to the cell or otherwise cause cell death, for example and without limitation, apoptosis or necrosis. Antibody binding to the cell surface may slow or stop cell proliferation. Antibody binding to the cell surface glycoprotein on the cell surface may inhibit or enhance a function of the glycoprotein, for example a cell signaling function, and in so doing the antibody binding may inhibit the growth of the cell. Antibody binding to the cell surface may compete with an extrinsic ligand that accelerates the growth of the cell through binding to the cell surface, for example a growth factor. This companion may be indirect, i.e., the antibody need not competitively bind an epitope on the same glycoprotein as the extrinsic ligand. Antibody binding to the cell surface may also attract one or more components of the immune system, such as natural killer or NK cells, that inhibit the growth of antibody-bound cells. The mechanism(s) by which different antibodies inhibit the growth of cells through binding epitopes on the cell surface may be different depending on the cellular context or the specific antibody or epitope.

Antibody Features

Certain antibodies that specifically bind to an epitope containing N-acetylglucosamine or N-acetyl-galactosamine are described and characterized in the present disclosure. In some embodiments, the antibody is 2F7H4. In some embodiments, the antibody comprises a heavy chain variable region including three HVRs from the amino acid sequence of SEQ NO:1, and a light chain variable region including three HVRs from the amino acid sequence of SEQ ID NO:2. In some embodiments, the heavy chain variable region includes an HVR1 comprising the sequence FTFSDFYME (SEQ ID NO: 24), an HVR2 comprising the sequence ASRNKANDYTTEYSASVKG (SEQ ID NO: 25), and an HVR3 comprising the sequence DAWFA (SEQ ID NO: 26). In some embodiments, the light chain variable region includes an HVR1 comprising the sequence KSSQSLLLYSSNQKNYLA (SEQ ID NO: 27), an HVR2 comprising the sequence WASTRES (SEQ ID NO: 28), and an HVR3 comprising the sequence QQYYSYPR (SEQ ID NO: 29).

In some embodiments, the antibody is 1C5C9. In some embodiments, the antibody contains a heavy chain variable region including three HVRs from the amino acid sequence of SEQ NO:3, and a light chain variable region including three HVRs from the amino acid sequence of SEQ ID NO:4. In some embodiments, the heavy chain variable region includes an HVR1 comprising the sequence YTFPDYNIH (SEQ ID NO: 7), an HVR2 comprising, the sequence CIYPYNGNTAYNQKFKT (SEQ ID NO: 30), and an HVR3 comprising the sequence SDLYYFGSRGFV (SEQ ID NO: 31). In some embodiments, the light chain variable region includes an HVR1 comprising the sequence RASQDISTYLN (SEQ ID NO: 11), an HVR2 comprising the sequence FTSRLHS (SEQ ID NO: 14) and an HVR3 comprising the sequence QQGNTLPW (SEQ ID NO: 15).

In some embodiments, the antibody is a humanized form of antibody 1C5C9. In some embodiments, the antibody is humanized 1C5-VK1. In some embodiments, the antibody comprises a heavy chain variable region comprising an HVR-H1 sequence of YTFPDYNIH (SEQ ID NO: 7), an HVR-H2 sequence of CIYPYNGNTA (SEQ ID NO: 8), and an sequence of SDLYYFGSRGFD (SEQ ID NO: 9). In some embodiments, the antibody comprises a light chain variable region comprising an HVR-L1 sequence of QASQDISTYLN (SEQ ID NO: 10), an HVR-L2 sequence of FTSNLET (SEQ ID NO: 12), and an II VR-L3 sequence of QQGNTLPW (SEQ ID NO: 15).

In some embodiments, the antibody comprises a heavy chain variable region comprising the amino acid sequence of QVQLVQSGAEVKKPGASVKVSCKASGYTFPDYNIHWVRQAPGQGLEWMGCTYPYNGNTAYAQKFQGRVTMTRDTSISTAYMELSRLRSDDTAVYYCARSDLYYFGSRGFDYWQ GTLVTVASSA (SEQ ID NO: 16), and/or a light chain variable region comprising the amino acid sequence of

```
                                      (SEQ ID NO: 18)
DIQMTQSPSSLSASVGDRVTITCQASQDISTYLNWYQQKPGKAPKLL

IYFTSNLETGVPSRFSGSGSGTDFTLTISSLQPEDIATYYCQQGNTL

PWTFGGGTKLE.
```

In some embodiments, the antibody comprises a heavy chain comprising the amino acid sequence of QVQLVQSGAEVKKPGASVKVSCKASGYTFPDYNIHWVRQAPGQGLEWMGCIYPYNCNTAYAQKFQGRVTMTRDTSISTAYMELSRLRSDDTAVYYCARSDLYYFGSRGFDYWGQ GTLVTVSSASTKGPSVFPLAPSSKSTSGGTAALGCLVKDYFPEPVTVSWNSGALTSGVHTFPVLQSSGLYSLSSVVTYPSSSLGTQTYICNVNHKPSNTKVDKRVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQ VYTLPPSRDELTKNQVSLTCLVKGFYPSDIAVEWESNGQPENNYKTTPPVLDSDG SFFLY SKLTVDKSRWQQGNVESCSVMHEALHNHYTQKSLSLSPGK (SEQ ID NO: 17), and/or a light chain comprising the amino acid sequence of

```
                                      (SEQ ID NO: 19)
DIQMTQSPSSLSASVGDRVTITCQASQDISTYLNWYQQKPGKAPKLL

IYFTSNLETGVPSRFSGSGSGTDFTLTISSLQPEDIATYYCQQGNTL

PWTFGGGTKLERTVAAPSVFIFPPSDEQLKSGTASVVCLLNNFYPRE

AKVQWKVDNALQSGNSQESVTEQDSKDSTYSLSSTLTLSKADYEKHK

VYACEVTHQGLSSPVTKSFNRGEC.
```

In some embodiments, the antibody is humanized 1C5-VK2. In some embodiments, the antibody comprises a heavy chain variable region comprising an HVR-H1 sequence of YTFPDYNIH (SEQ ID NO: 7), an HVR-H2 sequence of CIYPYNGNTA (SEQ ID NO: 8), and an HVR-H3 sequence of SDLYYFGSRGFD (SEQ ID NO: 9). In some embodiments, the antibody comprises a light chain variable region comprising an HVR-L1 sequence of RASQDISTYLN (SEQ ID NO: 11), an HVR-L2 sequence of FTSSLQS (SEQ ID NO: 13), and an HVR-L3 sequence of QQGNTLPW (SEQ ID NO: 15).

In some embodiments, the antibody comprises a heavy chain variable region comprising the amino acid sequence of QVQLVQSGAEVKKPGASVKVSCKASGYTFP-DYNIHWVRQAPGQGLEWMGCIYPYNGN TAYAQKFQGRVTMTRDTSISTAYMELSRLRSDD-TAVYYCARSDLYYGSRGFDYWGQ GTLVTVSSA (SEQ ID NO: 16), and or a light chain variable region comprising the amino acid sequence of (SEQ ID NO: 20)
DIQMTQSPSSLSASVGDRVTITCRASQDISTYLNWYQQKPGKAPKLL

IYFTSSLQSGVPSRFSGSGSGTDFTLTISSLQPEDIATYYCQQGNTL

PWTFGGGTKLE.

In some embodiments, the antibody comprises a heavy chain comprising the amino acid sequence of QVQLVQS-GAEVKKPGASVKVSCKASGYTFP-DYNIHWVRQAPGQQLEWMGCIYYPYNGN TAYAQKFQGRVTMTRDTSISTAYMELSRLRSDD-TAVYYCARSDLYYFGSRGFDYWGQ GTLVTVSSAS-TKGPSVFPLAPSSKSTSGGTAALGCLVKDYF-PEPVTVSWNSGALTSGVHT FPAVLQSSGLYS-LSSVVTVPSSSLGTQTYICNVNHKPSNTKVDKRVE-PKSCDKTHTCPPC PAPELLGGPSVFLFPPKPKDTLMISRTPE-VTCVVVDVSHEDPEVKFNWYVDGVEVHNAK TKPREEQYN-STYRVVSLVLTVLHQDWLNGKEYKCKVSNKALPA-PIEKTISKAKGQPREPQ VYTLPPSRDELTKNQVSLT-CLVKGFYPSDIAVEWESNGQPENNYKTTPPVLDSDG SFFLY SKLTVDKSRWQQGNVFSCSVMHEALHN-HYTQKSLSLSPGK (SEQ ID NO: 17), and/or a light chain comprising the amino acid sequence of (SEQ ID NO: 21)
DIQMTQSPSSLSASVGDRVTITCRASQDISTYLNWYQQKPGKAPKLL

IYFTSSLQSGVPSRFSGSGSGTDFTLTISSLQPEDIATYYCQQGNTL

PWTFGGGTKLERTVAAPSVFIFPPSDEQLKSGTASVVCLLNNFYPRE

AKVQWKVDNALQSGNSQESVTEQDSKDSTYSLSSTLTLSKADYEKHK

VYACEVTHQGLSSPVTKSFNRGEC.

In some embodiments, the antibody comprises a heavy chain variable region comprising the amino acid sequence of: QVQLVQSGAEVKKPGASVKVSCKASGYTFP-DYNIHWVRQAPGQQLEWMGCIYYPYNGN TAYAQKFQGRVTMTRDTSISTAYMELSRLRSDD-TAVYYCARSDLYYFGSRGFDYWGQ GTLVTVSSA (SEQ ID NO: 16), and/or a light chain variable region comprising the amino acid sequence of (SEQ ID NO: 22)
DIQMTQSPSSLSASVGDRVTITCRASQDISTYLNWYQQKPGKAPKLL

IYFTSRLHSGVPSRFSGSGSGTDFTLTISSLQPEDIATYYCQQGNTL

PWTFGGGTKLE.

In some embodiments, the antibody comprises a heavy chain comprising the amino acid sequence of QVQLVQS-GAEVKKPGASVKVSCKASGYTFP-DYNIHWVRQAPGQQLEWMGCIYYPYNGN TAYAQKFQGRVTMTRDTSISTAYMELSRLRSDD-TAVYYCARSDLYYFGSRGFDYWGQ GTLVTVSSAS-TKGPSVFPLAPSSKSTSGGTAALGCLVKDYF-PEPVTVSWNSGALTSGVHT FPAVLQSSGLYS-LSSVVTVPSSSLGTQTYICNVNHKPSNTKVDKRVE-PKSCDKTHTCPPC PAPELLGGPSVFLFPPKPKDTLMISRTPE-VTCVVVDVSHEDPEVKFNWYVDGVEVHNAK TKPREEQYN-STYRVVSLVLTVLHQDWLNGKEYKCKVSNKALPA-PIEKTISKAKGQPREPQ VYTLPPSRDELTKNQVSLT-CLVKGFYPSDIAVEWESNGQPENNYKTTPPVLDSDG SFFLY SKLTVDKSRWQQGNVFSCSVMHEALHN-HYTQKSLSLSPGK (SEQ ID NO: 17), and/or a light chain comprising the amino acid sequence of:

(SEQ ID NO: 23)
DIQMTQSPSSLSASVGDRVTITCRASQDISTYLNWYQQKPGKAPKLL

IYFTSRLHSGVPSRFSGSGSGTDFTLTISSLQPEDIATYYCQQGNTL

PWTFGGGTKLERTVAAPSVFIFPPSDEQLKSGTASVVCLLNNFYPRE

AKVQWKVDNALQSGNSQESVTEQDSKDSTYSLSSTLTLSKADYEKHK

VYACEVTHQGLSSPVTKSFNRGEC.

In some embodiments, the antibody is humanized 1C5-VKW. In some embodiments, the antibody comprises a heavy chain variable region comprising an HVR-H1 sequence of YTFPDYNIH (SEQ ID NO: 7), an HVR-H2 sequence of CIYPYNGNTA (SEQ ID NO: 8), and an HVR-H3 sequence of SDLYYFGSRGFD (SEQ ID NO: 9). In some embodiments, the antibody comprises a light chain variable region comprising an HVR-L1 sequence of RASQDISTYLN (SEQ ID NO: 11), an HVR-L2 sequence of FTSRLHS (SEQ ID NO: 14), and an HVR-L3 sequence of QQGNTLPW SEQ ID NO: 15).

In some embodiments, the antibody is 3C4F12. In some embodiments, the antibody contains a heavy chain variable region including three HVRs from the amino acid sequence of SEQ ID NO:5, and a light chain variable region including three HVRs from the amino acid sequence of SEQ ID NO:6. In some embodiments, the heavy chain variable region includes an HVR1 comprising the sequence FAFSSYDMS (SEQ ID NO: 32), an HVR2 comprising the sequence YISSGGGSTYYPDTVKG (SEQ ID NO: 33), and an HVR3 comprising the sequence RYYYGSSWAMD (SEQ ID NO: 34). In some embodiments, the light chain variable region includes an HVR1 comprising the sequence KASQSVSNDVA (SEQ ID NO: 35), an HVR2 comprising the sequence YASNRYT (SEQ ID NO: 36), and an HVR3 comprising the sequence QQDYSSPY (SEQ ID NO: 37). In some embodiments, the antibody is 1B3E12.

The antibodies useful in the present invention can encompass monoclonal antibodies, polyclonal antibodies, antibody fragments (e.g., Fab, Fab'-SH, Fv, scFv, and F(ab")$_2$), chimeric antibodies, bispecific antibodies, multivalent antibodies, heteroconjugate antibodies, fusion proteins comprising an antibody portion, humanized antibodies, and any other modified configuration of the immunoglobulin molecule that comprises an antigen recognition site of the required specificity (e.g., for epitope containing N-acetylglucosamine or N-acetyl-galactosamine), including glycosylation variants of antibodies, amino acid sequence variants of antibodies, and covalently modified antibodies. The antibodies may be murine, rat, human, or of any other origin (including chimeric or humanized antibodies).

In some embodiments, the antibody that specifically binds to an epitope containing N-acetylglucosamine or N-acetyl-galactosamine is a monoclonal antibody. For example, the monoclonal antibodies may be made using the hybridoma method first described by Kohler et al., *Nature*, 256:495 (1975), or may be made by recombinant DNA methods (U.S. Pat. No. 4,816,567).

Culture medium in which hybridoma cells are growing is assayed for production of monoclonal antibodies directed against the antigen (e.g., an epitope containing N-acetylglucosamine or N-acetyl-galactosamine). Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA).

Monoclonal antibodies may also be made by recombinant DNA methods, such as those described above. DNA encoding the monoclonal antibodies is readily isolated and sequenced using conventional procedures, placed into expression vectors, and transfected into host cells such as *E. coli* cells or CHO cells to produce recombinant monoclonal antibodies.

In some embodiments, the antibody that specifically binds to an epitope containing N-acetylglucosamine or N-acetyl-galactosamine is a humanized antibody. Humanized antibodies include human immunoglobulins (recipient antibody) in which residues from a complementarity determining region (CDR) of the recipient are replaced by residues from a CDR of a non-human species (donor antibody) such as mouse rat or rabbit having the desired specificity, affinity and capacity. See Jones et al., *Nature* 321: 522-525 (1986); Riechmann et al., *Nature* 332: 323-329 (1988) and Presta, *Curr. Opin. Struct. Biol.* 2: 593-596 (1992).

Methods for humanizing non-human antibodies are well known in the art. Generally, a humanized antibody has one or more amino acid residues introduced into it from a source which is non-human. Humanization can be essentially performed following the method of Jones et al., *Nature* 321: 522-525 (1986); or through substituting non-human CDR sequences for the corresponding sequences of a human antibody. To ensure humanized antibodies retain high affinity for the antigen, humanized antibodies may be prepared by a process of analyzing the parental sequences and various conceptual humanized products using three-dimensional models of the parental and humanized sequences. Three-dimensional immunoglobulin models are commonly available and are familiar to those skilled m the art. In general, the CDR residues are directly and most substantially involved in influencing antigen binding.

In some embodiments, the antibody that specifically binds to an epitope containing N-acetylglucosamine or N-acetyl-galactosamine is a human antibody. Methods known in the art for producing human antibodies include, without limitation, phage display technology and use of transgenic animals that produce human antibodies m response to antigen.

In some embodiments, the antibody that specifically binds to an epitope containing N-acetylglucosamine or N-acetyl-galactosamine is a chimeric antibody. Chimeric antibodies may refer to an antibody in which residues from a complementarity determining region (CDR) or variable region derived from one species are joined with sequences corresponding to the constant region from another species. Methods for generating chimeric antibodies are known in the art (see, e.g., U.S. Pat. No. 4,816,567).

In some embodiments, the antibody that specifically binds to an epitope containing N-acetylglucosamine or N-acetyl-galactosamine is an antibody fragment. In some embodiments, the antibody that specifically binds to an epitope containing N-acetylglucosamine or N-acetyl-galactosamine is a Fab fragment, scFv, minibody, diabody, scFv multimer, or bispecific antibody fragment. Fab, FV and scFv antibody fragments can all be expressed in and secreted from *E. coli*, thus allowing the straightforward production of large amounts of these fragments, or isolated from phage libraries. Such linear antibody fragments may be monospecific or bispecific.

In some embodiments, the antibody that specifically binds to an epitope containing N-acetylglucosamine or N-acetyl-galactosamine is a bispecific antibody. Chimeric antibodies (BsAbs) are antibodies that have binding specificities for at least two different epitopes, including those on the same or another protein. Methods for making bispecific antibodies are known in the art. Traditional production of full length bispecific antibodies is based on the coexpression of two immunoglobulin heavy-chain/light chain pairs, where the two chains have different specificities.

In some embodiments, the antibody that specifically binds to an epitope containing N-acetylglucosamine or N-acetyl-galactosamine is a multivalent antibody. Multivalent antibodies may refer to any antibody with more than 2 antigen-binding sites. In some embodiments the antibody that specifically binds to an epitope containing N-acetylglucosamine or N-acetyl-galactosamine is a heteroconjugate antibody. Heteroconjugate antibodies may refer to any antibody created by linking two antibodies with different specificities, such as by a covalent linkage.

According to a different approach, antibody variable domains with the desired binding specificities (antibody-antigen combining sites) are fused to immunoglobulin constant domain sequences. DNAs encoding the immunoglobulin heavy chain fusions and, if desired, the immunoglobulin light chain, are inserted into separate expression vectors, and are co-transfected into a suitable host organism.

In some embodiments, compositions containing an antibody that specifically binds to an epitope containing N-acetylglucosamine or N-acetyl-galactosamine may include pharmaceutically acceptable carriers, excipients, or stabilizers that are nontoxic to the cell or mammal being exposed thereto at the dosages and concentrations employed as part of a pharmaceutical composition. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin gelatin, or immunoglobulins; hydrophilic polymers such as polyvinylpyrrolidone, amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

Polynucleotides, Vectors Encoding Antibodies, and Host Cells

Certain aspects of the present disclosure relate to the production of antibodies that specifically bind to an epitope containing N-acetylglucosamine, or N-acetyl-galactosamine. In particular, certain aspects relate to isolated polynucleotides containing a nucleic acid sequence encoding an antibody that specifically binds to an epitope containing N-acetylglucosamine or N-acetyl-galactosamine. As described above, polynucleotides may refer to deoxyribonucleotides, ribonucleotides modified nucleotides or bases, and/or their analogs. These polynucleotides may be produced in vivo a host cell or through in vitro transcription. Polynucleotides encoding an antibody may refer to polynucleotides bearing the sequence encoding the antibody as it was identified in a cell producing the antibody (e.g., a B cell or hybridoma), or polynucleotides containing synonymous mutations in the sequence that distinguish them from their naturally occurring counterparts but, due to the inherent degeneracy of the genetic code, encode a similar protein. Polynucleotides may be isolated by any means known in the art, including PCR followed by precipitation-based purification of the PCR reaction, or a slice of agarose gel containing the PCR product, or by purification of a vector containing the polynucleotide from a host cell (e.g., plasmid preparation from E. coli).

Certain aspects of the present disclosure relate to vectors containing a nucleic acid sequence encoding an antibody that specifically binds to an epitope containing N-acetylglucosamine or N-acetylgalactosamine. For recombinant production of antibodies or fragments thereof, nucleic acids encoding the desired antibodies or antibody fragments are isolated and inserted into a replicable vector for further cloning (amplification of the DNA) or for expression. DNA encoding the polyclonal or monoclonal antibodies is readily isolated (e.g., with oligonucleotide probes that specifically bind to genes encoding the heavy and light chains of the antibody) and sequenced using conventional procedures. Many cloning and/or expression vectors are commercially available.

Vector components generally include, but are not limited to, one or more of the following, a signal sequence, an origin of replication, one or more marker genes, a multiple cloning site containing recognition sequences for numerous restriction endonucleases, an enhancer element, a promoter and a transcription termination sequence. Both expression and cloning vectors contain a nucleic acid sequence that enables the vector to replicate in one or more selected host-cells. Such sequences are well known for a variety of bacteria, yeast, and viruses. Expression and cloning vectors may also contain a selection gene, known as a selectable marker, whose expression confers resistance to antibiotics or other toxins, complements auxotrophic deficiencies, or supplies critical nutrients not available from complex media.

Expression and cloning vectors usually contain a promoter that is recognized by the host organism and is operably linked to the nucleic acid encoding the antibodies (e.g., antibodies that specifically bind to an epitope containing N-acetylglucosamine or N-acetyl-galactosamine) or fragments thereof. Promoters suitable for use with prokaryotic hosts include the phoA promoter, lactamase and lactose promoter systems, alkaline phosphatase promoter, a tryptophan promoter system, and hybrid promoters such as the tac promoter, although other known bacterial promoters are also suitable. Promoters for use in bacterial systems also will contain a Shine-Dalgarno (S.D.) sequence operably linked to the DNA encoding the antibodies and antibody fragments. Promoter sequences are known for eukaryotes, including the yeast promoters for 3-phosphoglycerate kinase or other glycolytic enzymes and mammalian promoters obtained from the genomes of viruses such as polyoma virus, cytomegalovirus, and most preferably Simian Virus 40 (SV40). Various heterologous mammalian promoters, e.g., the actin promoter, immunoglobulin promoter, and heat-shock promoters, are also known. Expression vectors used in eukaryotic host cells will also contain sequences necessary for the termination of transcription and for stabilizing the mRNA.

Certain aspects of the present disclosure relate to isolated host cells with vectors containing a nucleic acid sequence encoding an antibody that specifically binds to an epitope containing N-acetylglucosamine or N-acetyl-galactosamine. Suitable host-cells for cloning or expressing the DNA encoding antibodies (e.g., antibodies that specifically bind to an epitope containing N-acetylglucosamine or N-acetyl-galactosamine) or fragments thereof in the vectors described herein prokaryotes such as Gram-negative or Gram-positive organisms, for example, Enterobacteriaceae such as E. coli. In addition to prokaryotes, eukaryotic microbes such as filamentous fungi or yeast are also suitable cloning or expression hosts, such as Saccharomyces cerevisiae. For a review discussing the use of yeasts and filamentous fungi for the production of therapeutic proteins, see, e.g., Gerngross, Nat. Biotech. 22: 1409-1414 (2004). Suitable host-cells for the expression of glycosylated antibodies or antibody fragments are derived from multicellular organisms. Examples of invertebrate cells include plant and insect-cells such as Spodoptera frugiperda (caterpillar), Aedes aegypti (mosquito), Drosophila melanogaster (fruitfly), or Bombyx mori (moth) cells. Examples of useful mammalian host-cell lines are monkey kidney CV1 line transformed by SV40 (COS-7 ATCC 1651); human embryonic kidney line (293 or 293 cells subcloned for growth in suspension culture, Graham et al., J. Gen Virol. 36:59 (1977)); baby hamster kidney cells (BHK, ATCC CCL 10), Chinese hamster ovary cells/-DHFR (CHO, Urlaub et al., Proc. Nat'l Acad. Sci. USA 77:4216 (1980)), African green monkey kidney cells (VERO-76, ATCC CRL-1587); human cervical carcinoma cells (HELA, ATCC CCL, 2); and a human hepatoma line (Hep G2). For a review of certain mammalian host cell lines suitable for antibody production, see, e.g., Yazaki and Wu, Methods in Molecular Biology, Vol. 248 (B.K.C. Lo, ed., Humana Press, Totowa, N.J., 2003), pp. 255-268. These examples are illustrative rather than limiting.

Antibody Production and Purification

Certain aspects of the present disclosure relate to methods of producing an antibody by culturing host cells with vectors containing a nucleic acid sequence encoding an antibody and recovering the antibody from the cell culture. Host cells are transformed with the above-described expression or cloning vectors for antibody or antibody fragment production and cultured in conventional nutrient media modified as appropriate for inducing promoters, selecting transformants, or amplifying the genes encoding the desired sequences.

The host-cells used to produce the antibodies (e.g., antibodies that specifically bind to an epitope containing N-acetylglucosamine or N-acetyl-galactosamine) or antibody fragments described herein may be cultured in a variety of media. Commercially available media such as Ham's F10 (Sigma), Minimal Essential Medium (DMEM), Sigma), RPMI-1640 (Sigma), and Dulbecco's Modified Eagle's Medium ((DMEM), Sigma) are suitable for culturing the host-cells. Any of these media may be supplemented as necessary with hormones and/or other growth factors (such as insulin, transferrin, or epidermal growth factor), salts (such as sodium chloride, calcium, magnesium, and phosphate), buffers, nucleotides, antibiotics, trace elements, and glucose or an equivalent energy source. Any other necessary supplements may also be included at appropriate concentrations that would be known to those skilled in the art. The culture conditions, such as temperature, pH, and the like, are those previously used with the host-cell selected for expression, and will be apparent to the ordinarily skilled artisan.

When using recombinant techniques, the antibodies (e.g., antibodies that specifically bind to an epitope containing N-acetylglucosamine or N-acetyl-galactosamine) or antibody fragments can be produced intracellularly, in the periplasmic space, or secreted directly into the medium. Antibodies prepared from such cells can be purified using, for example, hydroxylapatite chromatography, gel electrophoresis, dialysis, and affinity chromatography, such as that using protein A or protein G attached to a matrix (e.g., agarose).

In general, various methodologies for purifying preparing antibodies for use in research, testing, and clinical applications are well-established in the art, consistent with the above-described methodologies and/or as deemed appropriate by one skilled in the art for a particular antibody of interest.

V. Cancer

Certain aspects of the present disclosure relate to methods for treating or preventing cancer in an individual by administering to the individual an effective amount of a composition containing an antibody that specifically binds to an epitope containing N-acetylglucosamine N-acetyl-galactosamine, where the epitope is expressed by a cancer cell. In some embodiments, the epitope is expressed on a cell surface of a cancer cell. In some embodiments, binding of the antibody to the epitope expressed on the cell surface of the cancer cell inhibits growth of the cancer cell.

Described herein is the unexpected result that certain glycoproteins, particularly N-acetylglucosamine and/or N-acetyl-galactosamine, are highly expressed on the cell surface of many types of human cancer cells, as compared to little or no expression on the cell surface of normal human cells. As a result, these sugar moieties may serve as biomarkers for the presence of cancer that may also be used to preferentially target therapeutic agents (e.g., antibodies) to cancer cells. Moreover, the present disclosure also describes how, advantageously, antibodies specific to N-acetylglucosamine and/or N-acetyl-galactosamine may bind to the cell surface and are able to inhibit the growth of cancer cells expressing these sugar moieties.

The results described herein demonstrate that antibodies that specifically bind to an epitope containing N-acetylglucosamine or N-acetyl-galactosamine are broadly effective in inhibiting the growth of many different types of cancer cells. This property was demonstrated through the in vitro use of human cancer cell lines. Importantly, experiments using a tumor xenograft model further established the efficacy of antibodies that specifically bind to an epitope containing N-acetylglucosamine or N-acetyl-galactosamine in inhibiting the growth of human cancer cells in vivo. This tumor xenograft model is known in the art as a powerful tool for testing and predicting the drug response of human tumors (see, e.g., Richmond, A. and Su, Y, (2008) *Dis. Model Mech.* 1(2-3): 78-82).

While the results described herein predict that antibodies that specifically bind to an epitope containing N-acetylglucosamine or N-acetyl-galactosamine are broadly effective against multiple forms of human cancer, in some embodiments, the cancer cell whose growth is inhibited by the antibody is selected from: a glioma cell, a hepatocarcinoma cell, a lung cancer cell, a breast cancer cell, an ovarian carcinoma cell, a cervical adenocarcinoma cell, a colon carcinoma cell, a stomach or gastric carcinoma cell, an esophageal carcinoma cell, and a fibrosarcoma cell.

In some embodiments, the cancer cell is a glioma cell. Glioma cells may refer to any malignant cell originating from a glial cell, e.g., glial cells of the brain or spine, including primary tumors or glioma cells that have metastasized to other sites. Glioma cells may refer to a homogeneous population of glioma cells, or a mixed population of cells arising from different types of glia. In some embodiments, the glioma cell may be an astrocytoma cell. In some embodiments, the glioma cell may be an oligodendroglioma cell, a brainstem glioma cell, an ependymoma cell, or an optic nerve glioma cell.

In some embodiments, the cancer cell is a hepatocarcinoma cell. Hepatocarcinoma cells may refer to any carcinoma cell originating from the liver, including primary tumors or hepatocarcinoma cells that have metastasized to other sites.

In some embodiments, the cancer cell is a lung cancer cell. Lung cancer cells may refer to any cancer cell originating from the lung, including primary tumors or lung cancer cells that have metastasized to other sites. In some embodiments, the lung cancer cell may be a non-small-cell lung cancer cell. In some embodiments, the lung cancer cell may be a lung adenocarcinoma cell. In some embodiments, the lung cancer cell may be a lung squamous cell carcinoma. In some embodiments, the lung cancer cell may be a small-cell lung cancer cell.

In some embodiments, the cancer cell is a breast cancer cell. Breast cancer cells may refer to any cancer cell originating from the breast, including primary tumors or breast cancer cells that have metastasized to other sites. In some embodiments, the breast cancer cell may be a ductal carcinoma in situ cell. In some embodiments, the breast cancer cell may be an invasive ductal carcinoma cell. In some embodiments, the breast cancer cell may be an invasive lobular carcinoma cell.

In some embodiments, the cancer cell is an ovarian carcinoma cell. Ovarian carcinoma cells may refer to any carcinoma cell originating from the ovary, including primary tumors or ovarian carcinoma cells that have metastasized to other sites. In some embodiments, the ovarian carcinoma cell may be a surface epithelial-stromal tumor cell. In some embodiments, the ovarian carcinoma cell may be a sex, cord-stromal tumor cell. In some embodiments, the ovarian carcinoma cell may be a germ cell tumor cell. Ovarian carcinoma cells may refer to a homogeneous population of ovarian carcinoma cells, or a mixed population of cells arising from different types of ovarian carcinomas.

In some embodiments, the cancer cell is a cervical adenocarcinoma cell. Cervical adenocarcinoma carcinoma cells may refer to any adenocarcinoma cell originating from the cervix, including primary tumors or cervical adenocarcinoma cells that have metastasized to other sites. In some embodiments, the cervical adenocarcinoma cell is an adenosquamous carcinoma cell.

In some embodiments, the cancer cell is a colon carcinoma cell. Colon carcinoma cells may refer to any carcinoma, cell originating from the colon or rectum, including primary tumors or colon carcinoma cells that have metastasized to other sites. In some embodiments, the colon carcinoma cell is an adenocarcinoma cell. In some embodiments, the colon carcinoma cell is an adenosquamous carcinoma cell.

In some embodiments, the cancer cell is a stomach or gastric carcinoma cell. Stomach or gastric carcinoma cells may refer to any carcinoma cell originating from the stomach, including primary tumors or stomach carcinoma cells that have metastasized to other sites. In some embodiments, the stomach or gastric carcinoma cell is an adenocarcinoma cell. In some embodiments, the stomach or gastric carcinoma cell is a diffuse type adenocarcinoma (mucinous, colloid, linitis plastica, leather-bottle stomach) cell. In some embodiments, the stomach or gastric carcinoma cell is a lymphoma cell.

In some embodiments, the cancer cell is an esophageal carcinoma cell. Esophageal carcinoma cells may refer to any carcinoma cell originating from the esophagus, including primary tumors or esophageal carcinoma cells that have metastasized to other sites. In some embodiments, the esophageal carcinoma, cell is an adenocarcinoma cell. In some embodiments, the esophageal carcinoma cell is a squamous carcinoma cell.

In some embodiments, the cancer cell is a fibrosarcoma cell. Fibrosarcoma cells may refer to any carcinoma cell originating from the fibrous connective tissue, including primary tumors or esophageal carcinoma cells that have metastasized to other sites.

VI. Gastrointestinal Disease

Certain aspects of the present disclosure relate to methods for treating or preventing gastrointestinal disease by administering to the individual an effective amount of a composition containing an antibody that specifically binds to an epitope containing N-acetylglucosamine or N-acetyl-galactosamine, where the epitope is expressed by an inflammatory cell.

In some embodiments, the epitope is expressed on a cell surface of an inflammatory cell. In some embodiments, the inflammatory cell is an intestinal inflammatory cell of colitis, inflammatory bowel disease, or gastroenteritis, and the epitope is expressed on a cell surface of the inflammatory cell. As described herein, antibodies that specifically recognize an epitope containing N-acetylglucosamine or N-acetyl-galactosamine may bind to inflammatory cells (e.g., leukocytes, such as neutrophils, macrophages, monocytes, eosinophils, and/or basophils) at sites of inflammation in the colon, such as those seen in diseases characterized by inflammation of the colon (e.g., colitis, IBD, or gastroenteritis).

VII. Methods of Treatment

Cancer

Certain aspects of the present disclosure relate to methods for treating or preventing cancer in an individual by administering to the individual an effective amount of a composition containing an antibody that specifically binds to an epitope containing N-acetylglucosamine or N-acetyl-galactosamine. It is a surprising finding described herein that antibodies that specifically bind to an epitope containing N-acetylglucosamine or N-acetyl-galactosamine expressed on a cell surface of or in the cancer cell, may be used to inhibit the growth of a variety of cancer cells. In some embodiments, the binding of the antibody to the epitope expressed on the cell surface of the cancer cell inhibits growth of the cancer cell.

In some embodiments, the cancer may include brain cancer, liver cancer, lung cancer, breast cancer, ovarian cancer, cervical cancer, colon cancer, stomach cancer, esophageal cancer, and fibrosarcoma. Since the present disclosure demonstrates that many types of cancer tissues express high levels of N-acetylglucosamine or N-acetyl-galactosamine the methods described herein may be broadly effective in treating many types of cancer. In some embodiments, the cancer to be treated or prevented refers to a primary tumor, e.g., a primary tumor representing brain cancer liver cancer, lung cancer, breast cancer, ovarian cancer, cervical cancer, colon cancer, stomach cancer, esophageal cancer, or fibrosarcoma. In some embodiments, the cancer to be treated or prevented refers to a metastatic cancer originally representing brain cancer, liver cancer, lung cancer, breast cancer, ovarian cancer, cervical cancer colon cancer, stomach cancer, esophageal cancer, or fibrosarcoma.

In some embodiments, the cancer to be treated or prevented is a brain cancer. Brain cancer may refer to any cancer originating from the brain, including but not limited to a cancer made of the cells described above. Examples of brain cancers may include without limitation gliomas, meningiomas, nerve sheath tumors, and pituitary adenomas. Brain cancer may also refer to a cancer originating from the central nervous system, e.g., the spine.

In some embodiments, the cancer to be treated or prevented is a liver cancer. Liver cancer may refer to any cancer originating from the liver, including but not limited to a cancer made of the cells described above. Examples of liver cancers may include without limitation hepatocarcinomas cholangiocarcinomas, and hepatoblastomas.

In some embodiments, the cancer to be treated or prevented is a lung cancer. Lung cancer may refer to any cancer originating from the lung, including but not limited to a cancer made of the cells described above. Examples of lung cancers may include without limitation non-small-cell lung cancers, including adenocarcinomas squamous-cell carcinomas, and large-cell carcinomas, as well as small-cell lung carcinomas.

In some embodiments, the cancer to be treated or prevented is a breast cancer. Breast cancer may refer to any cancer originating from the breast, including but not limited to a cancer made of the cells described above. Examples of breast cancers may include without limitation ductal carcinomas in situ, invasive ductal carcinomas, triple negative breast cancer (e.g., cancer made of cells negative for progesterone, estrogen, and HER2/neu receptors), and inflammatory breast cancer.

In some embodiments, the cancer to be treated or prevented is an ovarian cancer. Ovarian cancer may refer to any cancer originating from the ovary, including but not limited to a cancer made of the cells described above. Examples of ovarian cancers may include without limitation surface epithelial-stromal tumors (including, e.g., endometrioid tumors, mucinous cystadenocarcinomas, and serous tumors), germ cell tumors, sex cord-stromal tumors, and mixed ovarian tumors.

In some embodiments, the cancer to be treated or prevented is a cervical cancer. Cervical cancer may refer to any cancer originating from the cervix, including but not limited to a cancer made of the cells described above. Examples of cervical cancers may include without limitation squamous cell carcinomas, adenocarcinomas, small cell carcinomas, adenosquamous carcinomas, neuroendocrine tumors, villoglandular adenocarcinomas, and glassy cell carcinomas.

In some embodiments, the cancer to be treated or prevented is a colon cancer. Colon cancer may refer to any cancer originating from the colon or rectum, including but not limited to a cancer made of the cells described above. Examples of colon cancers may include without limitation adenocarcinomas and adenosquamous carcinomas.

In some embodiments, the cancer to be treated or prevented is a stomach or gastric cancer, Stomach or gastric cancer may refer to any cancer originating from the stomach, including but not limited to a cancer made of the cells described above, Examples of stomach or gastric cancers may include without limitation adenocarcinomas, diffuse type adenocarcinomas (mucinous, colloid, linitis plastica, leather-bottle stomach) and lymphoma.

In some embodiments, the cancer to be treated or prevented is an esophageal cancer. Esophageal cancer may refer to any cancer originating from the esophagus, including but not limited to a cancer made of the cells described above. Examples of esophageal cancers may include without limitation adenocarcinomas and squamous carcinomas.

In some embodiments, the cancer to be treated or prevented is a fibrosarcoma. Fibrosarcomas may refer to any carcinomas originating from the fibrous connective tissue, including but not limited to a cancer made of the cells described above.

Administration and Combination Therapies

Any method known in the art may be used to administer an effective amount of a composition containing an antibody that specifically binds to an epitope containing N-acetylglucosamine or N-acetyl-galactosamine, such as intravenous administration as a bolus or by continuous infusion over a period of time, by intramuscular intraperitoneal, intracerobrospinal, subcutaneous, intra-articular, intrasynovial, intrathecal, oral, topical, or inhalation routes. In some embodiments, the antibody is administered orally. In some embodiments, the composition contains an antibody that specifically binds to an epitope containing N-acetylglucosamine or N-acetyl-galactosamine and another protein, e.g., another antibody that does not specifically bind to an epitope containing N-acetylglucosamine or N-acetyl-galactosamine. An effective amount of a composition containing an antibody that specifically binds to an epitope containing N-acetylglucosamine or N-acetyl-galactosamine may be determined by any method known in the art and may depend upon a number of characteristics of the individual as described above.

Certain aspects of the present disclosure relate to methods for treating or preventing cancer in an individual by administering to the individual an effective amount of a composition containing an antibody that specifically binds to an epitope containing N-acetylglucosamine or N-acetyl-galactosamine and an amount of another anti-cancer agent, where the antibody and the anti-cancer agent in conjunction provide effective treatment or prevention of cancer in the individual. Any suitable anti-cancer agent known in the art may be used in combination with the antibodies described herein. Anti-cancer agents may include antibodies (including, antibody-drug conjugates), small molecules, immunotherapeutics, differentiating agents, targeted therapies, and hormones.

In some embodiments, the anti-cancer agent is a chemotherapeutic agent. Many types of chemotherapeutic agents are known in the art. Examples of chemotherapeutic agents may include without limitation antimetabolites (e.g., 5-fluorouracil or capecitabine), anthracyclines, anti-tumor antibiotics (e.g., actinomycin-D, mitomycin-C, or bleomycin), mitotic inhibitors (e.g., to tines such as Taxol® or epothilones), corticosteroids, topoisomerase inhibitors (e.g., etoposide), alkylating agents, and platinum drugs (e.g., cisplatin oxalaplatin or carboplatin). These drugs are provided as examples for one of skill in the art and are in no way intended to limit the choice of chemotherapeutic agents.

Gastrointestinal Disease

Certain aspects of the present disclosure relate to methods for treating or preventing gastrointestinal disease in an individual by administering to the individual an effective amount of a composition containing an antibody that specifically binds to an epitope containing N-acetylglucosamine or N-acetyl-galactosamine. It is a surprising finding described herein that antibodies that specifically bind to an epitope containing N-acetylglucosamine or N-acetyl-galactosamine, expressed on a cell surface of an inflammatory cell, may be used to treat or prevent a wide range of gastrointestinal diseases, including autoimmune and infectious diseases.

As described herein, the methods of the present disclosure are effective against a wide range of gastrointestinal diseases in an individual. In some embodiments, the individual has inflammatory bowel disease. An inflammatory bowel disease of the present disclosure may be chronic or acute. As is known in the art, many gastrointestinal diseases such as inflammatory bowel disease may present symptoms in tissues including without limitation the small and large intestines, mouth, stomach, esophagus, and anus. In some embodiments, an inflammatory bowel disease may include colitis (such as diversion, lymphocytic, collagenous, or indeterminate colitis) or Behcet's disease.

In some embodiments, the individual has Crohn's disease. In some embodiments, the individual has ulcerative colitis. In some embodiments, the individual has acute infectious gastroenteritis. In some embodiments, the individual has a hemorrhoid.

In some embodiments, the individual has a gastrointestinal disease caused by a viral infection. Viruses known to cause gastrointestinal disease may include without limitation rotaviruses, noroviruses, adenoviruses, and astroviruses. In some embodiments, the viral infection is a rotaviral infection.

In some embodiments, the individual with a gastrointestinal disease is a human. In some embodiments, the individual with a gastrointestinal disease is a non-human animal.

Many suitable methods for administering a composition for treating or preventing a gastrointestinal disease are known in the art. In some embodiments, an antibody of the present disclosure may be administered intravenously, intramuscularly, subcutaneously, topically, orally, transdermally, intraperitoneally, intraorbitally, by implantation, by inhalation, intrathecally, intraventricularly, or intranasally.

VIII. Methods of Detection

Certain aspects of the present disclosure relate, to methods for detecting the presence of cancer cells in an individual by: obtaining a biological sample from an individual, contacting the biological sample with an antibody that specifically binds to an epitope containing N-acetylglucosamine or N-acetyl-galactosamine, and detecting the amount of antibody binding to the biological sample, where antibody binding indicates the presence of cancer cells in the individual. Advantageously, the present disclosure describes how an antibody that specifically binds to an epitope containing N-acetylglucosamine or N-acetyl-galactosamine may be used to detect the presence of a cancer in an individual, due to the correlation between elevated levels of N-acetylglucosamine or N-acetyl-galactosamine in a serum sample and the presence of a cancer. These methods may be used to detect many types of cancer, including without limitation lung cancer, liver cancer, breast cancer, colon or colorectal cancer, esophageal cancer, stomach cancer, endometrial cancer, cervical cancer, thyroid cancer, brain cancer, and lymphoma.

Specific binding between the antibody and an epitope containing N-acetylglucosamine or N-acetyl-galactosamine may be detected by any method known in the art. Methods for detecting binding between an antibody and an epitope are well known in the art and may, include an ELISA (enzyme-linked immunosorbent assay) immunohistochemistry (IHC) assays, immunofluorescence assays, flow cytometry, CTC (Circulating tumor cells) assays, and immuno-colloidal gold assays. These exemplary assays are well known to one of skill in the art; for more detailed descriptions; see, e.g., Harlow and Lane, eds. (1988) *Antibodies, A Laboratory Manual*. Examples of ELISAs may include direct, indirect, competitive, and sandwich ELISAs. Any surface may be used, including without limitation a plate (e.g., a 96-well plate) or a column.

In some embodiments, the amount of antibody binding to an epitope containing N-acetylglucosamine or N-acetyl-galactosamine detected as described above may be compared with an amount of antibody binding detected using a control sample. An increased amount of antibody binding to the biological sample may indicate the presence of cancer cells in the individual, as compared to the amount of antibody binding to the control sample. A control sample may be processed as described above with the biological sample from the individual to be tested. Examples of control samples may include a sample from a cancer-free individual, or a sample with a known quantity of N-acetylglucosamine and/or N-acetyl-galactosamine. As a non-limiting example, serum from a test individual may be tested using the methods described herein and compared with serum from a healthy cancer-free) individual. In this scenario, increased antibody binding in the serum from the test individual, compared to the healthy individual or the serum with a known quantity of N-acetylglucosamine and/or N-acetyl-galactosamine, may indicate the presence of cancer cells in the test individual.

Any body fluid or section may be used as a biological sample of the present disclosure. Examples of biological samples may include without limitation blood, serum, urine, feces, milk, semen saliva, chest fluid, abdominal fluid, cerebrospinal fluid, sputum, and any other body fluid or secretion.

As shown herein, many types of cancer cells may be detected in an individual using the methods described herein. Examples of cancer cells that may be detected in an individual include without limitation lung cancer cells, liver cancer cells, breast cancer cells, colon or colorectal cancer cells, esophageal cancer cells, stomach cancer cells, endometrial cancer cervical cancer cells thyroid cancer cells, brain cancer cells, and lymphoma cells.

In addition, saccharide-related biomarkers themselves may be used in the detection of auto-antibodies in subjects with cancers or other diseases. These auto-antibodies may bind to the saccharides that are differentially expressed on or in those cancerous or otherwise diseased tissues or cells, or released to blood, urine, feces, milk, semen saliva, and body fluid or secretions. Body fluid or secretions may include but not limited to chest fluid abdomen fluid, cerebrospinal fluid, sputum, and organ smears, in some embodiments, saccharide-related biomarkers may include without limitation N-Acetyl-Glucosamine, N-Acetyl-Galactosamine or fucose, or glycoconjugates hearing distinct N-Acetyl glucosamine, N-Acetyl-Galactosamine or fucose.

IX. Kits

Certain aspects of the present disclosure relate to kits containing a pharmaceutical composition containing an antibody that specifically binds to an epitope containing, N-acetylglucosamine or N-acetyl-galactosamine. In some embodiments, the kits may further include instructions for administering an effective amount of the pharmaceutical composition to an individual for treating-cancer. These instructions may refer to instructions customarily included in commercial packages of medicaments that contain information about the indications customarily included in commercial packages of medicaments that contain information about the indications usage, dosage, administration, contraindications, other medicaments to be combined with the packaged product, and/or warnings concerning the use of such medicaments, etc.

Suitable containers for a kit of the present disclosure include, for example, bottles, vials (e.g., dual chamber vials), syringes (such as single or dual chamber syringes) and test tubes. The article of manufacture may further comprise a label or a package insert, which is on or associated with the container, may indicate directions for reconstitution and/or use of the formulation. The label or package insert may further indicate that the formulation is useful or intended for oral or other modes of administration for treating or preventing cancer in an individual. The article of manufacture may further include other materials desirable from a commercial, therapeutic, and user standpoint, including other buffers, diluents, filters, needles, syringes, and package inserts with instructions for use.

In some embodiments, the kits containing a pharmaceutical composition containing an antibody that specifically binds to an epitope containing N-acetylglucosamine or N-acetyl-galactosamine may further contain instructions for detecting the presence of cancer cells in an individual. These instructions may refer to instructions customarily included in commercial packages of ELISA assay kits, immunohistochemistry (IHC) assay kits immunofluorescence assay kits, flow cytometry assay kits, CTC (Circulating tumor cells) assay kits, and immuno-colloidal assay kits. A kit of the present disclosure may also contain any oilier reagents useful for detecting the presence of cancer cells in an individual, such as 96-well microtiter plates, a non-specific protein such as bovine serum albumin, a secondary antibody that binds to an antibody of the present disclosure without affecting its antigen-binding, and reagents for detection, such as a fluorescent or luminescent label, or an enzyme and substrate that produce a detectable signal (e.g., horseradish peroxidase and TMB).

Certain aspects of the present disclosure relate to kits containing a pharmaceutical composition containing N-acetylglucosamine or N-acetyl-galactosamine and instructions or other reagents for using the pharmaceutical composition for detecting the presence of an auto-antibody in an individual with cancer or inflammation. These instructions may refer to instructions customarily included in commercial packages of ELISA assay kits, immunohistochemistry (IHC) assay kits, immunofluorescence assay kits, flow cytometry assay kits, CTC (Circulating tumor cells) assay kits, and immuno-colloidal gold assay kits. A kit of the present disclosure may also contain any other reagents useful for detecting the presence of cancer cells in an individual, such as 96-well microtiter plates, a non-specific protein such as bovine serum albumin, a secondary antibody that binds to an antibody of the present disclosure without affecting its antigen-binding, and reagents for detection, such as a fluorescent or luminescent label, or an enzyme and substrate that produce a detectable signal (e.g., horseradish peroxidase and TMB).

The specification is considered to be sufficient to enable one skilled in the art to practice the invention. Various modifications of the invention in addition to those shown and described herein will become apparent to those skilled in the art from the foregoing description and fall within the scope of the appended claims. All publications, patents, and patent applications cited herein are hereby incorporated by reference in their entirety for all purposes.

EXAMPLES

The invention will be more fully understood by reference to the following examples. They should not, however, be construed as limiting the scope of the invention. It is understood that the examples and embodiments described herein are for illustrative purposes only and that various modifications or changes in light thereof will be suggested to persons skilled in the art and are to be included within the spirit and purview of this application and scope of the appended claims.

Example 1: Expression of N-acetylglucosamine and N-acetyl-galactosamine on Cancer Cells The identification of biomarkers that are preferentially expressed by cancer cells, rather than normal human cells, may allow for the design of new assays and therapeutic approaches to aid in the diagnosis, treatment, and/or prevention of cancer. To meet this demand, described herein are monoclonal antibodies that bind to N-acetylglucosamine and N-acetyl-galactosamine. These results are based in part on the surprising discovery that N-acetylglucosamine and N-acetyl-galactosamine are expressed on the surface of many disparate cancer cells but show little to no expression in normal human tissues. As a result, monoclonal antibodies that bind to N-acetylglucosamine and N-acetyl-galactosamine and inhibit the growth of cancer cells may find great potential use in the diagnosis, treatment, and/or prevention of cancer.

Materials and Methods
Tissue Arrays

Binding of wheat germ agglutinin (WGA) to human healthy and malignant tissues was detected with a tissue array chip. The chip contained epitopes from FDA-recommended normal human organs and malignant tissues from patients with cancers (Imgenex, San Diego, and US Biomax, Rockville, Md., USA). For more detailed description of tissue arrays, see WO2009126652.

Immunohistochemistry

An immunohistochemistry (IHC) assay with plant lectins was used for identification of saccharide-relating biological targets or markers relating to cancers and other diseases. Healthy or cancerous human tissues were stained with the following plant lectins: Biotinylated-wheat germ agglutinin (WGA), which specifically recognizes N-acetylglucosamine, Biotinylated-Ulex Europaeus I (UEA I), which specifically recognizes Fucose; Biotinylated-soybean agglutinin (SBA) or dolichos biflorus agglutinin (DBA), which specifically recognize N-acetyl-galactosamine; Biotinylated-peanut agglutinin (PNA), which specifically recognizes galactose: Biotinylated-Ricinus communis agglutinin (RCA1 or $RAC_{120}$), which specifically recognizes galactose and N-Acetyl-Galactosamine; and Biotinylated-concanavalin A (ConA) which specifically recognizes mannose. All plant lectins were supplied by Vector Laboratories, Burlingame, Calif., USA. Horseradish Peroxidase Avidin D (HRP Avidin D) and VECTASTAIN ABC Kit (Vector Laboratories, Burlingame, Calif., USA) were used as a secondary reagent and peroxidase substrate.

Generation of Monoclonal Antibodies

BALB/c mice were immunized with a mixture of lysates from human tumor cell lines representing lung carcinoma (A549), hepatocarcinoma (HEP-G2), and colon carcinoma (SW11/b). Hybridoma cells were made by fusing myeloma cells with the spleen cells from the mice that had been immunized with the human tumor antigens. Monoclonal antibodies binding to N-acetylglucosamine or N-acetyl-galactosamine were selected by ELISA using Acetyl-Glucosamine or N-acetyl-galactosamine as the screening antigen. Methods for mouse immunization, generating hybridoma cells, and ELISA-based screening are known in the art.

ELISA Assay for Antibodies Binding to Glycoproteins and Tumor Antigens

An ELISA assay was developed for detection of the binding of monoclonal antibodies to N-acetylglucosamine, N-acetyl-galactosamine and human tumor antigens. Briefly, 96-well ELISA plates were coated with human tumor antigens (0.25 mg/ml), using 100 μl/well, in duplicate. Positive controls included N-acetylglucosamine (0.25 mg/ml) and N-acetyl-galactosamine (0.25 mg/ml), 100 μl/well, in duplicate. Phosphate buffered saline (PBS) was used as a negative control. Horseradish peroxidase (HRP)-conjugated anti-mouse IgG was used as secondary reagent, and TMB (3,3',5,5'-tetramethylbenzidine) Peroxidase EIA Substrate Kit (Bio-Rad, Hercules, Calif. USA) was used for the detection of the HRP-labeled antibodies. The plates were read by an ELISA reader at $OD_{450}$.

MTT Assay for Tumor Cell Growth

An MTT assay was developed for detection of the in vitro inhibition of monoclonal antibodies disclosed in the present invention on human tumor cells. Briefly, a 96-well tissue-culture plate with human tumor cells at about 50% confluence was incubated with monoclonal antibodies at different concentrations for 45 hours. Then the medium of each well was removed and replaced with 100 μL fresh culture medium. 10 μL of 12 mM MTT (3-(4,5-dimethylthiazol-2-yl)-2,5-diphenyltetrazolium bromide) stock solution was added to each well, and 10 μL of the MTT stock solution was added to 100 μL of medium alone as a negative control. The plate was incubated at 37° C. for 4 hours, then 50 μL of DMSO was added to each well and mixed thoroughly. The plate was then read using absorbance at 570 nm.

Xenografts

Briefly, 3-4 week old female C.B-17 SCID rats (Harlan, Madison, Wis.) were randomized into three groups (3 mice each group). Each mouse was inoculated via subcutaneous injection with $5 \times 10^6$ of A549 cells; followed by intravenous (iv) injection of saline (vehicle control), wheat germ agglutinin (WGA), or monoclonal antibody 3C4F12 once per day at days 10, 14, 17, and 21 post-cell inoculation. One dose of WGA was 5 μg of WGA in 100 μl of saline. One dose of monoclonal antibody 3C4F12 was 50 μg of the antibody in 100 μl of saline. Tumor growth was measured twice weekly from day 10 post cell implantation. Tumor size was calculated using the formula $$\text{length} \times (\text{width}/2) \times 2\pi = \text{tumor size}$$

ELISA-Based Blood Test

Briefly, 96-well ELISA plates were coated with human serum from cancer patients at 80 μl/well in duplicate. Positive controls included N-acetylglucosamine (0.25 mg/ml) at 100 μ/well in duplicate. PBS was used as a blank control MAb-1C5C9 (2-5 μg/ml, 100 μl/well) was used as detecting antibody. Horseradish peroxidase (HRP)-conjugated anti-mouse IgG was used as secondary reagent, and TMB (3,3',5,5'-tetramethylbenzidine). Peroxidase EIA Substrate Kit (Bio-Rad, Hercules, Calif. USA) was used for the detection of the HRP-labeled antibodies. The plates were read by an ELISA reader at $OD_{450}$. The results were determined based on the value of $OD_{450}$.

Flow Cytometry Assay

Briefly, 100 µl of fresh blood from either a healthy individual or a cancer patient was stained with monoclonal antibodies of 2F7H4. 1C5C9 and 1B3E12 and with fluorescent-labeled goat anti-mouse IgG, respectively. Red blood cells were then destroyed by red blood cell lysis buffer. The fluorescent-positive cells of peripheral blood mononuclear cells (PBMC) were detected by a flow cytometer.

Results

The plant lectins described in Materials and Methods above were used as probes to examine the expression of various glycoproteins in normal and cancerous human tissues using immunohistochemistry. Representative images of biotinylated-wheat germ agglutinin straining, which specifically detects N-acetylglucosamine, are shown in FIG. 1 (compare healthy tissues in FIG. 1A with cancer-adjacent tissues and cancer tissues in FIG. 1B and FIG. 1C, respectively). These experiments demonstrated that a majority of normal human organs except bone marrow, salivary gland and hypophysis show little or no expression of N-acetylglucosamine.

In contrast the following cancerous tissues were found to express N-acetylglucosamine: skin malignant melanoma, brain malignant oligodendroglioma, kidney clear cell carcinoma, skin basal cell carcinoma, throat carcinoma, Hodgkin's lymphoma, colon intermediate grade interstitialoma, thyroid medullary carcinoma, and skin squamous cell carcinoma. These results are quantified in Table 1.

TABLE 1

Table 1. Expression of GlcNAc* on or in cancerous tissues

| Tumor tissue | N= | Positive | Negative |
| --- | --- | --- | --- |
| Lung carcinoma | 6 | 6 | 0 |
| Breast carcinoma | 3 | 3 | 0 |
| Stomach carcinoma | 5 | 5 | 0 |
| Prostate carcinoma | 8 | 7 | 1 |
| Pancreas carcinoma | 7 | 6 | 1 |
| Colon carcinoma | 3 | 3 | 0 |
| Kidney carcinoma | 5 | 4 | 1 |
| Cervix carcinoma | 4 | 4 | 0 |
| Brain malignant carcinoma | 5 | 4 | 1 |
| Brain benign tumor | 4 | 1 | 3 |
| Skin carcinoma | 3 | 3 | 0 |
| Thyroid carcinoma | 3 | 3 | 0 |
| Bladder carcinoma | 1 | 1 | 0 |
| Total | 57 | 50 | 7 |

*GlcNAc = N-acetylglucosamine

Figure 2:
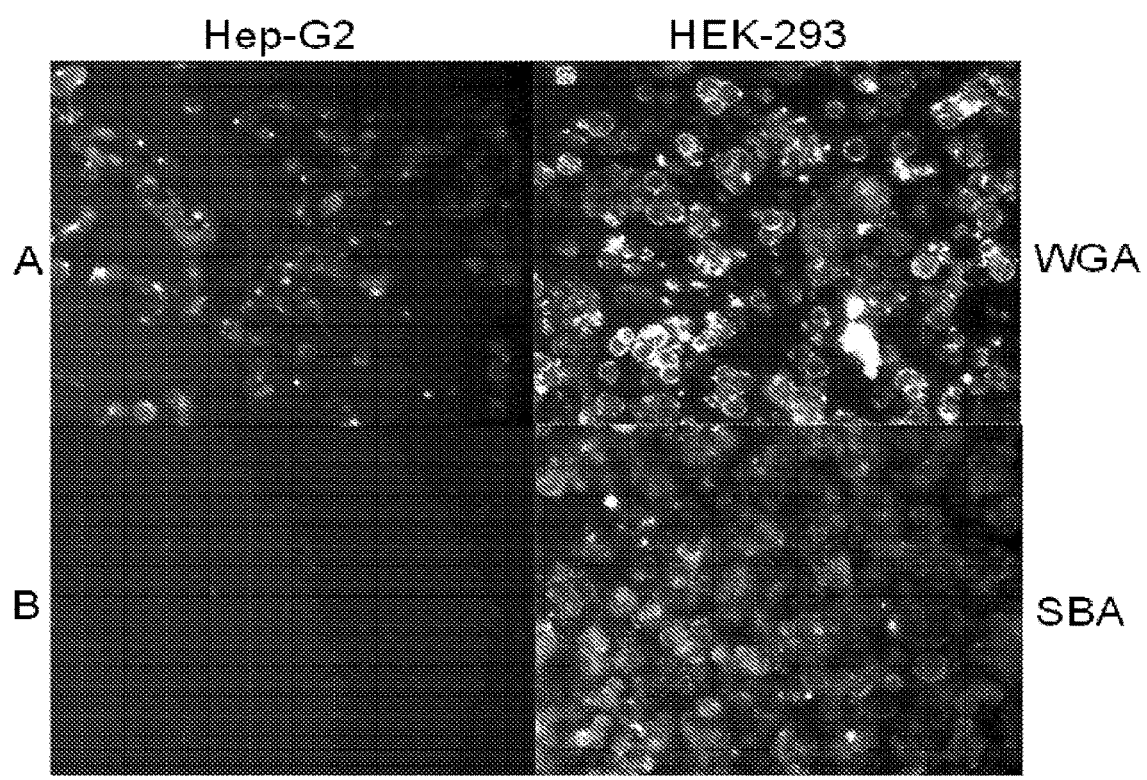
FIG. 2 shows fluorescence staining of Hep-G2 and HEK-293 cell lines using wheat germ agglutinin (WGA; A) or soybean agglutinin (SBA; B).

To further examine the expression of various glycoproteins on cancer cells, transformed cell lines Hep-G2 and HEK-293 were stained in immunofluorescence assays with biotinylated-lectins and fluorescence-conjugated streptavidin. As shown in FIG. 2, wheat germ agglutinin, which specifically recognizes N-acetylglucosamine, yielded robust staining of both Hep-G2 and HEK-293 cells (FIG. 2A). Soybean agglutinin (SBA), which specifically recognizes N-acetyl-galactosamine, stained HEK-293 cells (FIG. 2B). These results demonstrate that certain glycoproteins, particularly N-acetylglucosamine and N-acetyl-galactosamine, are highly expressed on the cell surface of many types of human cancer cells, as compared to little or no expression on the cell surface of normal human cells. Sometimes N-acetylglucosamine and N-acetyl-galactosamine, are highly expressed in cancer cells (e.g., FIG. 2A: Hep-G2 cells). Accordingly, N-acetylglucosamine and N-acetyl-galactosamine may serve as biomarkers or potential therapeutic targets for the treatment of cancer. Similarly, other saccharide-relating biological targets or markers relating to cancers and other diseases (e.g., inflammation) may be easily identified by looking for binding of other lectins specific for other saccharides characteristic for other diseased tissues and comparing them with healthy tissues of humans, animals, or various tumor cell lines as illustrated above.

Example 2: Generation of Monoclonal Antibodies Recognizing N-acetylglucosamine and N-acetyl-galactosamine The above results demonstrate the unexpected findings that N-acetylglucosamine and/or N-acetyl-galactosamine are preferentially expressed in a range of human cancerous tissues and cell lines but show little or no expression in most normal human tissues. Therefore, methods for diagnosis of cancers may be developed by detecting the presence of N-acetylglucosamine and/or N-acetyl-galactosamine, using molecules capable of binding to N-acetylglucosamine and/or N-acetyl-galactosamine in a biological sample of a subject suspected of having a cancer. In addition, agents that bind and inhibit the growth of a cancerous cell expressing N-acetylglucosamine and/or N-acetyl-galactosamine, or agents that inhibit pathways relating to expression of N-acetylglucosamine and/or N-acetyl-galactosamine may serve as potentially useful in the treatment and/or prevention of cancers. To meet this goal, described herein are monoclonal antibodies that specifically recognize N-acetylglucosamine and/or N-acetyl-galactosamine.

Mice were immunized with a mixture of lysates from human tumor cell lines representing lung carcinoma (A549), hepatocarcinoma (HEP-G2), and colon carcinoma (SW11/b). Hybridomas were generated and antibodies selected as described above.

Monoclonal antibodies obtained included 1B3E12, 3C4F12, 7E6A10, 1C5C9, 2F7H4, 7C10H11, 4C8C12, 7E6C12, 4E10, 8D9B12, 7G1E12 and 4H6H7. Those monoclonal antibodies were tested for their specificity to N-acetylglucosamine, N-acetyl-galactosamine, and human tumor antigens using the ELISA assay described above. Antibodies were tested for reactivity against tumor lysates from various human tumor cell lines included SMMC-7721 (hepatocarcinoma), NCI-H446 (small cell lung cancer), SPC-A-1 (lung adenocarcinoma), MCF-7 (Breast carcinoma), SW11/b (Colon carcinoma), and ECAP-1090 (Esophageal adenocarcinoma). Samples were scored based on $OD_{450\ nm}$ as described in Table 2.

TABLE 2

| ELISA Result | $OD_{450}$ |
| --- | --- |
| Negative (−) | <0.25 |
| Between (±) | 0.25-0.30 |
| Positive (+) | 0.31-0.49 |
| Positive (2+) | 0.50-0.75 |
| Positive (3+) | 0.76-0.99 |
| Positive (4+) | ≥1.00 |

The results of the ELISA based screening are shown in FIG. 3. These results demonstrate that monoclonal antibodies 1B3E12, 3C4E12, 7E6A10, 1C5C9, 2F7H4, 7C10H11, 4C8C12, 7E6C12, 8D9B12 and 7G1E12 bind to N-acetylglucosamine and N-acetyl-galactosamine. It is possible that those monoclonal antibodies also bind to glycoconjugates bearing distinct N-Acetyl glucosamine or N-acetyl-galactosamine. In addition, some monoclonal antibodies are capable of binding human tumor antigens, as shown in FIG. 3. Without wishing to be bound to theory, these results may suggest that the tumor antigens listed in FIG. 3 either include N-acetylglucosamine and/or N-acetyl-galactosamine, or include glycoconjugates bearing distinct N-Acetyl glucosamine or N-acetyl-galactosamine moieties. These results illustrate the generation of novel monoclonal antibodies that recognize N-acetylglucosamine and/or N-acetylglucosamine.

Example 3: Monoclonal Antibodies Recognizing N-Acetyl-Glucosamine and N-Acetyl-Galactosamine Inhibit Cancer Cell Growth In Vitro The previous Example demonstrates the generation of monoclonal antibodies that recognize N-acetylglucosamine and/or N-acetyl-galactosamine. These antibodies were subsequently tested for their ability to block the growth of various cancer cell lines in vitro.

To test selected antibodies, the MTT growth assay described above was used to examine how treatment with each antibody affected the proliferation (i.e., growth rate) of human cancer cell lines U251 (glioma), SMMC-7721 (hepatocarcinoma), NCI-H466 (small cell lung cancer), SK-MES-1 (lung squamous cell carcinoma), SPC-A1 (lung adenocarcinoma), MCF-7 (human breast cancer), SKOV-3 (human ovary cancer) and Hela (cervical cancer). In each experiment, antibodies were tested at a range of concentrations (i.e., doses).

FIG. 4 demonstrates the effect of monoclonal antibody 2F7H4 on the proliferation of various human cell lines. At multiple concentration, 2F7H4 inhibited the cellular growth of U251 and SPC-A1 cells by at least 50%. Thus monoclonal antibody 2F7H4 has the potential for the treatment or diagnosis of multiple human cancers, including but not limited to brain tumors, such as glioma, and lung cancers, such as adenocarcinoma.

FIG. 5 demonstrates the effect of monoclonal antibody 1C5C9 on the proliferation of various human cell lines. At multiple concentrations, 1C5C9 inhibited the cellular growth of U251, SK-MES-1 and SPC-A1 cells by at least 50%. Thus monoclonal antibody 1C5C9 has the potential for the treatment or diagnosis of multiple human cancers, including but not limited to brain tumors, such as glioma; liver cancer; and lung cancers, such as lung squamous cell carcinoma and adenocarcinoma.

FIG. 6 demonstrates the effect of monoclonal antibody 3C4F12 on the proliferation of various human cell lines. At multiple concentrations, 3C4F12 inhibited the cellular growth of NC1-H446 and SK-MES-1 cells by at least 50%. Thus monoclonal antibody 3C4F12 has the potential for the treatment or diagnosis of multiple human cancers, including but not limited to lung cancers, such as small cell lung cancer and lung squamous cell carcinoma.

Figure 7:
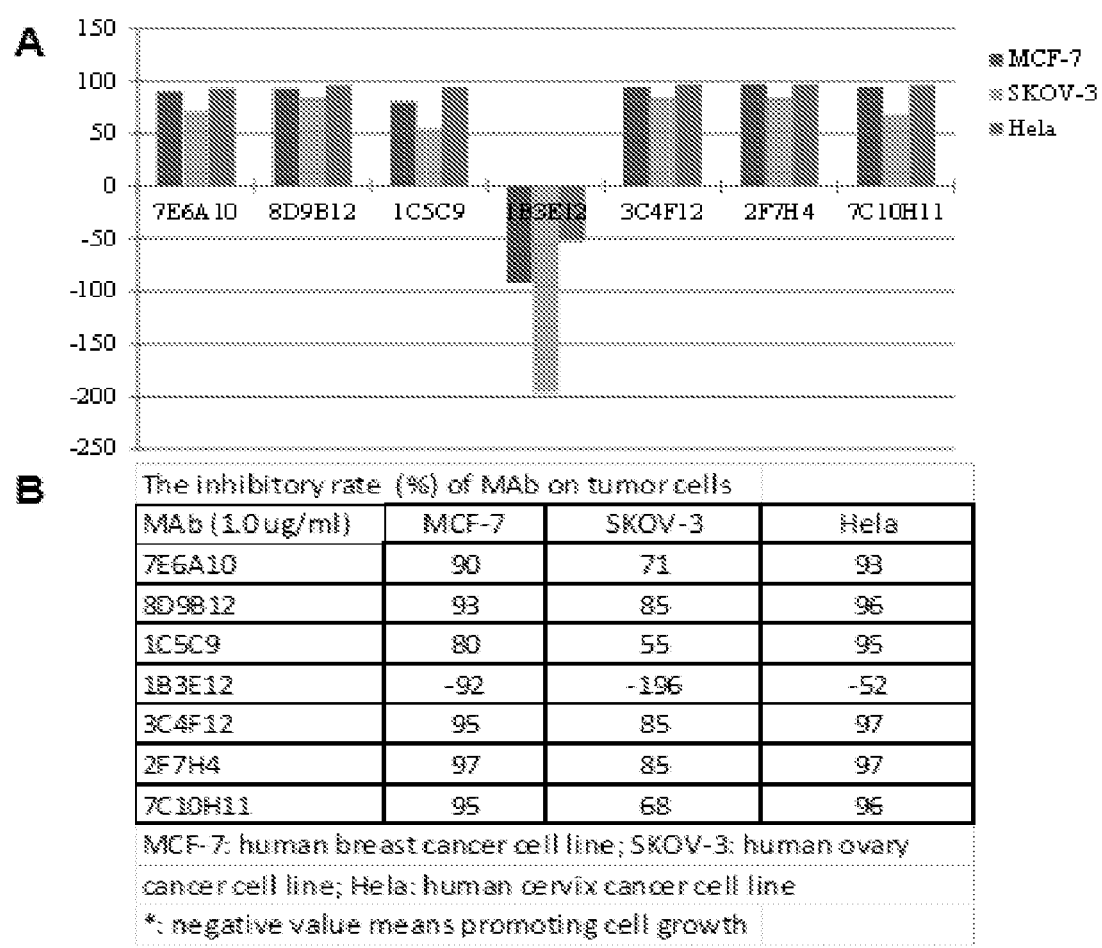
FIG. 7 shows the effect of various monoclonal antibodies (at a concentration of 1.0 µg/mL) on growth inhibition of MCF-7, SKOV-3, and Hela human cancer cell lines (graph is shown in A; table is shown in B). Values refer to the percentage of growth inhibition observed with antibody treatment, and a negative value means growth rate was increased in response to antibody treatment.

FIG. 7 shows the effect of various monoclonal antibodies on the growth rate of MCF-7 (breast cancer), SKOV-3 (ovarian cancer), and Hela (cervical cancer) human cancer cell lines. These results demonstrate that monoclonal antibodies 7E6C12, 8D9B12, 1C5C9, 3C4F12, 2F7H4 and 7C10H11 inhibited over 50% of the cellular growth of MCF-7, SKOV-3, and Hela cells when given at 1.0 µg/ml. Thus these monoclonal antibodies have the potential for the treatment or diagnosis of human breast cancer, ovarian cancer, and cervical cancer. In addition, monoclonal antibody 1B3E12 promoted cellular growth of the three tumor cell lines. Although monoclonal antibody 1B3E12 may not be suitable for the treatment of these three cancers, it may be useful in the diagnosis of these cancers.

Figure 8:
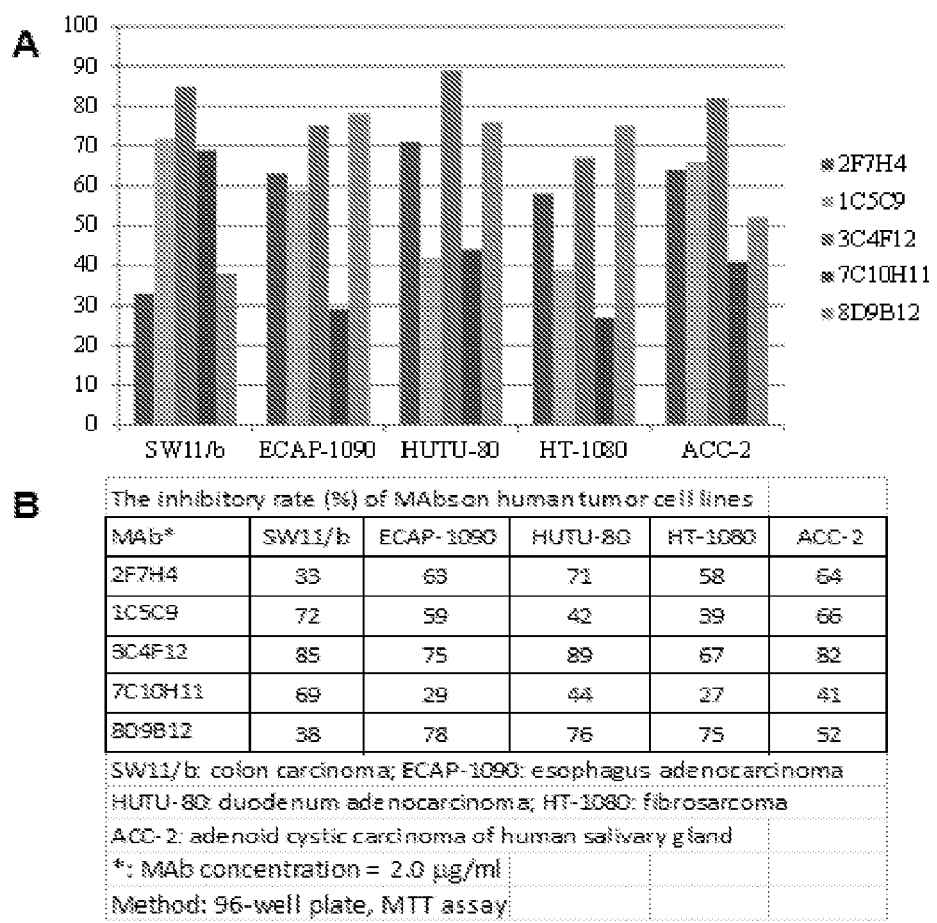
FIG. 8 shows the effect of various monoclonal antibodies (at a concentration of 2.0 µg/mL) on growth inhibition of SW11/b, ECAP-1090, HUTU-80, HT-1080 and ACC-2 human cancer cell lines (graph is shown in A; table is shown in B). Values refer to the percentage of growth inhibition observed with antibody treatment.

FIG. 8 shows the effect of various monoclonal antibodies on the growth rate of SW11/b (colon carcinoma), ECAP-1090 (esophageal adenocarcinoma), HUTU-80 (duodenum adenocarcinoma), HT-1080 (fibrosarcoma) and ACC-2 (adenoid cystic carcinoma of salivary gland) human cancer cell lines. These results demonstrate that monoclonal antibodies 2F7H4, 1C5C93C4F12, 7C10H11 and 8D9B12 inhibited over 50% of the cellular growth of SW11/b, ECAP-1090, HUTU-80, HT-1080, and ACC-2 cells, respectively, when given at 2.0 µg/ml. Thus these monoclonal antibodies have the potential for the treatment, or diagnosis of human esophageal cancer, duodenum cancer, fibrosarcoma and salivary gland cancer.

As a whole, these results demonstrate that multiple monoclonal antibodies that recognize epitopes containing N-acetylglucosamine and/or N-acetyl-galactosamine are able to bind and inhibit the growth of various human cancer cells.

Example 4: Monoclonal Antibody Binding N-Acetyl-Galactosamine and N-Acetyl Galactosamine Inhibits Cancer Cell Growth In Vivo The ability of monoclonal antibodies that recognize epitopes containing N-acetylglucosamine and/or N-acetyl-galactosamine to inhibit cancer growth was next tested in an in vivo model.

Figures 9, 10:
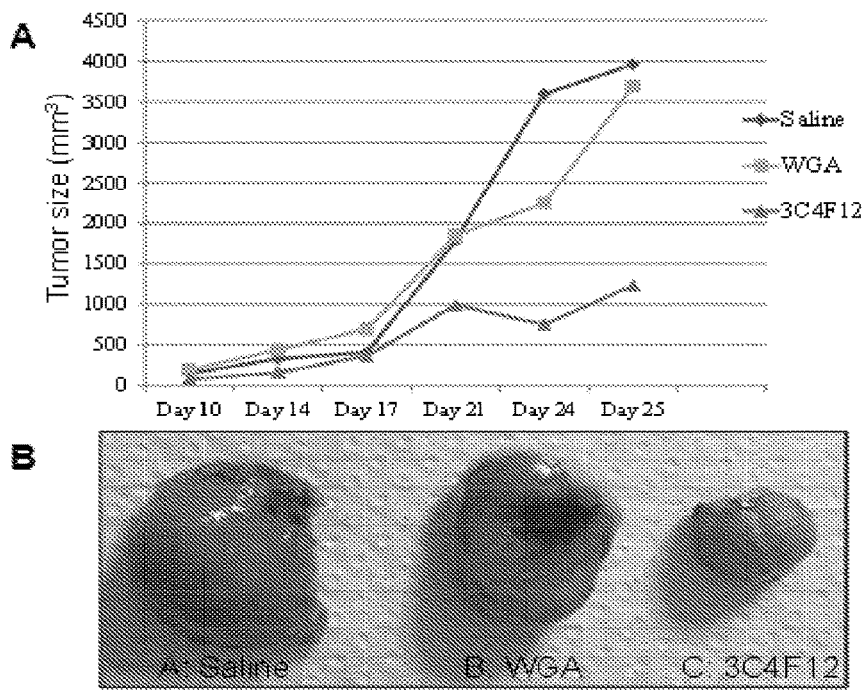
FIG. 9 shows the effect of antibody 3C4F12 on tumor size using an in vivo tumor xenograft model. (A) Tumor xenograft size plotted over time in animals treated with saline, wheat germ agglutinin (WGA), or 3C4F12. (B) Images of tumor xenografts treated with saline, wheat germ agglutinin (WGA), or 3C4F12.
FIG. 10 demonstrates an ELISA-based assay for the detection of cancer-correlated antigens in serum samples from patients with various types of cancer using monoclonal antibody 1C5C9. The system for grading samples is described in Table 3.

The human cancer cell xenograft model described above was used to test the inhibitory efficacy of the monoclonal antibodies of the present disclosure on tumor cell growth. The results are shown in FIG. 9. WGA and saline had similar effects, with both failing to inhibit the growth of the tumor xenografts. In contrast, monoclonal antibody 3C4F12 was able to significantly inhibit the growth of the tumor xenografts, particularly as xenograft growth accelerated after day 17 (FIG. 9A). This inhibition of growth rate was reflected in the overall size of the tumor xenografts, as the xenograft treated with 3C4F12 displayed a much smaller size than those treated by saline or WGA (FIG. 9B).

Importantly, these results demonstrate that a monoclonal antibody that recognizes N-acetylglucosamine and N-acetyl-galactosamine is able to inhibit the growth of cancer cells in vivo. Combined with the in vitro data using human cell lines, these results suggest that monoclonal antibodies that recognize N-acetylglucosamine and/or N-acetyl-galactosamine may be widely useful in treating multiple human cancer types in vivo.

Example 5: Use of Monoclonal Antibody Recognizing N-acetylglucosamine and N-Acetyl Galactosamine in ELISA-Based Blood Test for Cancer The previous Examples describe how monoclonal antibodies that recognize N-acetylglucosamine and/or N-Acetyl. Galactosamine be used to bind human cancer cells, which are characterized by high levels of surface expression of these sugars. Since these moieties are preferentially expressed not only on or in cancer cells, but are also released into body fluid (e.g., including blood or other secretions), the following Example demonstrates how this property may be used not only in preventing and/or treating cancer as illustrated above, but also in diagnosing cancer in patients.

Monoclonal antibody 1C5C9 was tested using the ELISA-based assay described above for detecting antigen in patient blood samples. The grading metric for these assays is provided in Table 3.

TABLE 3

| Grade | OD$_{450}$ |
| --- | --- |
| Negative (−) | <0.25 |
| Between (±) | 0.25-0.30 |
| Positive (+) | 0.31-0.49 |
| Positive (2+) | 0.50-0.75 |
| Positive (3+) | 0.76-0.99 |
| Positive (4+) | ≥1.00 |

As shown in FIG. 10, less than 3% of the blood samples from healthy subjects had distinct levels of N-acetylglucosamine or N-acetyl-galactosamine (or molecules bearing N-acetylglucosamine or N-acetyl-galactosamine) in their blood, whereas 79.3%, 70.6% 66.7%, and 50.0% of the blood samples from patients with breast cancer, lung cancer, colon cancer and thyroid cancer, respectively, had distinct levels of N-acetylglucosamine or N-acetyl-galactosamine for molecules bearing N-acetylglucosamine or N-acetyl-galactosamine).

These data indicate that monoclonal antibodies recognizing saccharide-related biomarkers of the present disclosure may be used for detection of the saccharide-related biomarkers that are differentially expressed in various cancers and released to blood and other body fluid or secretions. Therefore, the antibodies described herein may be highly useful in diagnostic assays, e.g., those based on ELISA, for diagnosing the presence of cancer cells in a tissue sample (e.g., blood). Other methods well known in the art for diagnostic use with the antibodies described herein may include but not limited to immuno-colloidal cold assays.

Example 6: Use of Monoclonal Antibodies that Specifically Bind N-acetylglucosamine and/or N-acetyl-galactosamine in a Flow Cytometry-Based Blood Test for Cancer Since the moieties such as N-acetylglucosamine and/or N-acetyl-galactosamine are preferentially expressed on cancer cells, the following Example demonstrates how this property may be used not only in preventing and/or treating cancer as illustrated above, but also in diagnosing cancer in patients.

Monoclonal antibodies 2F7H4 (FIG. 11), 1C5C9 (FIG. 12) and 1B3E12 (FIG. 13) were tested using the flow cytometry-based assay described above for detecting circulating cancer cells in patient blood samples. The grading metric for these assays is provided in FIGS. 11-13. It should be noted that this assay detects cancer cells existing in the peripheral blood. Without wishing to be bound to theory, if a cancer cell does not go into peripheral blood circulation, it may not be detected, and thus a negative result may not necessarily indicate the absence of cancer in the individual.

FIG. 11 demonstrates the results of a flow cytometry-based assay with monoclonal antibody 2F7H4. All of the PBMCs from ten healthy individuals had less than 2.2% of the cells with distinct levels of N-acetylglucosamine or N-acetyl-galactosamine (or molecules bearing N-acetylglucosamine or N-acetyl-galactosamine) determined by monoclonal antibody 2F7H4, whereas 50%-100% of the PBMCs from patients with lung cancer, liver cancer, breast cancer, colon or colorectal cancer, esophagus cancer, stomach cancer, endometrial cancer cervical cancer, thyroid cancer, brain cancer, lymphoma, respectively, had more than 2.3% of the cells with distinct levels of N-acetylglucosamine or N-acetyl-galactosamine (or molecules bearing N-acetylglucosamine or N-acetyl-galactosamine). Thus monoclonal antibody 2F7H4 has the potential for the diagnosis of multiple human cancers, as described above, especially lung cancers, breast cancers, colon or colorectal cancers, stomach cancers and endometrial cancers.

FIG. 12 demonstrates the results of a flow cytometry-based assay with monoclonal antibody 1C5C9. All of the PBMCs (peripheral mononuclear cells) from ten healthy individuals had less than 3.3% of the cells with distinct levels of N-acetylglucosamine or N-acetyl-galactosamine (or molecules bearing N-acetylglucosamine or N-acetyl-galactosamine) determined by monoclonal antibody 1C5C9, whereas 14%-100% of the PBMCs from patients with lung cancer, liver cancer, breast cancer, colon or colorectal cancer, esophagus cancer, cervical cancer, thyroid cancer, pancreas cancer, respectively had more than 3.4% of the cells with distinct levels of N-acetylglucosamine or N-acetyl-galactosamine (or molecules bearing N-acetylglucosamine or N-acetyl-galactosamine). Thus monoclonal antibody 1C5C9 has the potential for the diagnosis of multiple human cancers, as described above, especially colon or colorectal cancers and liver cancers.

FIG. 13 demonstrates the results of a flow cytometry-based assay with monoclonal antibody 1B3E12. All of the PBMCs (peripheral mononuclear cells) from ten healthy individuals had less than 3.2% of the cells with distinct levels of N-acetylglucosamine or N-acetyl-galactosamine (or molecules bearing N-acetylglucosamine for N-acetyl-galactosamine) determined by monoclonal antibody 1B3E12, whereas 30%-67% of the PBMCs from patients with liver cancer, breast cancer, colon or colorectal cancer, esophagus cancer, ovary cancer, pancreas cancer, respectively, had more than 3.3% of the cells with distinct levels of N-acetylglucosamine or N-acetyl-galactosamine (or molecules bearing N-acetylglucosamine or N-acetyl-galactosamine). Thus monoclonal antibody 1B3E12 has the potential for the diagnosis of multiple human cancers, as described above, especially colon or colorectal cancers and breast cancers.

These data indicate that monoclonal antibodies recognizing saccharide-related biomarkers of the present disclosure may be used for detection of circulating cancer cells in patient blood. The circulating cancer cells differentially express the saccharide-related biomarkers and are released to blood and other body fluid or secretions. Therefore, the antibodies described herein may be highly useful in diagnostic assays, e.g., those based on flow cytometry, for diagnosing the presence of cancer cells in a tissue sample (e.g., blood). It is to be noted that some antibodies that fail to inhibit cancer cell proliferation may still be useful for detection methods. For example, monoclonal antibody 1B3E12 of the present invention promoted cellular growth of tumor cell lines of breast cancer, ovary cancer and cervix cancer but was useful in diagnosis of various cancers by flow cytometry.

Example 7: Use of Monoclonal Antibodies that Specifically Bind N-acetylglucosamine and/or N-acetyl-galactosamine for Prevention and Treatment of Gastrointestinal Disease N-acetylglucosamine has been studied as a biomarker of inflammation (e.g., intestinal inflammation caused by rotavirus infection; see PCT/US2009/039810). However, the role of N-acetylglucosamine in inflammation and whether it may serve as a potential therapeutic target for gastrointestinal disease are unknown. Therefore, an antibody that specifically binds to N-acetylglucosamine and N-acetyl-galactosamine was tested for the prevention and treatment of acute infectious gastroenteritis of newborn piglets.

First, monoclonal antibody 1C3C9 (MAb-1C5C9) was tested for binding to inflamed intestinal cells induced by rotavirus infection. Two groups of sucking blab/c mouse pups were treated at day 2 after birth via oral administration of Rhesus rotavirus (RRV) (RRV infected group). The course of this viral illness is typically such that within week 1 after RRV infection, the pups have diarrhea with alcoholic stool, fail to eat well and gain weight as quickly as healthy mice, with 30-40% of pups that show serious illness becoming jaundiced. By the 2nd week all the mice typically become jaundiced and fail to eat well and gain weight, with 80% of pups that show serious illness having died. Viruses are usually cleared within 5 days and undetectable at day 5. Pups were sacrificed at different days after treatment and samples of sear, snap-frozen and formalin-fixed tissues of intestine and liver, were processed. The intestinal tissue sections from mice infected with RRV at day five were stained in immunofluorescence assays with antibody 1C5C9 (MAb-1C5C9) and fluorescence-conjugated anti-mouse-IgG was used as secondary reagent. The intestinal tissue sections from healthy mice without RRV infection were used as control.

FIG. 14 shows that MAb-1C5C9 strongly bound to the inflammatory cells from a tissue section of a mouse infected with rotavirus (FIG. 14B). In contrast, MAb-1C5C9 did not bind to an intestinal tissue section of a healthy mouse without rotavirus infection (FIG. 14A), These data indicated that monoclonal antibodies recognizing epitopes containing N-acetylglucosamine acid/or N-acetyl-galactosamine are able to bind inflammatory cells in the intestine.

In an outbreak, an acute infectious gastroenteritis caused by a porcine epidemic diarrhea virus (PEDV) infection attacked newborn piglets at age 1-5 days. 100% of newborn piglets were infected and 80-90% of infected piglets died. There were no effective therapeutics for the infection.

Figure 15:
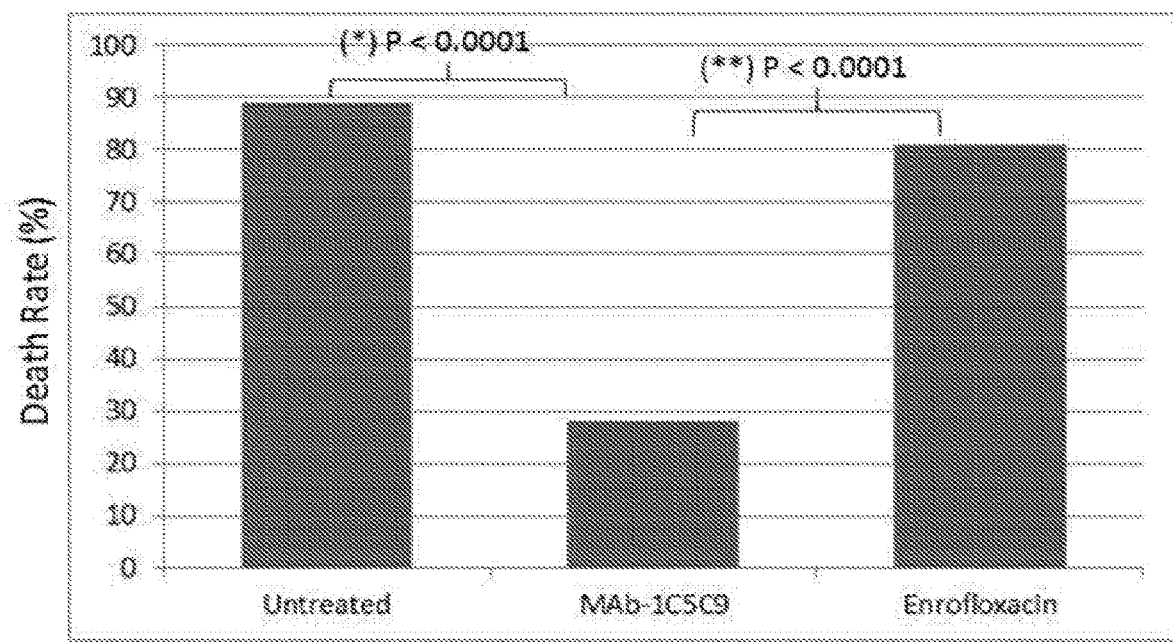
FIG. 15 compares the death rate (expressed as a percentage) of piglets exposed to a porcine epidemic diarrhea virus (PEDV) upon treatment with MAb-1C5C9 or enrofloxacin, as compared to untreated controls. The statistical significance of the death rates observed with each treatment, as compared to MAb-1C5C9 treatment, are shown.

To test the efficacy of MAb-1C5C9 in preventing viral infection, when a few piglets (1-2 of piglets) were observed to be infected in a litter, a single dose of MAb-1C5C9 (50 µg) was orally administered to all the uninfected piglets in the same litter. About 500 of piglets were treated with MAb-1C5C9. None of the uninfected piglets treated with MAb-1C5C9 were infected or died. The death rate of the litters with MAb-1C5C9 treatment (N=500) was about 28%; the death rate of the litters with enrofloxacin treatment (N=500) was about 81%; and the death rate of the litters untreated (N=500) was 89%. The efficacy of MAb-1C5C9 in reducing death rate showed statistical significance with a p-value<0.0001 when compared to antibiotics (enrofloxacin) or to those piglets which are left untreated (FIG. 15).

These results indicate that MAb-1C5C9 is effective and better than antibiotics for the prevention of gastroenteritis caused by viral infections (including but not limited to PEDV infection and other intestinal viruses).

The efficacy of MAb-1C5C9 in treating gastrointestinal disease was also tested in a human. A 55 years old female (~58 kg) suffered from intestinal inflammation with diarrhea, bloody stool, and abdominal pain for four weeks. Colonoscopy showed no abnormality except hemorrhoids. Treatment with antibiotic (Ciprofloxacin) for one week was not effective.

Oral administration of the MAb-1C5C9 (2-3 µg/kg, 0.13 mg/dose) once per day was given for 10 days. The bloody stool was reduced after 2 doses, stopped after 5 doses; the diarrhea was stopped after 7 doses; and the patient was recovered after 10 days of the treatment. There were no recurrence of either the intestinal inflammation or the hemorrhoids within 7 months after the treatment.

These results indicate that MAb-1C5C9 is effective and better than antibiotics for the treatment of inflammatory bowel disease and hemorrhoids. Taken together, these results demonstrate that antibodies that specifically bind to N-acetylglucosamine and N-acetyl-galactosamine may be used to treat a range of gastrointestinal diseases, such as inflammatory diseases including viral infection, inflammatory bowel disease, and hemorrhoids.

Example 8: Testing Humanized Antibodies that Specifically Bind N-acetylglucosamine and/or N-acetyl-galactosamine in a Mouse Model of IBD The previous Examples demonstrated the efficacy of MAb-1C5C9 in inhibiting cancer cell growth, detecting circulating cancer cells, and treating IBD. Mab-1C5C9 was subsequently humanized. The following Examples describe variants of humanized 1C5C9 with a common heavy chain variable region (VH) and different light chain variable regions (VK). Humanized 1C5C9 antibodies were tested for efficacy, binding, and toxicity in multiple in vivo animal models of IBD.

Materials and Methods

Binding of Humanized Antibodies to N-acetyl-galactosamine (NAG)

100 µL of NAG was coated onto the wells of a 96-well plate at the concentration of 1 µg/mL for overnight, washed and blocked. 5 humanized antibody clones were tested and compared to chimeric 1C5C9 antibody. After adding the test antibodies to the plate, the plate was washed, and binding was detected by HRP-conjugated anti-human IgG as a secondary reagent. HRP was detected by standard chromogenic assay, and binding was assayed by $OD_{450}$ nm.

Mouse IBD Model

Acute colitis was induced in BALB/c female mice, aged 6-8 weeks and weighing 17-19 grams, by anal administration of a 0.15 ml, dose of 120 mg/mL trinitrobenzenesulphonic acid (TNBS; Sigma-Aldrich) in 50% ethanol. Mice were divided into 5 treatment groups as follows:

G1: untreated (n=6);
G2: treated with 5 µg antibody 1C5-VK2 per animal, intraperitoneally (IP) (n=6);
G3: treated with 5 µg antibody 1C5-VK2 per animal, orally (PO) (n=6);
G4: treated with 2 µg antibody 1C5-VK2 nor animal, intraperitoneally (IP) (n=6); and
G5: treated with 5 µg antibody 1C5-VK1 per animal, intraperitoneally (IP) (n=6).

The treatment of G2-G5 mice was dosed once per day for 4 days from 48 hours after induction of IBD by TNBS.

Body weight and clinical signs of mice in each group were recorded each day of the course of the IBD model. Two mice from the control group (G1) were sacrificed at 48 hours after the induction of the IBD model by TNBS, and whole colon tissues were collected. One day (24 hrs) after the last dosing, the procedure was ended for all animals (day 7 of the course). Whole colon tissue was collected for gross pathology (colon weight, ulceration) and histology evaluation (standard HE staining of colon tissue sections) according to the key shown in FIG. 18, and representative images were taken. Colon tissue pathology was evaluated using standard histological methods as shown in FIG. 20A.

Figure 20:
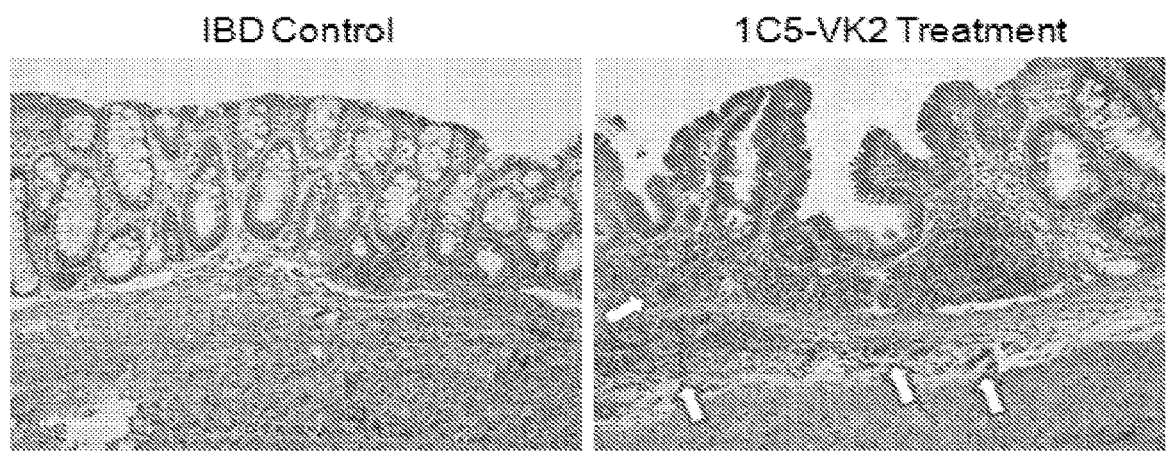
FIG. 20 shows immunohistochemical (IHC) staining of colon sections in mice treated with humanized 1C5-VK2 antibody, as compared to control mice. Tissues were obtained from mice at one week of the IBD model and stained with anti-human IgG-HRP. Arrows indicate detection of 1C5-VK2 antibody at sites of colon inflammation.

The localization of antibody 1C5-VK2 in treated mice was also assessed using colon tissue sections and standard immunohistochemical methods (HE staining) with HRP-conjugated anti-human IgG as a detection reagent. Representative images of group G2-mice are compared with control mice as shown in FIG. 20.

Figure 16:
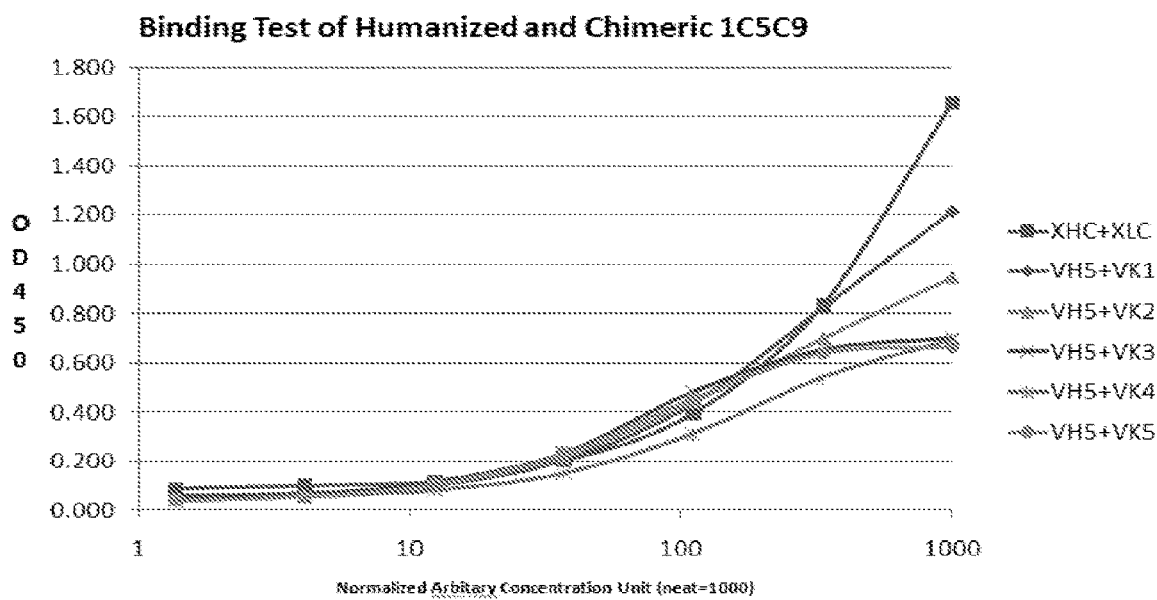
FIG. 16 shows binding of humanized 1C5C9 antibodies to N-acetylglucosamine (NAG), as determined by ELISA. Antibodies tested included: chimeric 1C5C9 ("XHC+XLC"), humanized 1C5-VK1 ("VH5+VK1"), humanized 1C5-VK2 ("VH5+VK2"), humanized 1C5-VK3 ("VH5+VK3"), humanized 1C5-VK4 ("VH5+VK4"), and humanized 1C5-VK5 ("VH5+VK5").

Results 5 humanized 1C5C9 clones were assayed for binding to NAG and compared to a chimeric 1C5C9 antibody (i.e., the parental mouse variable domains attached to a human Fc region). FIG. 16 shows that all antibodies displayed dose-dependent binding to NAG. Humanized antibodies 1C5-VK1 and 1C5-VK2 were selected for further characterization.

Acute colitis was induced in mice as described above, and the effect of humanized 1C5-VK2 administration on body weight, clinical signs such as diarrhea, and colon condition was tested. The effect of antibody treatment was assayed by macroscopic assessment of colon conditions according to the key provided in FIG. 17. Colons from mice in treatment groups G1-G4 were assessed for the presence of colitis, as shown in Table 4 below.

TABLE 4

Frequency of colitis in antibody-treated mice, as compared to untreated controls.

| Group | # of animals with colitis | # of animals without colitis |
|---|---|---|
| G1 | 6 | 0 |
| G2 | 2 | 4 |
| G3 | 6 | 0 |
| G4 | 6 | 0 |

Figure 17:
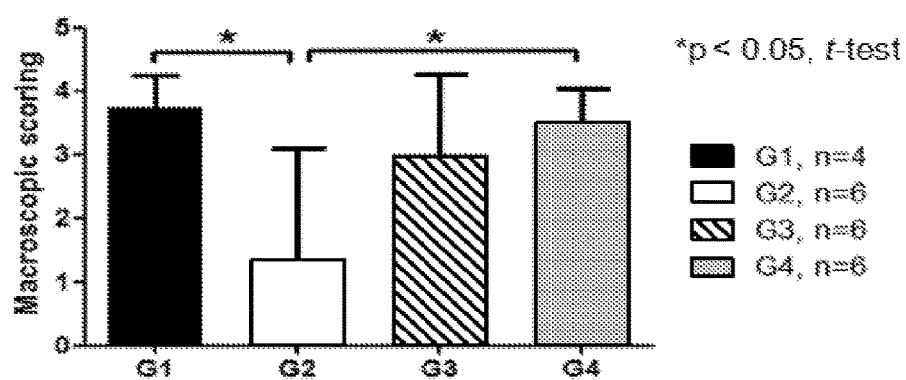
FIG. 17 shows the effect of humanized 1C5-VK2 antibody on intestinal morphology in a mouse IBD model induced by TNBS as judged by macroscopic assessment conducted on day 7. Treatment groups include G1: untreated (n=4); G2: 5 µg 1C5-VK2/animal, intraperitoneal (IP) (n=6), G3: 5 µg 1C5-VK2/animal, oral (PO) (n=6), and G4: 2 µg 1C5-VK2/animal, intraperitoneal (IP) (n=6). *indicates p<0.05 by t-test (comparisons were between the treatment group G2 and the untreated control group G1, and between the treatment group G2 and the treatment group G4).

FIG. 17 shows that treatment with 1C5-VK2 resulted in a significant decrease in score as compared to untreated controls demonstrating that antibody treatment resulted in significant mitigation of ulceration and inflammation.

Figure 18A:
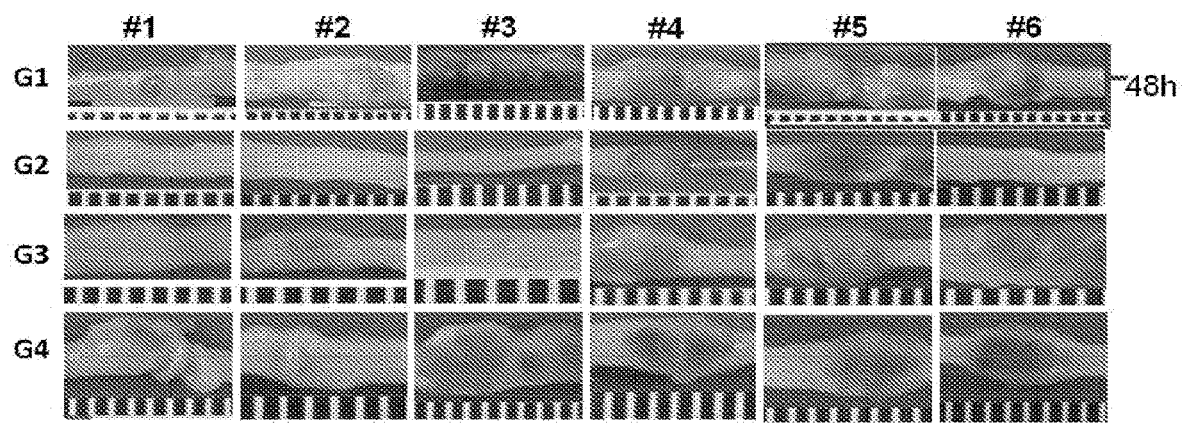
FIG. 18A shows representative gross images taken at day 7 of the IBD model induced by TNBS. Treatment with humanized 1C5-VK2 antibody was given at 48 hours after the induction of the IBD model. Treatment groups are as described above for FIG. 17. The colon conditions before treatment are shown by the images taken from samples isolated at 48 hours after induction of the IBD model, as indicated.

Representative gross images taken from these colon samples are shown in FIG. 18A. All the untreated mice of control group ((ii) showed serious colitis with severe ulceration, inflammation, and tissue necrosis. In group G2, one sample (#1) showed thickening of the bowel wall without ulceration and inflammation, while 3 samples (#2, 3, and 6) showed no ulceration and inflammation. The remaining two cases showed ulceration and inflammation. In group G3, three cases (#1, 2, and 4) showed thickening of the bowel wall without ulceration and light inflammation. These results illustrate that 1C5-VK2 treatment resulted in significant mitigation of ulceration and inflammation.

Figure 18B:
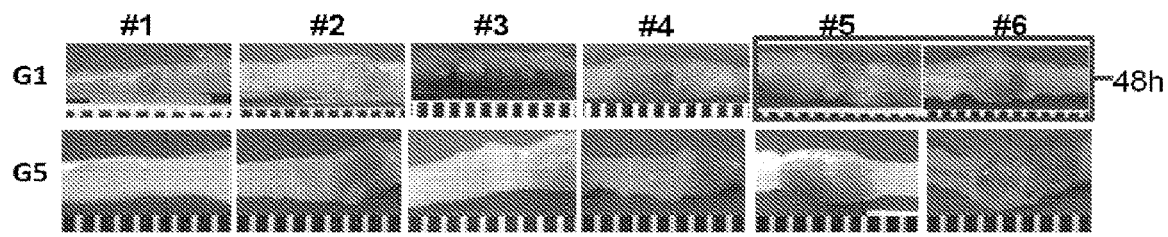
FIG. 18B shows representative gross images taken at day 7 of the IBD model. Treatment with humanized 1C5-VK2 antibody was given at 48 hours after the induction of the IBD model. Treatment groups include G1: untreated; and G5: 5 µg 1C5-VK1/animal, intraperitoneal (IP). The colon conditions before treatment are shown by the images taken from samples isolated at 48 hours after induction of the IBD model, as indicated.

The effect of 1C5-VK1 antibody treatment in this mouse IBD model was also tested. As shown in FIG. 18B, representative gross images demonstrated that 5 out of 6 animals in the G5 treatment group showed improvement of colitis, as compared to untreated G1 controls. These results illustrate that 1C5-VK1 treatment also resulted in mitigation of ulceration and inflammation.

Figure 19A:
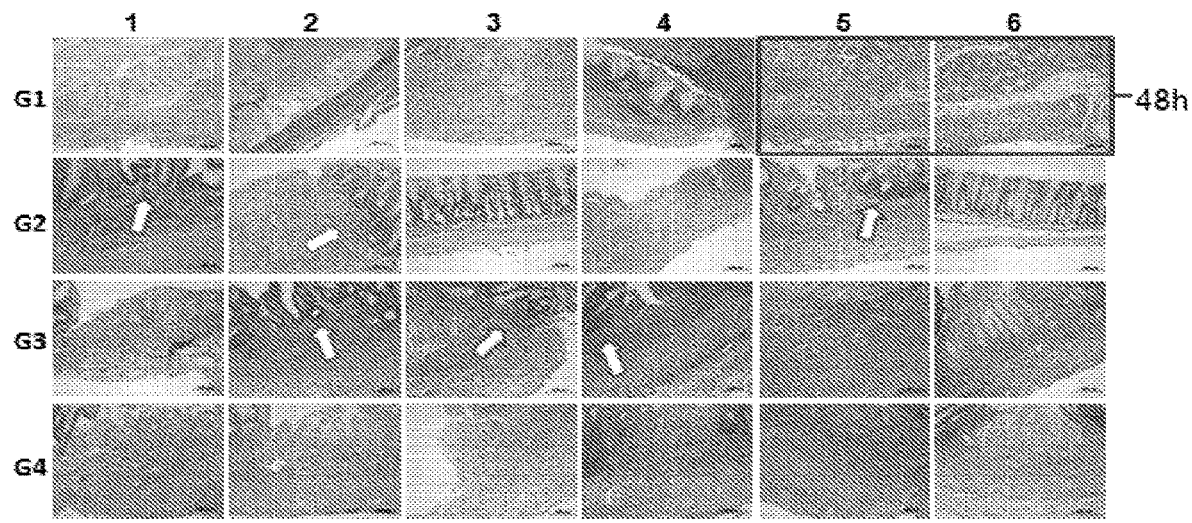
FIG. 19A shows histological images taken at day 7 of the IBD model. Treatment with humanized 1C5-VK2 antibody was given at 48 hours after the induction of the IBD model. Treatment groups are as described above for FIG. 17. Arrows indicate intestinal epithelial regeneration. The colon conditions before treatment are shown by the images taken from samples isolated at 48 hours after induction of the IBD model, as indicated.

Next, representative pathology images were obtained via histochemical preparation (HE staining) of colon tissue sections as described above. FIG. 19A shows representative images from mice treated with 1C5-VK2 in groups G1-G4. All the untreated mice of control group (G1) showed serious ulceration and inflammation without epithelial regeneration. In group G2, two samples (#1 and 2) showed epithelial regeneration and covering of the ulcer, and one sample (#5) showed partial epithelial regeneration (depicted by arrows). Samples 3 and 6 did not show ulceration and inflammation, with only 1 sample (44) showing ulceration and inflammation. In group G3, four samples (#1-4) showed epithelial regeneration and covering of the ulcer (arrows). These images demonstrate that treatment with 1C5-VK2 mitigated IBD pathology, with 5/6 (83%) of the mice treated via IP injection and 4/6 (67%) of the mice treated via oral administration (PO) showing significant mitigation of ulceration and inflammation.

Figure 19B:
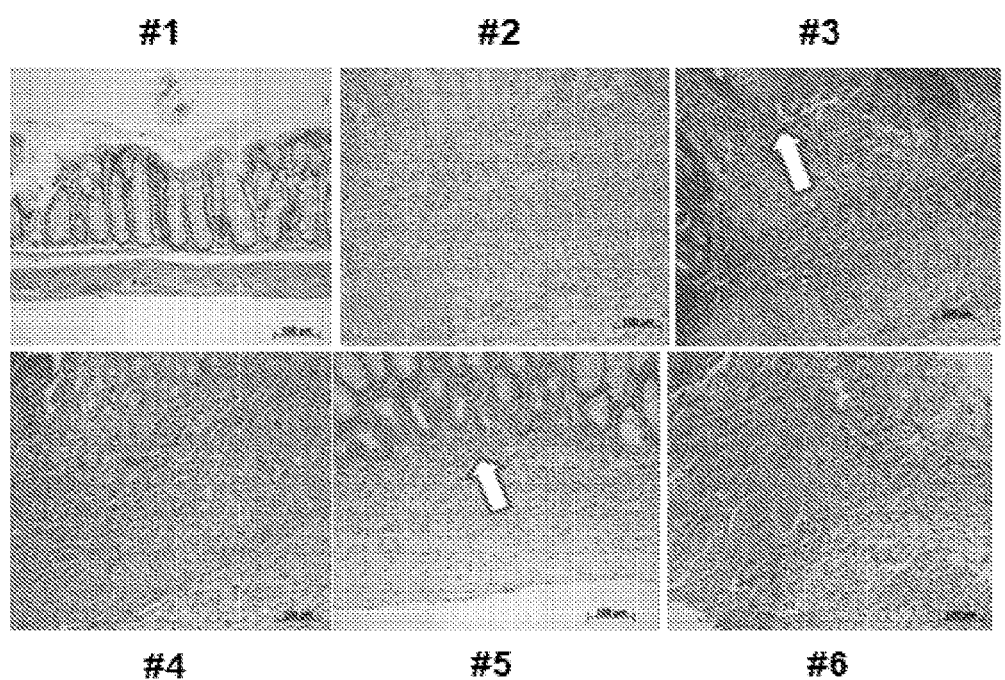
FIG. 19B shows histological images taken at day 7 of the IBD model. Treatment with humanized 1C5-VK1 was given at 48 hours after the induction of the IBD mode. All samples are from treatment group G5: 5 µg 1C5-VK1/animal, intraperitoneal (IP). Arrows indicate intestinal epithelial regeneration.

FIG. 19B shows representative histochemical images from mice treated with 1C5-VK1 in group G5. In group G5, three samples showed recovery (#1) or epithelial regeneration (#3 and 5, as highlighted by arrows). Two samples (#2 and 4) also showed reduced inflammation. These images demonstrate that 5/6 (83%) of the mice treated with 1C5-VK1 also displayed mitigated IBD pathology. In addition, the histological data in FIG. 19A and FIG. 19B indicated that antibodies 1C5-VK1 and 1C5-VK2 can promote intestinal epithelium regeneration.

Localization of 1C5-VK2 antibody in treated mice at day 7 was also assayed using the immunohistochemical methods described above. FIG. 20 shows that 1C5-VK2 was detected on the inflammatory cells (arrows indicating representative staining) and regenerating colon epithelial cells of mice with colitis. This demonstrates that 1C5-VK2 localized to the sites of inflammation upon administration.

Example 9: Testing Toxicity and Pharmacokinetics (PK) of Humanized Antibodies that Specifically Bind N-acetylglucosamine and/or N-acetyl-galactosamine in Mouse Materials and Methods
Toxicity Studies BALB/c mice, 8 weeks of age and weighing 22-24 grams, were randomly divided into 4 treatment groups. Each group included 3 male and 3 female mice. Groups were treated as follows:

G1: 1.0 mg/kg (20 µg total dose) 1C5-VK2 dosed once intravenously (IV)
G2: 1.0 mg/kg (20 µg total dose) 1C5-VK2 dosed once orally (PO)
G3, 5.0 mg/kg (100 µg total dose) 1C5-VK2 dosed once intravenously (IV)
G4, 5.0 mg/kg (14.0 µg total dose) 1C5-VK2 dosed once orally (PO)

Mice were observed for 14 days after treatment for body weight. At day 14, colon samples were assayed by macroscopic assessments and histochemical preparation as described above.

Pharmacokinetic (PK) Studies

BALB/c mice, 8 weeks of age and weighing 22-24 grams, were randomly divided into 4 treatment groups. Each group contained 3 male and 3 female mice. Groups were treated as follows:

G1: 1.1 mg/kg (20 µg total dose) 1C5-VK2 dosed once intravenously (IV)

G2: 1.0 mg/kg (20 µg total dose) 1C5-VK2 dosed once orally (PO)

G3: 5.0 mg/kg (100 µg total dose) 1C5-VK2 dosed once intravenously (TV)

G4: 5.0 mg/kg (100 µg total dose) 1C5-VK2 dosed once orally (PO)

Blood was collected from mice at the following time points after treatment: 5 min 0.5 hours, 1 hour, 2 hours, 4 hours, 8 hours, 24 hours, and 2 weeks. Serum was isolated from blood, and 10 µl of serum plus 90 µl of PBS (total of 100 µl) was coated onto the wells of a 96-well plated for overnight. 1C5-VK2 levels in serum were assayed by direct ELISA using HRP-conjugated anti-human IgG as a detecting reagent.

Body weight and clinical signs of mice in each treatment group were recorded every other day. The procedure ended for all animals at day 14. The following organs were collected for histological evaluation: colon, small intestine, stomach, liver, pancreas, heart, lung, kidney, spleen and brain.

Results

Figure 21:
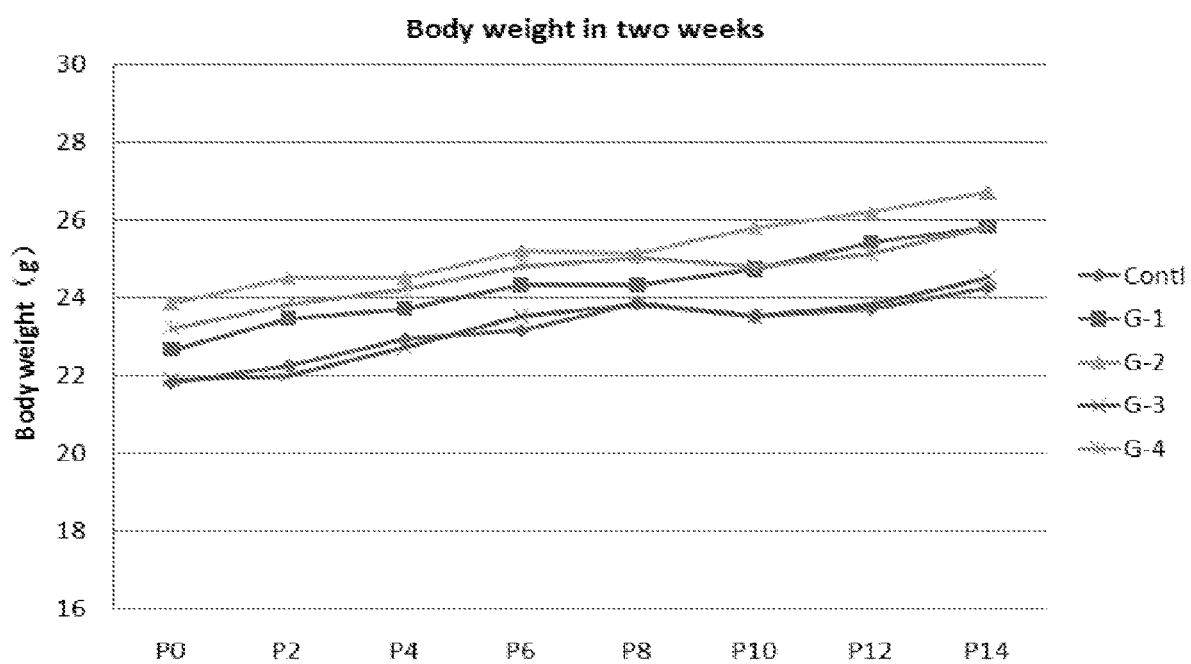
FIG. 21 shows the results of acute toxicity tests on humanized 1C5-VK2 antibody in mice (body weight time). Treatment groups include G1: 1.0 mg/kg, intravenous (IV); G2. 1.0 mg/kg, oral (PO); G3: 5.0 mg/kg, intravenous (IV), and G4: 5.0 mg/kg, intraperitoneal (IP). All groups used a sample size of 6 animals.

The toxicity of 1C5-VK2 treatment was assessed as described above. FIG. 21 shows that treatment with 2 different doses (1.0 mg/kg and 5.0 mg/kg) via 2 different routes (IV and PO) had no significant effect on body weight in mice, as compared to untreated controls. Also, histological evaluation showed that treatment with 2 different doses (10 mg/kg and 5.0 mg/kg) via 2 different routes (IV and PC)) had no significant adverse effect on organ histology in mice, as compared to untreated controls (data not shown). Taken together, no significant adverse reactions were observed upon 1C5-VK2 treatment at 10-50 times the lowest effective dosage (0.1 mg/kg) for mice. The equivalent, lowest effective dosage for human is about 0.005 mg/kg to 0.01 mg/kg.

Figure 22:
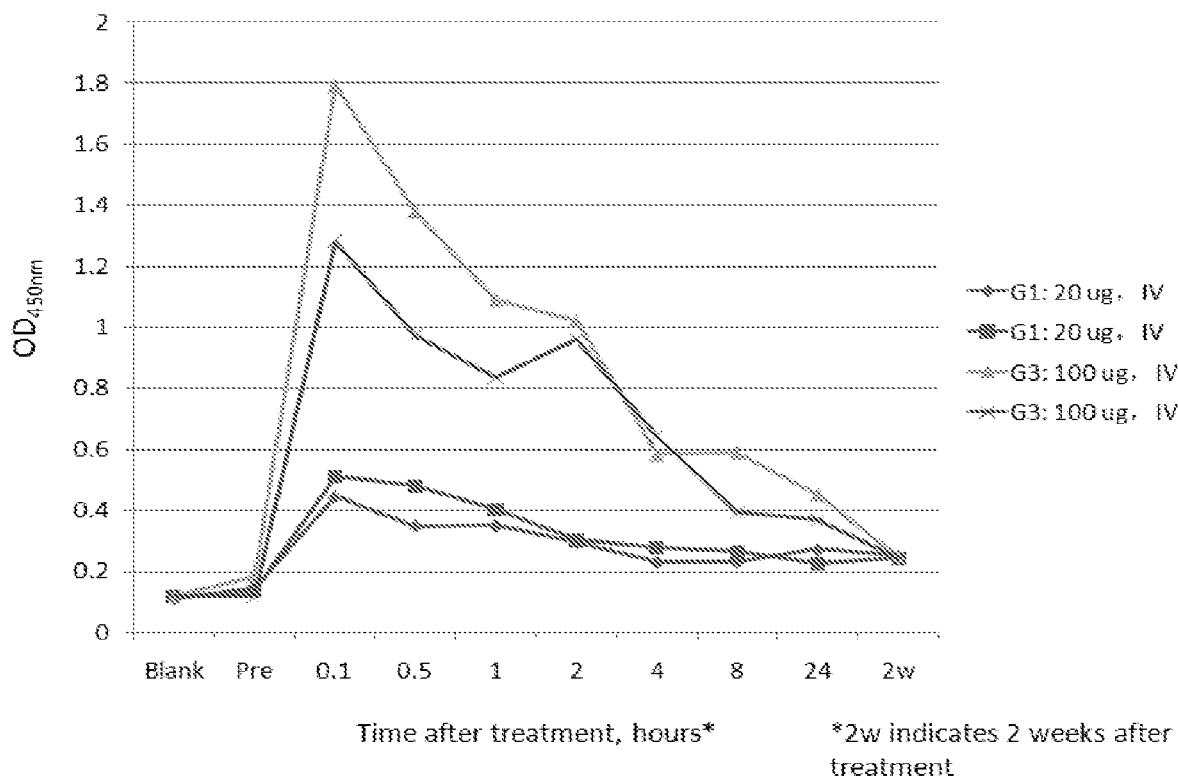
FIG. 22 shows serum levels of humanized 1C5-VK2 antibody in mice treated intravenously, as determined by ELISA. y-axis indicates level of detected antibody ($OD_{450\ nm}$) x-axis indicates time of sample collection after treatment (in hours, except for "2 w," which indicates 2 weeks). Treatment groups and sample sizes are as described above for FIG. 21.
Figure 23:
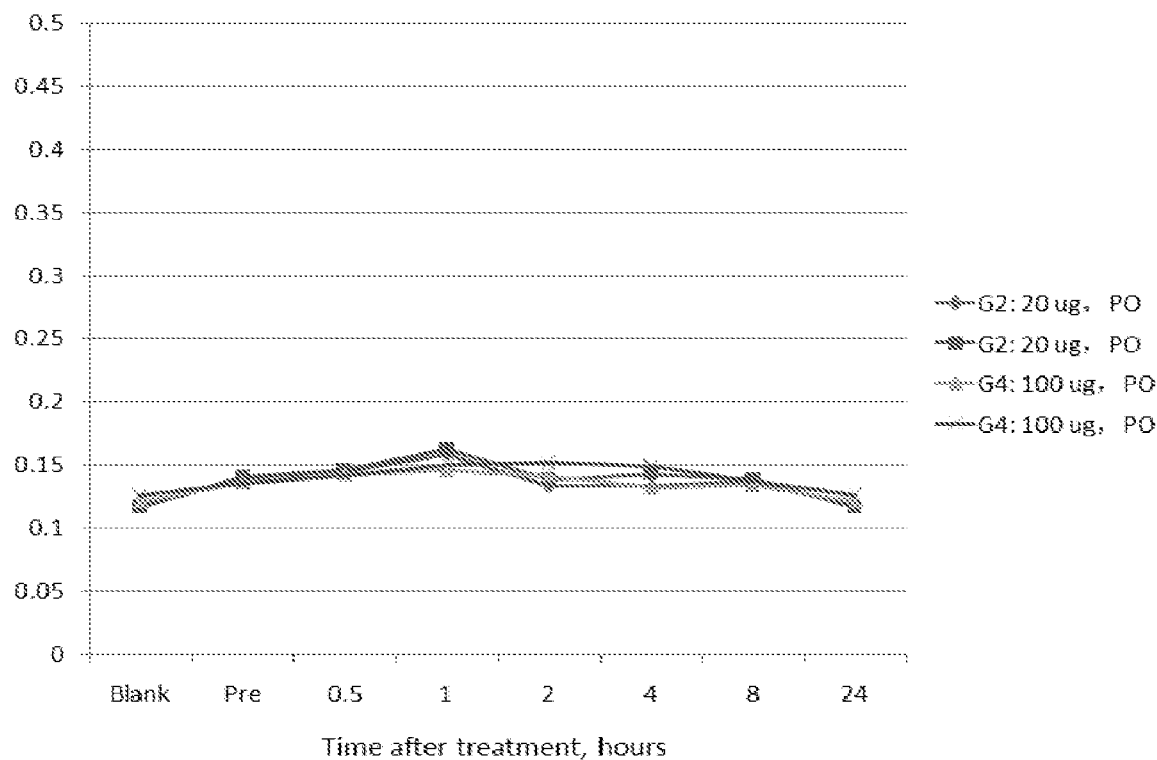
FIG. 23 shows serum levels of humanized 1C5-VK2 antibody in mice treated orally, as determined by ELISA x-axis indicates time of sample collection after treatment (in hours). Treatment groups and sample sizes are as described above for FIG. 21.

The serum PK of 1C5-VK2 administered as described above was also tested by ELBA assay. Results from IV and PO administration are provided in FIG. 22 and FIG. 23, respectively.

Example 10: Testing a Humanized Antibody that Specifically Binds N-acetylglucosamine and/or N-acetyl-galactosamine in a Rat Model of IBD Materials and Methods Acute colitis was induced in SD female rats, aged 9 weeks and weighing 140-160 grams, by anal administration of a 0.25 mL dose of 120 mg/mL trinitrobenzenesulphonic acid (TNBS; Sigma-Aldrich) in 50% ethanol. Rats were divided into 5 treatment groups as follows:

G1: untreated;

G2: treated with human IgG at 125 µg/kg, intraperitoneally (IP);

G4: treated with 1C5-VK2 at 125 µg/kg, intraperitoneally (IP);

G5: treated with 1C5-VK2 at 122 µg/kg, subcutaneously (SC);

G6: treated with 1C5-VK2 at 250 µg/kg, oral gavage (PO).

The treatment of G2-G6 rats was dosed once per day for total of 4 days from 48 hours after induction of IBD by TNBS.

Test articles used are provided in Table 5 below.

TABLE 5

Test articles for rat IBD experiments.

| Group | # of animals | Test article | Original concentration | Route of administration | Dosage |
| --- | --- | --- | --- | --- | --- |
| G1 | 5 | Control | N/A | N/A | N/A |
| G2 | 5 | Human IgG | 10 mg/mL | IP | 125 µg/kg |
| G4 | 5 | 1C5-VK2 | 1.44 mg/mL | IP | 125 µg/kg |
| G5 | 6 | 1C5-VK2 | 1.44 mg/mL | SC | 125 µg/kg |
| G6 | 6 | 1C5-VK2 | 1.44 mg/mL | PO | 250 µg/kg |

Body weight and clinical signs of rats in each treatment group were recorded each day. Two days (48 hrs) after last dosing, the procedure was ended for all animals (day 8 of the course). Colon tissue (10 cm in length from anus) was collected for gross pathology (colon weight, ulceration) and histological evaluation according to the key shown in FIG. 26, and representative images were taken.

Results

Figure 24:
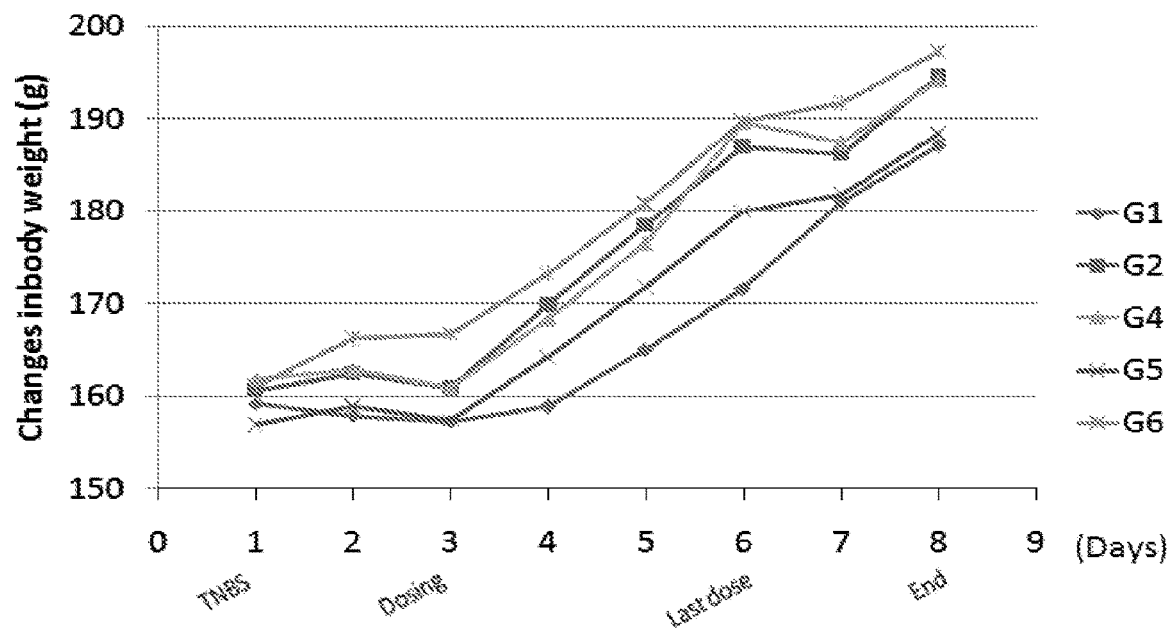
FIG. 24 shows the effect of humanized 1C5-VK2 antibody on rat body weight over time in a model of inflammatory bowel disease (IBD) induced by TNBS. Treatment groups include G1: untreated (n=5); G2: human IgG at 125 µg/kg, intraperitoneal (IP) (n=5); G4: 1C5-VK2 at 125 µg/kg, intraperitoneal (TP) (n=5); G5: 1C5-VK2 at 122 µg/kg, subcutaneous (SC) (n=6); and G6: 1C5-VK2 at 250 µg/kg, oral gavage (PO) (n=6).

FIG. 24 shows the effect of antibody treatment, on rat body weight. From one day of treatment (day 4 of the entire course), all treatment groups showed increased body weight, as compared to untreated controls.

Figure 25:
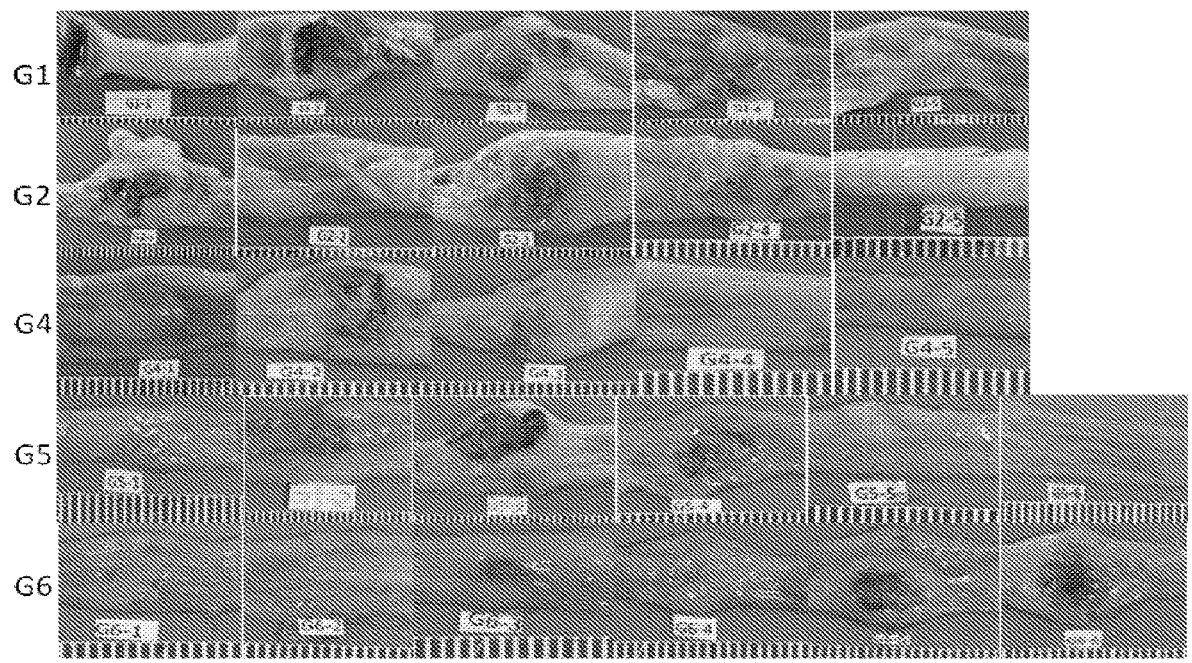
FIG. 25 shows representative gross images taken at day 8 of the IBD model. Treatment with humanized 1C5-VK2 antibody was given at 48 hours after the induction of the IBD mode. Treatment groups are as described above for FIG. 24.

Representative gross images of colon tissue samples are provided in FIG. 25, 4/5 (80%) of the untreated rats of control group (G1) showed serious colitis with severe ulceration, inflammation, and tissue, necrosis. Overall, the majority of rats treated with 1C5-VK2 (G4, G5 and G6) showed the signs of recovery, such as reduced inflammation (fewer inflammatory cells and less congestion), reduced tissue necrosis, covered ulceration (whole or partial) and better morphology (smoother bowel wall). In group G4, two rats (G4-4 and G4-5) showed no ulceration and inflammation; one rat (G4-3) showed thickening of the bowel wall with reduced inflammation and covered ulceration (recovering); and one rat (G4-1) showed thickening of the bowel wall and inflammation without ulceration. The remaining rats (G4-2) showed reduced inflammation and partially covered ulceration. Similarly, 4/6 (67%) of G5 rats (G5-1, G5-4, G5-5 and G5-6) showed signs of recovering, and 5/6 (83%) of G6 rats (G6-1, G6-2, G6-3, G6-4 and G-6-5) showed signs of recovering compared to control rats. These results illustrate that 1C5-VK2 treatment via either injection (group-G4 or -G5) or oral administration up-G6) resulted in significant mitigation of colitis ulceration and inflammation.

Figure 26:
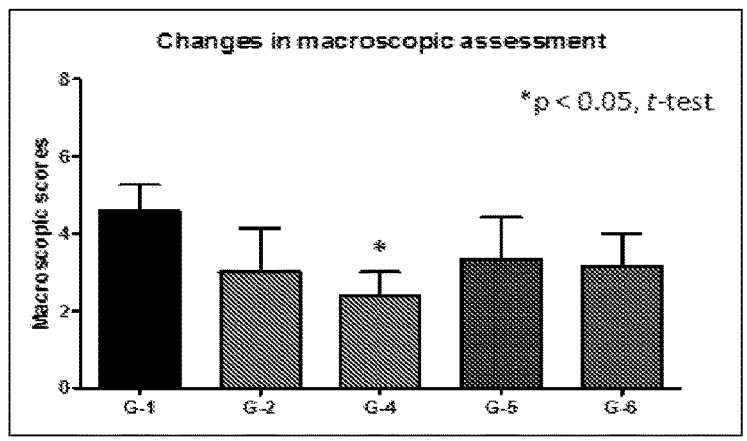
FIG. 26 shows the score of rat colon macroscopic assessment at day 8 of the rat IBD model. Treatment with humanized 1C5-VK2 antibody was given at 48 hours after the induction of the IBD mode. Treatment groups are as described above for FIG. 24. *indicates p<0.05 in a t-test comparison of the indicated treatment group with the untreated control group (G1).

Colon morphology and colitis pathological symptoms were macroscopically assessed in these tissue samples according to the key shown in FIG. 26. Scoring, indicated that antibody treatment resulted in a decrease in the severity of colitis pathology, with group G4 demonstrating a statistically significant decrease in scoring as compared to untreated controls.

Figure 27:
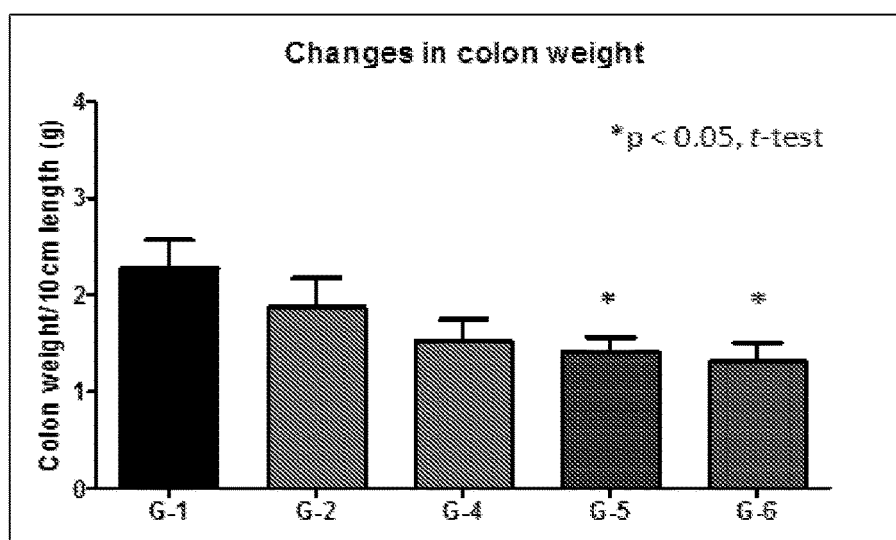
FIG. 27 shows the rat colon weight at day 8 of the IBD model. Treatment with humanized 1C5-VK2 antibody was given at 48 hours after the induction of the IBD mode. Treatment groups are as described above for FIG. 24. *indicates p<0.05 in a t-test comparison of the indicated treatment group with the untreated control group (G1).

Next, colons from each treatment group were weighed as a function of their length. As shown in FIG. 27, the colon weight of untreated rats were significantly increased due to inflammation and ulceration, while the colon weight of the rats treated with 1C5-NIK2 via SC (G5) or PO (G6) routes did not increase significantly. These data Suggested that the colons of group C5- and G6-rats were at a condition closer to normal rats compared to the untreated control rats.

Taken together, the results from Examples 8-10 demonstrate that treatment with humanized antibody against N-acetylglucosamine and N-acetyl-galactosamine displayed efficacy in two animal models of IBD. Two antibodies showed efficacy in a mouse model of IBD. Pathological signs of IBD such as ulceration and inflammation were mitigated by treatment, and epithelial regeneration was observed upon treatment.

SEQUENCES

All polypeptide sequences are presented N-terminal to C-terminal unless otherwise noted.

```
2F7H4 Heavy Chain Variable Region:
                                                   (SEQ ID NO: 1)
EVKLQQSGGGLVQPGGSLRLSCATSGFTFSDFYMEWVRQPPGKRLEWIAASRNKANDY

TTEYSASVKGRFIVSRDTSQSILYLQMNALRAEDTAIYYCARDAWFAYWGQGTIVTVSS

2F7H4 Light Chain Variable Region:
                                                   (SEQ ID NO: 2)
DIVITQTPSSLAVSVGEKVTMSCKSSQSLLYSSNQKNYLAWYQQKPGQSPKLLIYWAST

RESGVPDRFTGSGSGTDFTLTISSVKAEDLAVYYCQQYYSYPRTFGGGTKFEIK

1C5C9 Heavy Chain Variable Region:
                                                   (SEQ ID NO: 3)
EVQLEESGPELVKPGASVKISCKASGYTFPDYNIHWVKQSHGKSLEWIGCIYPYNGNTA

YNQKFKTKATLTVDTSSSTAYMDLRSLTSEDSAVYYCARSDLYYFGSRGFVYWGQGTT

VTVSS

1C5C9 Light Chain Variable Region:
                                                   (SEQ ID NO: 4)
DIVLTQSPSSLSASLGDRVTISCRASQDISTYLNWYQQKPDGTVKLLVYFTSRLHSGVPS

RFSGTGSGTDFSLTINNLDQEDIATYFCQQGNTLPWTFGGGTKLEIK

3C4F12 Heavy Chain Variable Region:
                                                   (SEQ ID NO: 5)
EVQLEESGGGLVKPGGSLKLSCAASGFAFSSYDMSWVRQTPEKRLEWVAYISSGGGST

YYPDTVKGRFTISRDNAKNTLYLQMSSLKSEDTAMYYCARRYYYGSSWAMDYWGQG

TMVTVSS

3C4F12 Light Chain Variable Region:
                                                   (SEQ ID NO: 6)
DIVMTQSTKFLLVSAGDRVTITCKASQSVSNDVAWYQQKPGQSPKLLIYYASNRYTGVP

DRFTGSGYGTDFTFTISTVQAEDLAVYFCQQDYSSPYTFGGGTKLEIK

Humanized 1C5C9 and parental-1C5C9 HVR-H1:
                                                   (SEQ ID NO: 7)
YTFPDYNIH Humanized 1C5C9 HVR-H2:
                                                   (SEQ ID NO: 8)
CIYPYNGNTA Humanized 1C5C9 HVR-H3:
                                                   (SEQ ID NO: 9)
SDLYYFGSRGFD Humanized 1C5-VK1 HVR-L1:
                                                   (SEQ ID NO: 10)
QASQDISTYLN Humanized 1C5-VK2/parental-1C5C9 HVR-L1:
                                                   (SEQ ID NO: 11)
RASQDISTYLN Humanized 1C5-VK1 HVR-L2:
                                                   (SEQ ID NO: 12)
FTSNLET Humanized 1C5-VK2 HVR-L2:
                                                   (SEQ ID NO: 13)
FTSSLQS
```

-continued

Humanized parental-1C5C9 HVR-L2:
(SEQ ID NO: 14)
FTSRLHS

Humanized 1C5-VK1/VK2/parental-1C5C9 HVR-L3:
(SEQ ID NO: 15)
QQGNTLPW

Humanized 1C5C9 Heavy Chain Variable Region:
(SEQ ID NO: 16)
QVQLVQSGAEVKKPGASVKVSCKASGYTFPDYNIHWVRQAPGQGLEWMGCIYPYNGN

TAYAQKFQGRVTMTRDTSISTAYMELSRLRSDDTAVYYCARSDLYYFGSRGFDYWGQ

GTLVTVSSA

Humanized 1C5C9 Heavy Chain:
(SEQ ID NO: 17)
QVQLVQSGAEVKKPGASVKVSCKASGYTFPDYNIHWVRQAPGQGLEWMGCIYPYNGN

TAYAQKFQGRVTMTRDTSISTAYMELSRLRSDDTAVYYCARSDLYYFGSRGFDYWGQ

GTLVTVSSASTKGPSVFPLAPSSKSTSGGTAALGCLVKDYFPEPVTVSWNSGALTSGVHT

FPAVLQSSGLYSLSSVVTVPSSSLGTQTYICNVNHKPSNTKVDKRVEPKSCDKTHTCPPC

PAPELLGGPSVFLFPPKPKDTLMISRTPEVTCVVVDVSHEDPEVKFNWYVDGVEVHNAK

TKPREEQYNSTYRVVSVLTVLHQDWLNGKEYKCKVSNKALPAPIEKTISKAKGQPREPQ

VYTLPPSRDELTKNQVSLTCLVKGFYPSDIAVEWESNGQPENNYKTTPPVLDSDGSFFLY

SKLTVDKSRWQQGNVFSCSVMHEALHNHYTQKSLSLSPGK

Humanized 1C5-VK1 Light Chain Variable Region:
(SEQ ID NO: 18)
DIQMTQSPSSLSASVGDRVTITCQASQDISTYLNWYQQKPGKAPKLLIYFTSNLETGVPS

RFSGSGSGTDFTLTISSLQPEDIATYYCQQGNTLPWTFGGGTKLE

Humanized 1C5-VK1 Light Chain:
(SEQ ID NO: 19)
DIQMTQSPSSLSASVGDRVTITCQASQDISTYLNWYQQKPGKAPKLLIYFTSNLETGVPS

RFSGSGSGTDFTLTISSLQPEDIATYYCQQGNTLPWTFGGGTKLERTVAAPSVFIFPPSDE

QLKSGTASVVCLLNNFYPREAKVQWKVDNALQSGNSQESVTEQDSKDSTYSLSSTLTLS

KADYEKHKVYACEVTHQGLSSPVTKSFNRGEC

Humanized 1C5-VK2 Light Chain Variable Region:
(SEQ ID NO: 20)
DIQMTQSPSSLSASVGDRVTITCRASQDISTYLNWYQQKPGKAPKLLIYFTSSLQSGVPSR

FSGSGSGTDFTLTISSLQPEDIATYYCQQGNTLPWTFGGGTKLE

Humanized 1C5-VK2 Light Chain:
(SEQ ID NO: 21)
DIQMTQSPSSLSASVGDRVTITCRASQDISTYLNWYQQKPGKAPKLLIYFTSSLQSGVPSR

FSGSGSGTDFTLTISSLQPEDIATYYCQQGNTLPWTFGGGTKLERTVAAPSVFIFPPSDEQ

LKSGTASVVCLLNNFYPREAKVQWKVDNALQSGNSQESVTEQDSKDSTYSLSSTLTLSK

ADYEKHKVYACEVTHQGLSSPVTKSFNRGEC

Humanized parental-1C5C9 Light Chain Variable Region:
(SEQ ID NO: 22)
DIQMTQSPSSLSASVGDRVTITCRASQDISTYLNWYQQKPGKAPKLLIYFTSRLHSGVPS

RFSGSGSGTDFTLTISSLQPEDIATYYCQQGNTLPWTFGGGTKLE

Humanized parental-1C5C9 Light Chain:
(SEQ ID NO: 23)
DIQMTQSPSSLSASVGDRVTITCRASQDISTYLNWYQQKPGKAPKLLIYFTSRLHS

GVPSRFSGSGSGTDFTLTISSLQPEDIATYYCQQGNTLPWTFGGGTKLERTVAAPSVFIFP

PSDEQLKSGTASVVCLLNNFYPREAKVQWKVDNALQSGNSQESVTEQDSKDSTYSLSST

LTLSKADYEKHKVYACEVTHQGLSSPVTKSFNRGEC

2F7H4 HVR-H1:
FTFSDFYME                                              (SEQ ID NO: 24)

2F7H4 HVR-H2:
ASRNKANDYTTEYSASVKG                                    (SEQ ID NO: 25)

2F7H4 HVR-H3:
DAWFA                                                  (SEQ ID NO: 26)

2F7H4 HVR-L1:
KSSQSLLYSSNQKNYLA                                      (SEQ ID NO: 27)

2F7H4 HVR-L2:
WASTRES                                                (SEQ ID NO: 28)

2F7H4 HVR-L3:
QQYYSYPR                                               (SEQ ID NO: 29)

1C5C9 HVR-H2:
CIYPYNGNTAYNQKFKT                                      (SEQ ID NO: 30)

1C5C9 HVR-H3:
SDLYYFGSRGFV                                           (SEQ ID NO: 31)

3C4F12 HVR-H1:
FAFSSYDMS                                              (SEQ ID NO: 32)

3C4F12 HVR-H2:
YISSGGGSTYYPDTVKG                                      (SEQ ID NO: 33)

3C4F12 HVR-H3:
RYYYGSSWAMD                                            (SEQ ID NO: 34)

3C4F12 HVR-L1:
KASQSVSNDVA                                            (SEQ ID NO: 35)

3C4F12 HVR-L2:
YASNRYT                                                (SEQ ID NO: 36)

3C4F12 HVR-L3:
QQDYSSPY                                               (SEQ ID NO: 37)

---

What is claimed is:

1. An isolated polynucleotide comprising a nucleic acid sequence encoding an isolated monoclonal antibody, which antibody specifically binds to an epitope comprising N-acetylglucosamine or N-acetyl-galactosamine, wherein the epitope is expressed by a cancer cell or an inflammatory cell, and wherein the antibody comprises:
   (a) a heavy chain variable region comprising three HVRs from the amino acid sequence of SEQ ID NO:1, and a light chain variable region comprising three HVRs from the amino acid sequence of SEQ ID NO:2;
   (b) a heavy chain variable region comprising three HVRs from the amino acid sequence of SEQ ID NO:3, and a light chain variable region comprising three HVRs from the amino acid sequence of SEQ ID NO:4;
   (c) a heavy chain variable region comprising three HVRs from the amino acid sequence of SEQ ID NO:5, and a light chain variable region comprising three HVRs from the amino acid sequence of SEQ ID NO:6;
   (d) a heavy chain variable region comprising an HVR-H1 sequence of SEQ ID NO: 24, an HVR-H2 sequence of SEQ ID NO: 25, and an HVR-H3 sequence of SEQ ID NO: 26; and a light chain variable region comprising an HVR-L1 sequence of SEQ ID NO: 27, an HVR-L2 sequence of SEQ ID NO: 28, and an HVR-L3 sequence of SEQ ID NO: 29;
   (e) a heavy chain variable region comprising an HVR-H1 sequence of SEQ ID NO: 7, an HVR-H2 sequence of SEQ ID NO: 30, and an HVR-H3 sequence of SEQ ID NO: 31; and a light chain variable region comprising an HVR-L1 sequence of SEQ ID NO: 11, an HVR-L2 sequence of SEQ ID NO: 14, and an HVR-L3 sequence of SEQ ID NO: 15;
   (f) a heavy chain variable region comprising an HVR-H1 sequence of SEQ ID NO: 32, an HVR-H2 sequence of SEQ ID NO: 33, and an HVR-H3 sequence of SEQ ID NO: 34; and a light chain variable region comprising an HVR-L1 sequence of SEQ ID NO: 35, an HVR-L2 sequence of SEQ ID NO: 36, and an HVR-L3 sequence of SEQ ID NO: 37;
   (g) a heavy chain variable region comprising an HVR-H1 sequence of SEQ ID NO: 7, an HVR-H2 sequence of SEQ ID NO: 8, and an HVR-H3 sequence of SEQ ID NO: 9; and a light chain variable region comprising an HVR-L1 sequence of SEQ ID NO: 10, an HVR-L2 sequence of SEQ ID NO: 12, and an HVR-L3 sequence of SEQ ID NO: 15;
   (h) a heavy chain variable region comprising an HVR-H1 sequence of SEQ ID NO: 7, an HVR-H2 sequence of SEQ ID NO: 8, and an HVR-H3 sequence of SEQ ID NO: 9; and a light chain variable region comprising an HVR-L1 sequence of SEQ ID NO: 11, an HVR-L2 sequence of SEQ ID NO: 13, and an HVR-L3 sequence of SEQ ID NO: 15; or
   (i) a heavy chain variable region comprising an HVR-H1 sequence of SEQ ID NO: 7, an HVR-H2 sequence of SEQ ID NO: 8, and an HVR-H3 sequence of SEQ ID NO: 9; and a light chain variable region comprising an HVR-L1 sequence of SEQ ID NO: 11, an HVR-L2 sequence of SEQ ID NO: 14, and an HVR-L3 sequence of SEQ ID NO: 15.

2. The polynucleotide of claim 1, wherein the antibody is an antibody fragment.

3. The polynucleotide of claim 1, wherein the antibody is a humanized, human, or chimeric antibody.

4. The polynucleotide of claim 1, wherein the antibody comprises:
   (a) a heavy chain variable region comprising the amino acid sequence of SEQ ID NO:1, and a light chain variable region comprising the amino acid sequence of SEQ ID NO:2;
   (b) a heavy chain variable region comprising the amino acid sequence of SEQ ID NO:3, and a light chain variable region comprising the amino acid sequence of SEQ ID NO:4;
   (c) a heavy chain variable region comprising the amino acid sequence of SEQ ID NO:5, and a light chain variable region comprising the amino acid sequence of SEQ ID NO:6;
   (d) a heavy chain variable region comprising the amino acid sequence of SEQ ID NO: 16, and a light chain variable region comprising the amino acid sequence of SEQ ID NO: 18;
   (e) a heavy chain variable region comprising the amino acid sequence of SEQ ID NO: 16, and a light chain variable region comprising the amino acid sequence of SEQ ID NO: 20; or
   (f) a heavy chain variable region comprising the amino acid sequence of SEQ ID NO: 16, and a light chain variable region comprising the amino acid sequence of SEQ ID NO: 22.

5. A vector comprising a nucleic acid sequence encoding an isolated monoclonal antibody, which antibody specifically binds to an epitope comprising N-acetylglucosamine or N-acetyl-galactosamine, wherein the epitope is expressed by a cancer cell or an inflammatory cell, and wherein the antibody comprises:
   (a) a heavy chain variable region comprising three HVRs from the amino acid sequence of SEQ ID NO:1, and a light chain variable region comprising three HVRs from the amino acid sequence of SEQ ID NO:2;
   (b) a heavy chain variable region comprising three HVRs from the amino acid sequence of SEQ ID NO:3, and a light chain variable region comprising three HVRs from the amino acid sequence of SEQ ID NO:4;
   (c) a heavy chain variable region comprising three HVRs from the amino acid sequence of SEQ ID NO:5, and a light chain variable region comprising three HVRs from the amino acid sequence of SEQ ID NO:6;
   (d) a heavy chain variable region comprising an HVR-H1 sequence of SEQ ID NO: 24, an HVR-H2 sequence of SEQ ID NO: 25, and an HVR-H3 sequence of SEQ ID NO: 26; and a light chain variable region comprising an HVR-L1 sequence of SEQ ID NO: 27, an HVR-L2 sequence of SEQ ID NO: 28, and an HVR-L3 sequence of SEQ ID NO: 29;
   (e) a heavy chain variable region comprising an HVR-H1 sequence of SEQ ID NO: 7, an HVR-H2 sequence of SEQ ID NO: 30, and an HVR-H3 sequence of SEQ ID NO: 31; and a light chain variable region comprising an HVR-L1 sequence of SEQ ID NO: 11, an HVR-L2 sequence of SEQ ID NO: 14, and an HVR-L3 sequence of SEQ ID NO: 15;
   (f) a heavy chain variable region comprising an HVR-H1 sequence of SEQ ID NO: 32, an HVR-H2 sequence of SEQ ID NO: 33, and an HVR-H3 sequence of SEQ ID NO: 34; and a light chain variable region comprising an HVR-L1 sequence of SEQ ID NO: 35, an HVR-L2 sequence of SEQ ID NO: 36, and an HVR-L3 sequence of SEQ ID NO: 37;
   (g) a heavy chain variable region comprising an HVR-H1 sequence of SEQ ID NO: 7, an HVR-H2 sequence of SEQ ID NO: 8, and an HVR-H3 sequence of SEQ ID NO: 9; and a light chain variable region comprising an HVR-L1 sequence of SEQ ID NO: 10, an HVR-L2 sequence of SEQ ID NO: 12, and an HVR-L3 sequence of SEQ ID NO: 15;

(h) a heavy chain variable region comprising an HVR-H1 sequence of SEQ ID NO: 7, an HVR-H2 sequence of SEQ ID NO: 8, and an HVR-H3 sequence of SEQ ID NO: 9; and a light chain variable region comprising an HVR-L1 sequence of SEQ ID NO: 11, an HVR-L2 sequence of SEQ ID NO: 13, and an HVR-L3 sequence of SEQ ID NO: 15; or (i) a heavy chain variable region comprising an HVR-H1 sequence of SEQ ID NO: 7, an HVR-H2 sequence of SEQ ID NO: 8, and an HVR-H3 sequence of SEQ ID NO: 9; and a light chain variable region comprising an HVR-L1 sequence of SEQ ID NO: 11, an HVR-L2 sequence of SEQ ID NO: 14, and an HVR-L3 sequence of SEQ ID NO: 15.

6. An isolated host cell comprising the vector of claim 5.

7. A method of producing an antibody, comprising culturing the host cell of claim 6 that produces the antibody encoded by the nucleic acid, and recovering the antibody from the cell culture.

8. The vector of claim 5, wherein the antibody is an antibody fragment.

9. The vector of claim 5, wherein the antibody is a humanized, human, or chimeric antibody.

10. The vector of claim 5, wherein the antibody comprises:

(a) a heavy chain variable region comprising the amino acid sequence of SEQ ID NO:1, and a light chain variable region comprising the amino acid sequence of SEQ ID NO:2;

(b) a heavy chain variable region comprising the amino acid sequence of SEQ ID NO:3, and a light chain variable region comprising the amino acid sequence of SEQ ID NO:4;

(c) a heavy chain variable region comprising the amino acid sequence of SEQ ID NO:5, and a light chain variable region comprising the amino acid sequence of SEQ ID NO:6;

(d) a heavy chain variable region comprising the amino acid sequence of SEQ ID NO: 16, and a light chain variable region comprising the amino acid sequence of SEQ ID NO: 18;

(e) a heavy chain variable region comprising the amino acid sequence of SEQ ID NO: 16, and a light chain variable region comprising the amino acid sequence of SEQ ID NO: 20; or (f) a heavy chain variable region comprising the amino acid sequence of SEQ ID NO: 16, and a light chain variable region comprising the amino acid sequence of SEQ ID NO: 22.

* * * * *